United States Patent
Steffan et al.

(10) Patent No.: US 7,241,791 B2
(45) Date of Patent: Jul. 10, 2007

(54) SUBSTITUTED 4-(INDAZOL-3-YL)PHENOLS

(75) Inventors: Robert J. Steffan, Langhorne, PA (US); Edward M. Matelan, Royersford, PA (US); Mark A. Ashwell, Carlisle, MA (US); William R. Solvibile, East Windsor, NJ (US)

(73) Assignee: Wyeth, Madison, NJ (US)

( * ) Notice: Subject to any disclaimer, the term of this patent is extended or adjusted under 35 U.S.C. 154(b) by 432 days.

(21) Appl. No.: 10/670,646

(22) Filed: Sep. 24, 2003

(65) Prior Publication Data

US 2004/0167127 A1 Aug. 26, 2004

Related U.S. Application Data

(60) Provisional application No. 60/413,931, filed on Sep. 25, 2002.

(51) Int. Cl.
 A61K 31/416 (2006.01)
 C07D 231/56 (2006.01)

(52) U.S. Cl. ............... 514/403; 514/406; 548/361.1

(58) Field of Classification Search ............ 548/361.1; 514/403, 406
See application file for complete search history.

(56) References Cited

U.S. PATENT DOCUMENTS

| 5,856,503 A | 1/1999 | Aebi et al. | |
|---|---|---|---|
| 2002/0103229 A1* | 8/2002 | Bhagwat et al. | ............ 514/338 |
| 2006/0030612 A1* | 2/2006 | Steffan et al. | ............ 514/406 |

FOREIGN PATENT DOCUMENTS

| EP | 0470039 | 2/1992 |
|---|---|---|
| EP | 0778271 | 6/1997 |
| EP | 1 380 576 A1 | 1/2004 |
| JP | 01180878 | 1/1988 |
| JP | 02007066 | 6/1988 |
| JP | 01-180878 * | 7/1989 |
| JP | 05331168 | 5/1992 |
| JP | 06206872 | 10/1993 |
| WO | WO 94/07865 | 4/1994 |
| WO | WO 99/18941 | 4/1999 |
| WO | 02/010137 A2 | 2/2002 |
| WO | 02/051821 A1 | 7/2002 |
| WO | 02/083648 A1 | 10/2002 |
| WO | 03/050095 A1 | 6/2003 |
| WO | 03/051860 A2 | 6/2003 |
| WO | 04/000817 A2 | 12/2003 |

OTHER PUBLICATIONS

File REGISTRY on STN, Registry No. 328279-69-2, Mar. 21, 2001.*
Stadlbauer, W., Product class 2: 1H- and 2H-indazoles, Science of Synthesis (2002), 12, 227-324.*
Krishnan et al., Reactions of hydroxybenzophenone with hydrozines, Journal of Heterocyclic Chemistry (1988), 25(2), 447-52.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls during to slow late-stage Alzheimer's [online], [retrieved on Sep. 23, 2003]. Retrieved from the Internet,URL;http://www.cnn.com/2003/HEALTH/conditions/09/24/alzheimers.drug.ap/index.html>.*
Nathan, L., et al., Circulation Research, pp. 377-385, Aug. 20, 1999.
Grodstein, F., eta l., Annals of Internal Medicine, vol. 133, No. 12, pp. 933-941, Dec. 19, 2000.
Grodstein, F., et al., Annals of Internal Medicine, vol. 135, No. 1, pp. 1-8, Jul. 3, 2001.
Schonknecht, P., et al., Neuroscience Letters, 307, 2001, pp. 122-124.
Hulley, S., et al., JAMA, vol. 280, No. 7, Aug. 19, 1998, pp. 605-613.
Yuan, M., et al., Science, vol. 293, pp. 1673-1677, Aug. 31, 2001.
Pelletier, J-P., et al., Arthritis & Rheumatism, vol. 44, No. 6, pp. 1237-1247, Jun. 2001.

(Continued)

Primary Examiner—Rebecca Anderson
(74) Attorney, Agent, or Firm—Woodcock Washburn LLP

(57) ABSTRACT

This invention provides compound of formulae I or II having the structure

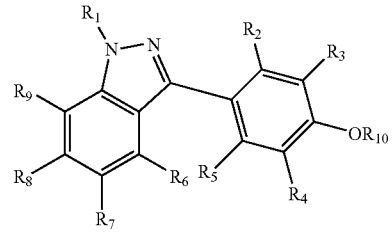

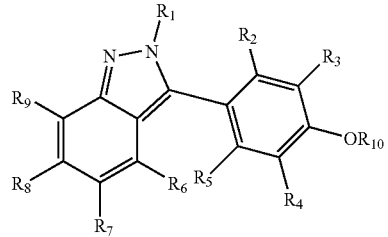

wherein
$R_1$, $R_2$, $R_3$, $R_4$, $R_5$, $R_6$, $R_7$, $R_8$, $R_9$, and $R_{10}$ are as defined in the specification or a pharmaceutically acceptable salt thereof which are useful for the treatment of the inflammatory component of diseases and are particularly useful in treating atherosclerosis, myocardial infarction, congestive heart failure, inflammatory bowel disease, arthritis, type II diabetes, and autoimmune diseases such as multiple sclerosis and rheumatiod arthritis.

8 Claims, No Drawings

OTHER PUBLICATIONS

Collot, V., et al., Tetrahedron, 55, pp. 6917-6922, 1999.
Collot, V., et al., Tetrahedron Letters, 41, pp. 4363-4366, 2000.
Collot, V., et al., Tetrahedron Letters, 41, pp. 9053-9057, 2000.
Patel, M., et al., Bioorganic & Medicinal Chemistry Letters, 9, pp. 3217-3220, 1999.
Huang, J., et al., J. Am. Chem. Soc., 121, pp. 9889-9890, 1999.
Rodriguez, M.J., et al., Bioorganic & Medicinal Chemistry Letters, 9, pp. 1863-1868, 1999.
Roth, A., Journal of Neuroscience Research, 57, pp. 399-404, 1999.
Kurebayashi, S., et al., J. Steroid Biochem. Molec., Biol., vol. 60, No. 1-2, pp. 11-17, 1997.
Shutske, G. M. et al., "Heterocyclic oxyacetic acid diuretics: indazole, benzisothiazole, and benzisothiazole 1,1-dioxide analogs of [[7-chloro-3-(2-fluorophenyl)-1,2-benzisoxazol-6-yl]oxy]acetic acid," *J Med Chem*, 1983, 26(9), 1307-11.

* cited by examiner

SUBSTITUTED 4-(INDAZOL-3-YL)PHENOLS

This application claims priority from now abandoned, provisional application Ser. No. 60/413,931, filed Sep. 25, 2002, the entire disclosure of which is hereby incorporated by reference.

BACKGROUND

This invention relates to ligands for the estrogen receptor (ER), and specifically relates to substituted 4-(indazol-3-yl) phenols useful for the treatment of the inflammatory component of diseases and are particularly useful in treating atherosclerosis, myocardial infarction, congestive heart failure, inflammatory bowel disease, arthritis, type II diabetes, and autoimmune diseases such as multiple sclerosis and rheumatoid arthritis.

The ability of ligands for the estrogen receptor to inhibit inflammatory gene expression causing a reduction of cytokines, chemokines, adhesion molecules and inflammatory enzymes provides a means to treat the inflammatory component of diseases such as atherosclerosis, myocardial infarction (MI), congestive heart failure (CHF), inflammatory bowel disease and arthritis. Other potential therapeutic indications for these type of molecules include type II diabetes (Cefalu, *J Womens Health & Gender-based Med.* 2001, 10, 241 & Yuan et al., *Science*, 2001, 293, 1673), osteoarthritis (Pelletier et al., *Arthr. & Rheum.*, 2001, 44:1237 and Felson et al., *Curr Opinion Rheum*, 1998, 10, 269) asthma (Chin-Chi Lin et. al., *Immunol. Lett.*, 2000, 73, 57), Alzheiemer's disease (Roth, A. et. al.,; *J. Neurosci. Res.*, 1999, 57, 399) and autoimmune diseases such as multiple sclerosis and rheumatoid arthritis.

A common component of these chronic inflammatory conditions is polymorphonuclear leukocyte and monocyte infiltration into the site of damage through increased expression of cytokines and adhesion molecules responsible for their recruitment. Overproduction of the cytokine interleukin (IL-6) has been associated with states of chronic inflammation (Bauer M. A., Herrmann F., *Ann. Hematol.*, 1991, 62, 203). Synthesis of the IL-6 gene is induced by the transcription factor nuclear factor κB (NF-κB). Interference at this step in the inflammatory process can effectively regulate the uncontrolled proliferative process that occurs in these chronic conditions.

In endothelial cells, 17β-estradiol (E2) inhibits IL-1β induced NF-κB reporter activity and IL-6 expression in an ER dependent fashion (Kurebayashi S. et. al., *J. Steroid Biochem. Molec. Biol.*, 1997, 60, 11). This correlates with anti-inflammatory action of E2 in vivo as confirmed in different animal models of inflammation. In models of atherosclerosis, E2 was shown to protect endothelial cell integrity and function and to reduce leukocyte adhesion and intimal accumulation (Adams, M. R. et al., *Arterio.*, 1990, 1051, Sullivan, T. R. et al. *J. Clin. Invst.* 1995, 96, 2482, Nathan, L. et. al., *Circ. Res.*, 1999, 85, 377). Similar effects of estrogen on the vascular wall have also been demonstrated in animal models of myocardial infarction (Delyani, J. A. et al., *J. Molec. Cell. Cardiol.*, 1996, 28, 1001) and congestive heart failure. Clinically, estrogen replacement therapy (ERT) has been demonstrated to reduce the risk of mortality in patients with both CHF (Reis et. al., *J. Am. Coll. Cardio.*, 2000, 36, 529) and MI (Grodstein, F. et. al., *Ann. Int. Med.*, 2000, 133, 933, Alexander et. al., *J. Am. Coll. Cardio.*, 2001, 38, 1 and Grodstein F. et. al., *Ann. Int. Med*, 2001, 135,1). In ERT, clinical studies demonstrated an influence of E2 on the decrease in the production of β-amyloid 1-42 (Aβ42), a peptide central for the formation of senile plaques in Alzheimer's disease (Schonknecht, P. et. al., *Neurosci. Lett.*, 2001, 307, 122).

However, 17-β-estradiol also strongly stimulates creatine kinase expression. Thus, in ERT some potential unwanted side effects, such as an increase risk of cardiovascular events in the first year of use, have been demonstrated (Hulley, S. et. al., *J. Am. Med. Assoc.*, 1998, 280, 605) as well as proliferative effects on uterine and breast tissue.

DESCRIPTION OF THE INVENTION

The invention provides substituted 4-(1H-indazol-3-yl) phenols represented by the general formula I and substituted 4-(2H-indazol-3-yl)phenols represented by formula II that are useful for the treatment of the inflammatory component of diseases and are particularly useful in treating atherosclerosis, myocardial infarction, congestive heart failure, inflammatory bowel disease, arthritis, type II diabetes, and autoimmune diseases such as multiple sclerosis and rheumatoid arthritis.

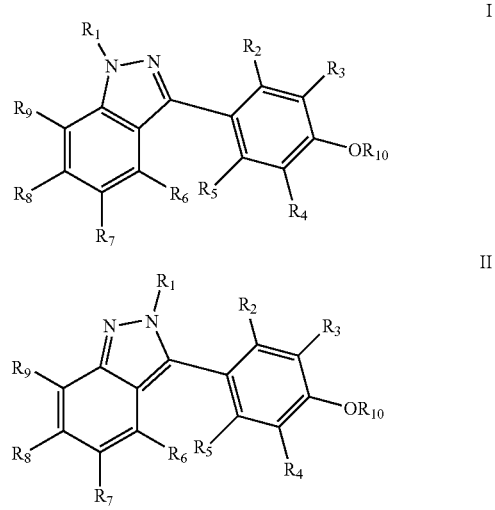

wherein
$R_1$ is hydrogen, alkyl of 1–6 carbon atoms, alkenyl of 2–7 carbon atoms, cycloalkyl of 3–8 carbon atoms, cycloalkenyl of 4–8 carbon atoms, aryl of 6–20 carbon atoms, arylalkyl of 7–26 carbon atoms, or a saturated, unsaturated, or partially unsaturated heterocyclic ring or ring system of 4–14 atoms, containing 1–4 heteroatoms selected from N, O, and S;

$R_2$, $R_3$, $R_4$, and $R_5$, are each, independently, hydrogen, alkyl of 1–6 carbon atoms, alkenyl of 2–7 carbon atoms, hydroxy, alkoxy of 1–6 carbon atoms, aryloxy of 6–20 carbon atoms, halogen, trifluoromethyl, —CN, —NO$_2$, —CHO, or —CO$_2$R$_{11}$;

$R_6$, $R_7$, $R_8$, and $R_9$, are each, independently, hydrogen, alkyl of 1–6 carbon atoms, alkenyl of 2–7 carbon atoms, hydroxy, alkoxy of 1–6 carbon atoms, aryloxy of 6–20 carbon atoms, halogen, trifluoromethyl, —CO$_2$R$_{11}$, aryl of 6–20 carbon atoms, arylalkyl of 7–26 carbon atoms, or a saturated, unsaturated, or partially unsaturated heterocyclic ring or ring system of 4–14 atoms, containing 1–4 heteroatoms selected from N, O, and S;

$R_{10}$ is hydrogen, —COR$_{11}$, —CONHR$_{11}$, —P(=O)(OH)OR$_{11}$, or —CO(CH$_2$)$_n$CH(NHR$_{12}$)CO$_2$R$_{11}$;

$R_{11}$ is hydrogen, alkyl of 1–6 carbon atoms, aryl of 6–20 carbon atoms, or arylalkyl of 7–26 carbon atoms;

$R_{12}$ is hydrogen or —$CO_2R_{11}$;

n=0–3, or a pharmaceutically acceptable salt thereof.

As used herein, the term "alkyl" includes both branched and straight-chain saturated aliphatic hydrocarbon groups having the specified number of carbon atoms, e.g. methyl (Me), ethyl (Et), propyl (Pr), isopropyl (i-Pr), isobutyl (i-Bu), secbutyl (s-Bu), tertbutyl (t-Bu), isopentyl, isohexyl and the like. The term "alkyl" further includes both unsubstituted and mono-, di- and tri-substituted hydrocarbon groups, with halogen substitution particularly preferred.

The term "alkenyl" refers to an unsaturated or partially unsaturated aliphatic hydrocarbon group having the specified number of carbon atoms, for example ethenyl, 1-propenyl, 2, butenyl, etc. The term "alkenyl" further includes both unsubstituted and mono-, di- and tri-substituted hydrocarbon groups, with halogen substitution particularly preferred.

The term "cycloalkyl" includes cyclized alkyl chains having the specified number of carbon atoms, e.g., cyclopropyl, cyclobutyl, cyclopentyl, and cyclohexyl. The term "cycloalkenyl" includes cyclized alkyl chains containing an alkenyl group having the specified number of carbon atoms, e.g., cyclopentenyl, cyclohexenyl, etc. The term "halogen" includes fluorine, chlorine, iodine and bromine.

The term "aryl" means an aromatic carbocyclic moiety of up to 20 carbon atoms, e.g., 6–20, which may be a single ring (monocyclic) or multiple rings (bicyclic, up to three rings of which at least one ring is aromatic) fused together or linked covalently. Any suitable ring position of the aryl moiety may be covalently linked to the defined chemical structure. Examples of aryl moieties include, but are not limited to, chemical groups such as phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like.

The term "arylalkyl" means aryl, as herein before defined, suitably substituted on any open ring position with an alkyl moiety wherein the alkyl chain is either a ($C_1$–$C_6$) straight or ($C_2$–$C_7$) branched-chain saturated hydrocarbon moiety. Examples of arylalkyl moieties include, but are not limited to, chemical groups such as benzyl, 1-phenylethyl, 2-phenylethyl, diphenylmethyl, 3-phenylpropyl, 2-phenylpropyl, fluorenylmethyl, and homologs, isomers, and the like.

The term "heterocyclic ring or ring system", employed alone or in combination with other terms, is defined herein as an unsaturated, partially unsaturated or saturated ring or ring system, which may be a single ring (monocyclic) or multiple rings (bicyclic, up to three rings) fused together or linked covalently. The rings may contain from one to four hetero atoms selected from nitrogen (N), oxygen (O), or sulfur (S), wherein the nitrogen or sulfur atom(s) are optionally oxidized, or the nitrogen atom(s) are optionally quarternized. Any suitable ring position of the heterocyclic moiety may be covalently linked to the defined chemical structure. Examples of unsaturated heterocyclic rings or ring systems include, but are not limited to, heterocycles such as furan, thiophene, pyrrole, N-methylpyrrole, pyrazole, N-methylpyrazole, imidazole, N-methylimidazole, oxazole, isoxazole, thiazole, isothiazole, 1H-tetrazole, 1-methyltetrazole, 1,3,4-oxadiazole, 1H-1,2,4-triazole, 1-methyl-1,2,4-triazole 1,3,4-triazole, 1-methyl-1,3,4-triazole, pyridine, pyrimidine, pyrazine, pyridazine, benzoxazole, benzisoxazole, benzothiazole, benzofuran, benzothiophene, thianthrene, dibenzo[b,d]furan, dibenzo[b,d]thiophene, benzimidazole, N-methylbenzimidazole, indole, indazole, quinoline, isoquinoline, quinazoline, quinoxaline, purine, pteridine, 9H-carbazole, β-carboline, and the like. Examples of saturated or partially unsaturated heterocyclic rings or ring systems include, but are not limited to, chemical groups such as azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, tetrahydroisoquinolinyl, and the like.

As used herein the terms "aryl" and "heterocyclic" as a group or part of a group (e.g., arylalkyl, aryloxy) include such groups optionally mono-, di- or tri-substituted with one or more substituents, the same or different, such as those selected from the following:

halogen, hydroxy, alkyl of 1–6 carbon atoms; alkenyl of 2–6 carbon atoms; cycloalkyl of 3–6 carbon atoms, alkoxy of 1–6 carbon atoms; alkylthio of 1–6 carbon atoms;

hydroxyalkyl of 1 to 6 carbon atoms, CN, perfluoroalkyl of 1–4 carbon atoms, —O-perfluoroalkyl of 1–4 carbon atoms, $NO_2$, amino, alkylsulfonyl of 1–6 carbon atoms; carboxy, and alkoxycarbonyl of 2–7 carbon atoms.

As used herein the terms "alkyl" and "alkenyl" include such groups optionally mono- or poly-substituted with one or more substituents, the same or different, such as those selected from the following: halogen, hydroxy, cycloalkyl of 3–8 carbon atoms and cycloalkenyl of 4–8 carbon atoms.

The compounds of formula I and formula II can be converted to salts, in particular pharmaceutically acceptable salts using art recognized procedures. The compounds of formulas I and II that have a basic center can form acid addition salts. These are formed, for example, with strong inorganic acids, such as mineral acids for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid such as saturated or unsaturated dicarboxylic acids, for example oxalic, malonic, succinic, maleic, fumaric, phthalic, or terephthalic acid, such as hydroxycarboxylic acids, for example ascorbic, glycolic, lactic, malic, tartaric or citric acid, such as amino acids, for example aspartic or glutamic acid, or such as benzoic acid, or with organic sulfonic acids, such as alkane- (of 1 to 4 carbon atoms) or arylsulfonic acids, for example methane- or p-toluenesulfonic acid. Corresponding acid addition salts can also be formed having, if desired, an additionally present basic center. The compounds of formula I having at least one acid group can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethylpropylamine, or a mono-, di-, or trihydroxy lower alkylamine, for example mono-, di- or triethanolamine. Internal salts may furthermore be formed. Salts which are unsuitable for pharmaceutical uses but which can be employed, for example, for the isolation or purification of free compounds I or their pharmaceutically acceptable salts, are also included.

As used in accordance with this invention, the term "providing," with respect to providing a compound or substance covered by this invention, means either directly administering such a compound or substance, or administering a prodrug, derivative, or analog which will form the effective amount of the compound or substance within the body. This invention also covers providing the compounds of this invention to treat the disease states disclosed herein that the compounds are useful for treating.

Examples of $R_1$ include alkyl of 1–6 carbon atoms (e.g., methyl, ethyl, propyl, isopropyl, butyl), alkenyl of 2–7 carbon atoms (e.g., allyl), cycloalkyl of 3–8 carbon atoms, cycloalkenyl of 4–8 carbon atoms (e.g. cyclohexyl, cyclopentyl, cyclobutyl), or a saturated, unsaturated, or partially unsaturated heterocyclic ring or ring system of 4–14 atoms, containing 1–4 heteroatoms selected from N, O, and S (e.g., thienyl). Preferably $R_1$ is alkyl of 1–6 carbon atoms, alkenyl of 2–7 carbon atoms, cycloalkyl of 3–8 carbon atoms, or cycloalkenyl of 4–8 carbon atoms. Most preferably $R_1$ is alkyl of 1–6 carbon atoms or alkenyl of 2–7 carbon atoms. When substituted examples of alkyl are cyclohexylmethyl, 2,2,2-trifluoroethyl and 2-hydroxyethyl. Other examples of $R_1$ include phenyl and substituted phenyl.

Examples of $R_2$ include hydrogen, alkyl of 1–6 carbon atoms (e.g., methyl), alkenyl of 2–7 carbon atoms, hydroxy, alkoxy of 1–6 carbon atoms or halogen. Preferably $R_2$ is hydrogen, alkyl of 1–6 carbon atoms, halogen or hydroxy.

Examples of $R_7$ and $R_9$ are each, independently, hydrogen, alkyl of 1–6 carbon atoms, hydroxy, halogen, trifluoromethyl, —$CO_2R_{11}$, aryl of 6–20 carbon atoms, arylalkyl of 7–26 carbon atoms, or a saturated, unsaturated, or partially unsaturated heterocyclic ring or ring system of 4–14 atoms, containing 1–4 heteroatoms selected from N, O, and S.

Examples of $R_9$ include alkyl of 1–6 carbon atoms, halogen, trifluoromethyl, —$CO_2R_{11}$, aryl of 6–20 carbon atoms, arylalkyl of 7–26 carbon atoms, or a saturated, unsaturated, or partially unsaturated heterocyclic ring or ring system of 4–14 atoms, containing 1–4 heteroatoms selected from N, O, and S. Preferably $R_9$ is alkyl of 1–6 carbon atoms, halogen, or trifluoromethyl.

$R_{10}$ may be for example hydrogen.

Preferred compounds of this invention include those in which:

(A). $R_1$ is alkyl of 1–6 carbon atoms, alkenyl of 2–7 carbon atoms, cycloalkyl of 3–8 carbon atoms, cycloalkenyl of 4–8 carbon atoms, or a saturated, unsaturated, or partially unsaturated heterocyclic ring or ring system of 4–14 atoms, containing 1–4 heteroatoms selected from N, O, and S;

$R_2$ is hydrogen, alkyl of 1–6 carbon atoms, alkenyl of 2–7 carbon atoms, hydroxy, alkoxy of 1–6 carbon atoms, or halogen;

$R_7$ and $R_9$, are each, independently, hydrogen, alkyl of 1–6 carbon atoms, hydroxy, halogen, trifluoromethyl, —$CO_2R_{11}$, aryl of 6–20 carbon atoms, arylalkyl of 7–26 carbon atoms, or a saturated, unsaturated, or partially unsaturated heterocyclic ring or ring system of 4–14 atoms, containing 1–4 heteroatoms selected from N, O, and S, where the remaining substituents are as defined above.

Preferred compounds of this invention include those of (A) in which:

(B). $R_1$ is alkyl of 1–6 carbon atoms, alkenyl of 2–7 carbon atoms, cycloalkyl of 3–8 carbon atoms, or cycloalkenyl of 4–8 carbon atoms;

$R_2$ is hydrogen, alkyl of 1–6 carbon atoms, halogen, or hydroxy;

$R_9$ is alkyl of 1–6 carbon atoms, halogen, trifluoromethyl, —$CO_2R_{11}$, aryl of 6–20 carbon atoms, arylalkyl of 7–26 carbon atoms, or a saturated, unsaturated, or partially unsaturated heterocyclic ring or ring system of 4–14 atoms, containing 1–4 heteroatoms selected from N, O, and S;

$R_{10}$ is hydrogen, where the remaining substituents are as defined above.

Preferred compounds of this invention include those of (B) in which:

(C). $R_1$ is alkyl of 1–6 carbon atoms or alkenyl of 2–7 carbon atoms;

$R_9$ is alkyl of 1–6 carbon atoms, halogen, or trifluoromethyl, where the remaining substituents are as defined above.

This invention also provides a process for preparing a compound of formula I or II or a pharmaceutically acceptable salt thereof which comprises one of the following:

a) deprotecting a compound of formula IV or V:

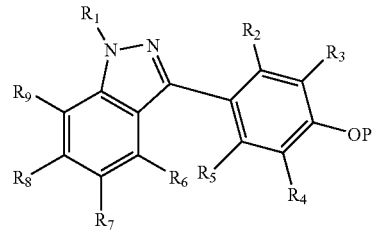

IV

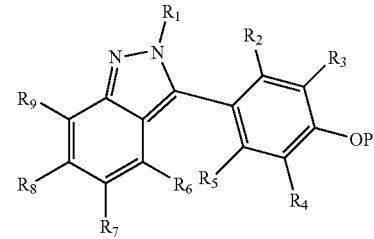

V wherein $R_{1-9}$ are as defined herein and P is a hydroxy protecting group, e.g., methyl, benzyl or t-butyldiphenylsilyl; to give a corresponding compound of formula I or II wherein $R_{10}$ is hydrogen;

or b) acylating a compound of formula XI or XII

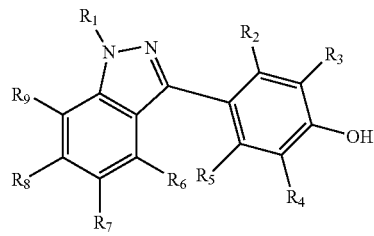

XI

-continued

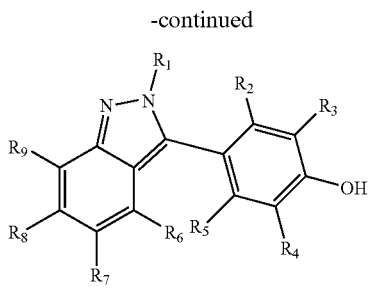
XII wherein R$_{1-9}$ are as defined herein, with a compound of formula HalCOR$_{11}$ wherein R$_{11}$ is as defined herein to give a compound of formula I or II where R$_{10}$ is —COR$_{11}$;

or c) reacting a compound of formula XI or XII as defined above with a compound of formula HOCO(CH$_2$)$_n$CH(NHR$_{12}$)CO$_2$R$_{11}$ wherein n, R$_{11}$ and R$_{12}$ are as defined herein in the presence of a coupling or activating agent to give a compound of formula I or II where R$_{10}$ is —CO(CH$_2$)$_n$CH(NHR$_{12}$)CO$_2$R$_{11}$;

or d) reacting a compound of formula XI or XII as defined above with a compound of formula

R$_{11}$NCO wherein R$_{11}$ is as defined herein, to give a compound of formula I or II where R$_{10}$ is —CONHR$_{11}$;

or e) reacting a compound of formula XI or XII as defined above with a dichlorophosphate of formula R$_{11}$O—P(=O)Cl$_2$ wherein R$_{11}$ is as defined herein, to give a compound of formula I or II where R$_{10}$ is —P(=O)(OH)OR$_{11}$;

or f) reacting a compound of formula

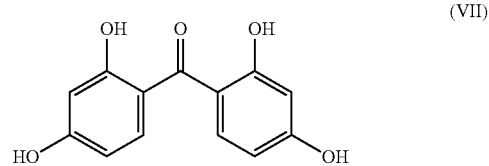
(VII)

with a hydrazine salt of formula R$_1$NHNH$_2$ wherein R$_1$ is as defined herein to give a corresponding compound of formula I wherein R$_2$ and R$_8$ are OH, and R$_3$, R$_4$, R$_5$, R$_6$, R$_7$, and R$_9$ are hydrogen;

or g) converting a basic compound of formula (I) or (II) to a pharmaceutically acceptable salt or vice versa;

or h) converting an acidic compound of formula (I) or (II) to a pharmaceutically acceptable salt or vice versa.

The reagents used in the preparation of the compounds of this invention can be either commercially obtained or can be prepared by standard procedures described in the literature. Compounds of formula I and formula II wherein R$_{10}$=H can be prepared from a common precursor of formula III as outlined in scheme 1.

Scheme 1

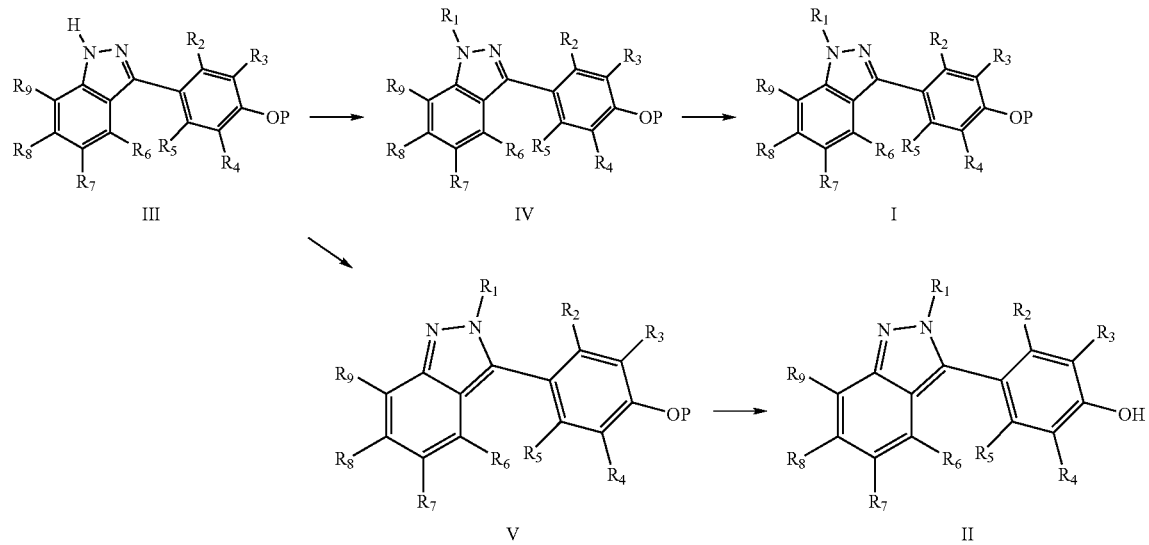

where
R$_1$=alkyl, cycloalkyl, alkenyl, cycloalkenyl, arylalkyl;
R$_2$, R$_3$, R$_4$, R$_5$, R$_6$, R$_7$, R$_8$, R$_9$ are as previously defined.
P is a phenol protecting group, preferably but not limited to methyl, benzyl or t-butyldiphenylsilyl.

Thus, compounds of formula III are treated with sodium hydride in a suitable solvent such as 4-dimethylaminopyridine (DMAP). When the gas evolution ceases, the alkyl halide is added and the solution is heated at 50° C. overnight. The reaction is partitioned with ethyl acetate and water. The organic phase is dried with a suitable drying agent such as sodium sulfate (Na$_2$SO$_4$). The crude products IV and V are isolated as a single residue after filtration and concentration of the organic layer in vacuo. Separation is easily carried out by chromatography known to one skilled in the art, to provide the separated intermediates IV and V.

Compounds of formula I and formula II are prepared from IV or V respectively by a deprotection step.

When P=benzyl, deprotection to the phenol is accomplished by hydrogenation over 10% palladium on carbon using either hydrogen gas, or catalytic hydride transfer with cyclohexene or ammonium formate.

When P=methyl, deprotection is carried out using BBr$_3$ with cyclohexene as a scavenger for HBr.

When P=t-butyldiphenylsilyl, deprotection can be accomplished with tetrabutylammonium fluoride.

Compounds of formula IV can also be prepared as outlined in scheme 2 from compounds of formula VI.

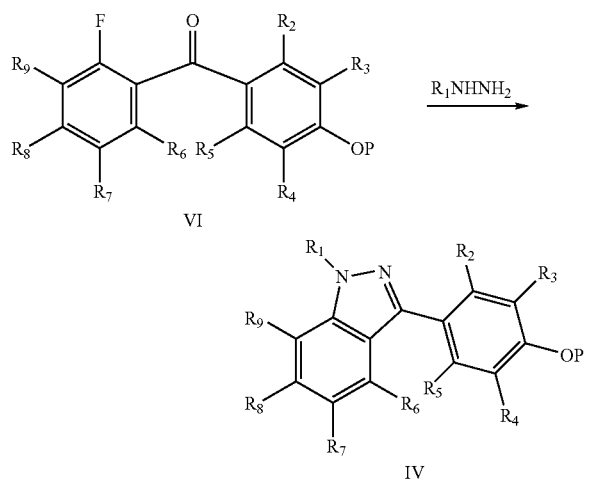

Reaction of 2-fluorobenzophenones of compound VI can be reacted directly with optimally substituted hydrazines where R$_1$=alkyl or aryl which are either commercially available or readily prepared by common procedures known to those skilled in the art. Thus, a mixture of the benzophenones of compound VI are combined with the hydrazines in a suitable solvent such as methanol in the presence of ethyl acetate. The intermediate hydrazone either spontaneously cyclizes to the compounds of formula IV or can be isolated by concentration of the reaction mixture. The isolated hydrazone is heated neat to temperatures of up to 190° C. The residues are purified by chromatography to provide compounds of formula IV.

Compounds of formula I, wherein R$_2$ and R$_8$ are OH and R$_3$, R$_4$, R$_5$, R$_6$, R$_7$, and R$_9$ are hydrogen, can also be prepared by a similar process from commercially available 2-2'-4-4'-tetrahydrobenzophenone according to the literature preparation of R. Krishnan, S. A. Lang, Y. I. Lin, R. G. Wilkinson *J. Heterocycl. Chem*, 1988, 25, 447 and outlined in Scheme 3.

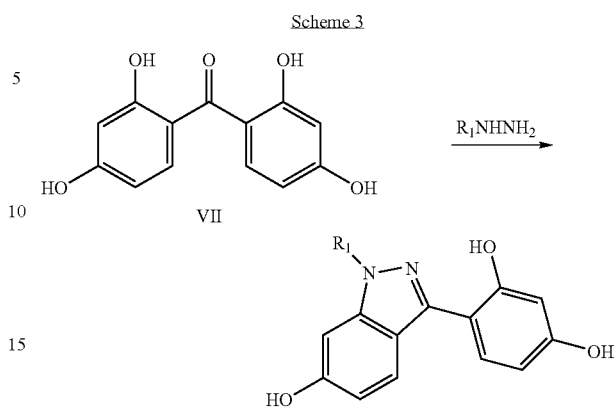

Thus, a solution of the substituted hydrazine salt (1 to 2 equivalents), sodium acetate (1 to 4 equivalents) and 2,2', 4,4'-tetrahydroxybenzophenone (1 equivalent) in an appropriate solvent such as methanol (0.2 molar solution) is stirred at ambient temperature overnight. The reaction mixture is concentrated in vacuo and the residues partitioned with EtOAc and H$_2$O. The organic phase is dried (Na$_2$SO$_4$) and concentrated in vacuo to give the intermediate hydrazone. The residues are heated at 190° C. overnight. Product residues are purified by chromatography.

Compounds of formula III are readily prepared from compounds of formula VI as shown in Scheme 4.

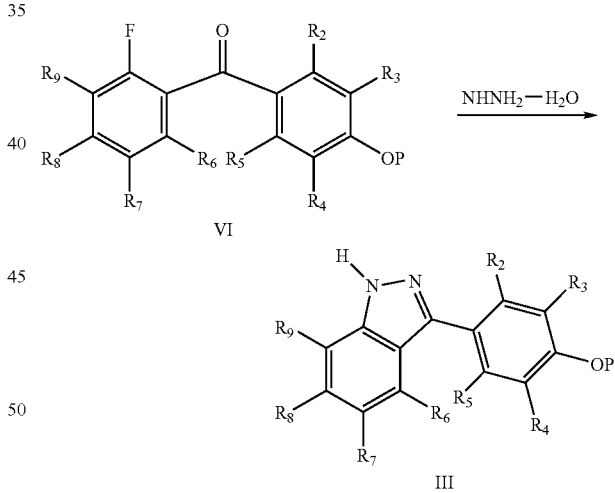

Thus, an appropriately substituted compound of formula VI is reacted with an excess of hydrazine hydrate in pyridine containing DMAP. The reaction is heated at 100° C. for at least 24 hours. The reaction is concentrated in vacuo and the residue is partitioned with ethyl acetate and 1 N HCl. The organic phase is washed with brine and dried with a drying agent such as Na$_2$SO$_4$. The solvent is evaporated to provide the compounds of formula III.

Compounds of formula VI are readily prepared as outlined in scheme 5 from the reaction of an appropriately substituted 2-fluoro-N-methoxy-N-methyl-benzamide of formula VII.

Scheme 5

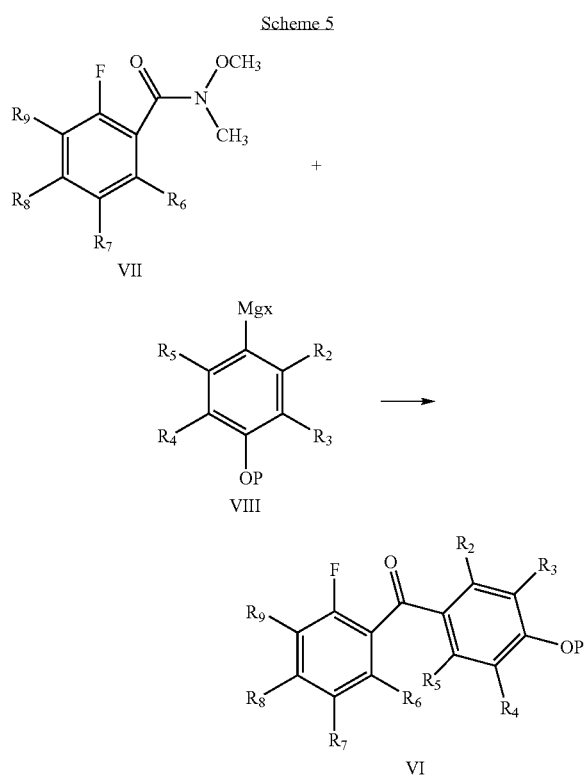

where X is preferably but not limited to Br.

Thus, reaction of compounds of formula VII with compounds of formula VIII, which are either commercially available or readily prepared by one skilled in the art, in a suitable solvent such as tetrahydrofuran (THF).

The Weinreb amides of formula VII are generated by the reaction of an appropiately substituted 2-fluorobenzoic acid with N,O-dimethylhydroxylamine and N,N-carbonyldiimidazole in a suitable solvent such as DMF (Robertson et. al., *J. Med. Chem.*, 1990, 33, 3167) or from the acid chloride prepared from reaction of the benzoic acid with oxalyl chloride in a suitable solvent such as THF in the presence of a base such as N,N-diisopropylethylamine.

Compounds of formula IV can also be prepared as outlined in Scheme 6

Scheme 6

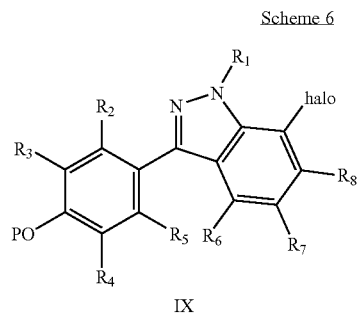

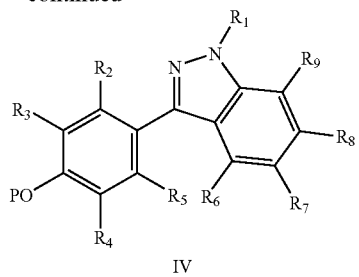

where
$R_1$, $R_2$, $R_3$, and $R_4$ are as defined above;
and halo=Cl or Br

Thus, when halo=Br, compounds of formula IV where $R_9$=aryl, heteroaryl, heterocycle, and alkenyl, can be prepared by the Suzuki coupling of IX with an appropriately substituted boronic acid in a suitable solvent such as dioxane, in the presence of an aqueous base such as potassium carbonate, in the presence of 1 to 5 mol % of palladium catalyst such as tetrakis(triphenylphoshine)palladium (0). The mixture is typically heated at 80° C. for a period of 1 to 24 hours (see Miyaura, N. Suzuki, A., *Chem Rev.*, 1995, 95, 2457). The compounds are obtained in pure forms by chromatography known to those skilled in the art.

When halo=Cl, compounds of formula IV where $R_9$=aryl, hetroaryl, heterocyclic can be prepared as described by Huang J. and Nolan S. P., et al, *J. Am. Chem Soc.*, 1999, 121, 9889. Thus, reaction of IX with a suitably substituted aryl magnesium bromide in a suitable solvent such as dioxane in the presence of an N-heterocyclic carbene ligand and a palladium catalyst such as but not limited to palladium(II) acetate.

Compounds of formula V can be prepared as outlined in Scheme 7.

Scheme 7

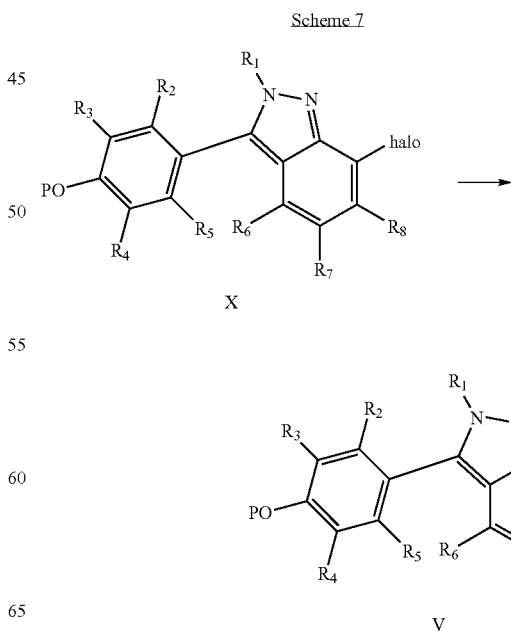

where
R$_1$, R$_2$, R$_3$, and R$_4$ are as defined above;
and halo=Cl or Br.

Thus, compounds of formula V where R$_9$=aryl, heteroaryl, heterocyclic, and alkenyl, can be prepared in an analogous fashion to the regioisomer described above in Scheme 6.

Prodrugs of formula I and formula II can readily be prepared as described below.

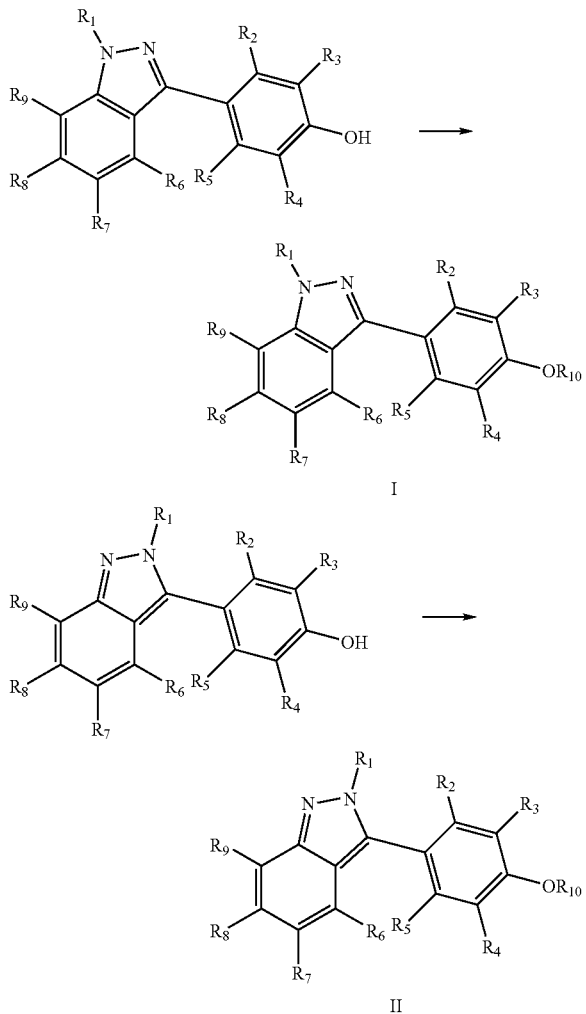

Thus when R$_{10}$=COR$_{11}$, compounds can be prepared by methods commonly known to those skilled in the art. The reaction of an acid chloride with compounds of formula I and formula II wherein R$_1$=H in a suitable solvent such as methylene chloride in the presence of a suitable base such as N,N-diisopropylethylamine affords the ester prodrugs.

For amino acid esters, standard coupling techniques known to those skilled in the art can be used, including activation of the carboxylic acid in the presence of DMAP (Boden E. P., Keck, G. E., *J. Org. Chem*, 1985, 50, 2394). A solution of compounds of formulas I and II dicyclohexylcarbodiimide and DMAP in a suitable solvent such as CH$_2$Cl$_2$ is stirred overnight at ambient temperature. The reaction mixture is purified typically by column chromatography known to those skilled in the art to provide the ester.

When R$_{10}$=CONHR$_{11}$, compounds of formula I and II are reacted with substituted isocyanates in a suitable solvent such as dioxane and heated at 80° C. for up to 48 hours. (*March's Adv. Org. Chem*, 5$^{th}$ ed, 16: 1183, Wiley Interscience, 2001).

When R$_{10}$=P(=O)(OH)OR$_{11}$, the substituted hydrogen phosphates of compounds of formulas I and II can be prepared as described by Rodriguez, M. J. et al., *Bioorg. Med. Chem. Lett.*, 1999, 9, 1863. Thus, a solution of compounds of formulas I or II, wherein R$_{10}$=H substituted dichlorophosphate and lithium hexamethyldisilazide in a suitable solvent such as THF is stirred for 1 hour at ambient temperature. The reaction mixture is quenched with H$_2$O and purified by reversed phase HPLC, known by one skilled in the art.

The compounds of this invention are useful in the treatment of the inflammatory component of diseases and are therefore particularly useful in treating atherosclerosis, myocardial infarction, congestive heart failure, arthritis, inflammatory bowel disease, type II diabetes, osteoarthritis, asthma and any other autoimmune disease in humans or other mammals which comprises administering to a human or other mammal an antiinflammatory effective amount of a compound of the present invention.

Representative compounds of this invention were evaluated in the following standard pharmacological test procedures which demonstrated the antiinflammatory activity for the compounds of this invention. The test procedures used and the results obtained are briefly described below.

Test Procedures:

Cells

T-175 flasks of 100% confluent HAECT-1 cells (immortalized human aortic endothelial cells) were washed with 8 ml of HBSS (HEPES buffered saline solution) and infected for four hours with 6 ml of a 1:10 dilution of Ad5-wt-hERα virus (an adenovirus transfection vector that mediates CMV promoter driven expression of human ERα) in phenol red free Endothelial Cell Basal medium (Clonetics, San Diego Calif., Catalog # CC-3129) containing 0.25% bovine serum albumin (EBM-BSA). After four hours, cells were washed with EBM-BSA and incubated overnight in the same medium. Following overnight incubation, cells were washed with EBM-BSA and infected for 2 hours with 6 ml of a 1:10 dilution of Ad5-3×(NFκB).Luc virus (Adenovirus luciferase expression vector driven by 3 repeats of the MHC NFκb site 5' to the thymidine kinase promoter) in EBM-BSA. After two hours, cells were washed and incubated at 34° C. for 1 hour. Cells were then washed, trypsinized, counted and resuspended in 95% FBS/5% dimethylsulfoxide at a concentration of 4×10$^6$ cells/ml, frozen as 1 or 5 ml aliquots in cryo-vials and stored at −150° C. Control (no ER infection) cells were processed as above without Ad5-wt-hERα virus infection.

IL-6 and Creatine Kinase Assays

ERα infected HAECT-1 cells or control cells were thawed, diluted 42× in warm EBM-BSA, plated into 96-well plates at 0.1 ml/well and incubated for 4 h at 34° C. Test compounds were added to the cells as 2× stocks in EBM-BSA containing 2 ng/ml IL-1β (R&D Systems) and plates were returned to the incubator (34° C.). After 15–20 h, 100 μl aliquots of media were removed from the cells and assayed for IL-6 content using a BioSource human IL-6 ELISA Kit. Cells were subsequently washed with 300 μl of Dulbecco's phosphate buffered saline and lysed in 50 μl of Cell Culture Lysis Reagent (Promega). Luciferase was determined on a Wallac Victor² Luminometer (Gaithersburg, Md.) using 10 μl of lysate and mixing with 100 μl of Promega Luciferase Assay reagent. Creatine kinase was determined from the rate of increase in $A_{340}$ following addition of 100 μl of CK assay reagent (Sigma, cat. No 47-10) to the remainder of the cell lysate.

Data Analyses

For $IC_{50}$ and $EC_{50}$ calculations, mean IL-6, luciferase or CK values versus $\log_{10}$ of the compound concentration were fitted to a four parameter logistic equation. The $IC_{50}/EC_{50}$ value, 'Hill slope', upper and lower limits of the curve were iteratively estimated.

Mice

Ovariectomized C57BL/6 mice (16–20 g) (Taconic) were separated into groups of 8. After 5–7 days of recuperation, the mice were fed a chow diet or an atherogenic diet (15.75% fat, 1.25% cholesterol and 0.5% sodium cholate) (Purina diet #21539). EE or test compound was administered once daily by gavage in a methylcellulose/tween vehicle (0.1 ml per mouse) for 5 weeks. At the end of the experimental period, the liver was collected and uterine wet weight was recorded.

RNA Analysis

Liver total RNA was prepared by using Trizol reagent (BRL). Estrogen and compound regulation of NF-κB target genes were verified by real time RT-PCR using an ABI PRISM 7700 Sequence Detection System according to the manufacturer's protocol (Applied Biosystems). The data was analyzed using the Sequence Detector v1.7 software (Applied Biosystems) and normalized to GAPDH using the Applied Biosystems primer set.

The following table summarizes the results obtained in the standard pharmacological test procedures described above.

TABLE 1

Effects of 17-β-estradiol on NE-κB, IL-6 and CK expression in Ad5-wt-ER infected HAECT-1 cells

| Example # | ER/NF-KB-luc IC₅₀ (nM) | % E2 | ER/IL-6 IC₅₀ (nM) | % E2 | ER/CK EC₅₀ (nM) | % E2 |
|---|---|---|---|---|---|---|
| 1 | 62 | 74 | 3318 | 101 | 1217 | 33 |
| 2 | 112 | 49 | 1137 | 67 | 549 | 29 |
| 4 | 443 | 63 | 15775 | 58 | | |
| 5 | 165 | 71 | | | 4790 | 66 |
| 6 | 86 | 85 | 478 | 43 | | |
| 7 | 90 | 92 | 246 | 77 | 1827 | 54 |
| 11 | 60 | 54 | 2317 | 91 | 114 | 26 |
| 12 | 208 | 61 | 7606 | 73 | 1199 | 58 |
| 13 | 133 | 97 | 601 | 83 | 828 | 47 |
| 14 | 53 | 73 | 761 | 67 | | |
| 15 | 164 | 94 | 8127 | 110 | | |
| 16 | 95 | 79 | 81 | 58 | 438 | 45 |
| 17 | 305 | 71 | 701 | 114 | 3070 | 97 |
| 20 | 149 | 69 | | | | |
| 21 | 140 | 73 | | | | |
| 22 | 50 | 73 | | | | |
| 23 | 239 | 76 | | | 72 | 55 |
| 24 | 63 | 83 | | | | |
| 25 | 274 | 112 | | | | |
| 26 | 356 | 101 | | | | |
| 27 | 1027 | 96 | | | | |
| 28 | 551 | 86 | | | | |
| 30 | 37 | 105 | | | | |
| 31 | 636 | 120 | | | | |
| 32 | 65 | 91 | | | | |
| 33 | 37 | 92 | | | 51 | 34 |
| 34 | 66 | 115 | | | 137 | 87 |
| 37 | 40 | 95 | | | 303 | 61 |
| 38 | | 89 | | | 25 | 70 |

TABLE 1-continued

Effects of 17-β-estradiol on NE-κB, IL-6 and CK expression in Ad5-wt-ER infected HAECT-1 cells

| Example # | ER/NF-KB-luc IC₅₀ (nM) | % E2 | ER/IL-6 IC₅₀ (nM) | % E2 | ER/CK EC₅₀ (nM) | % E2 |
|---|---|---|---|---|---|---|
| 39 | 9 | 89 | | | 57 | 46 |
| 40 | | 108 | | | 22 | 79 |
| 41 | 95 | 85 | | | 415 | 39 |
| 42 | 190 | 102 | | | | |
| 43 | 51 | 79 | | | 138 | 34 |
| 44 | 43 | 90 | | | 309 | 48 |
| 45 | 31 | 86 | | | 121 | 43 |
| 46 | | 102 | | | | 67 |
| 47 | 97 | 94 | | | 13 | 26 |
| 48 | 42 | 107 | | | 79 | 49 |
| 49 | 3 | 91 | | | 10 | 44 |
| 50 | 106 | 84 | | | 327 | 43 |
| 51 | 18 | 94 | | | 46 | 37 |
| 52 | 17 | 76 | | | 111 | 27 |
| 53 | 58 | 84 | | | 184 | 31 |
| 54 | 393 | 77 | | | | |
| 55 | 26 | 90 | | | 401 | 49 |
| 56 | 14 | 96 | | | 477 | 47 |
| 57 | 45 | 89 | | | 205 | 45 |
| 58 | 20 | 100 | | | 97 | 38 |
| 59 | 5 | 90 | | | 133 | 36 |
| 60 | 20 | 76 | 13 | 90 | 331 | 34 |
| 61 | 50 | 62 | | | 76 | 33 |
| 62 | 47 | 82 | | | 253 | 30 |
| 63 | 1883 | 158 | | | | |
| 64 | 100 | 81 | 114 | 94 | 198 | 18 |
| 65 | 41 | 86 | | | 218 | 42 |
| 66 | 29 | 56 | | | 17 | 32 |
| 67 | 48 | 65 | | | | |
| 68 | 56 | 74 | | | | |
| 69 | 235 | 68 | | | 704 | 32 |
| 70 | 14 | 76 | | | | |
| 72 | 7 | 85 | | | 140 | 46 |
| 73 | 94 | 76 | | | 103 | 19 |
| 74 | 59 | 86 | | | | 26 |
| 75 | 63 | 83 | | | 982 | 48 |
| 76 | 22 | 86 | | | 57 | 20 |
| 77 | 41 | 87 | | | 302 | 29 |
| 78 | 590 | 90 | | | 2197 | 32 |
| 79 | 92 | 93 | | | 734 | 52 |
| 80 | 18 | 48 | | | | |
| 81 | 33 | 92 | | | 308 | 62 |
| 82 | 191 | 68 | | | | |
| 83 | 20 | 82 | | | | |
| 84 | 36 | 75 | | | | |
| 85 | 235 | 46 | | | | |
| 86 | 255 | 83 | | | 413 | 27 |
| 87 | 347 | 77 | | | 188 | 24 |
| 88 | 419 | 74 | | | | |
| 89 | 435 | 97 | | | | |
| 91 | 80 | 82 | | | 787 | 24 |
| 92 | 228 | 87 | | | | |
| 93 | 128 | 60 | | | | |
| 94 | 332 | 86 | | | | |
| 96 | 88 | 78 | | | | |
| 101 | 505 | 61 | | | | |
| 103 | 138 | 79 | | | | |
| 104 | 250 | 81 | | | | |
| 105 | 918 | 66 | | | | |
| 110 | 2 | 89 | | | 12 | 82 |
| 111 | 214 | 78 | | | | |
| 112 | 667 | 48 | | | | |
| 114 | 268 | 67 | | | | |
| 115 | 246 | 71 | | | | |
| 115 | 27 | 82 | | | 166 | 91 |
| 116 | 140 | 63 | | | 229 | 25 |
| 117 | 150 | 52 | | | 169 | 22 |
| 118 | 418 | 66 | | | | |
| 122 | 350 | 78 | | | | |
| 123 | 328 | 71 | | | | |
| 125 | 479 | 128 | | | | |
| 126 | 134 | 85 | 122 | 52 | 387 | 52 |

TABLE 1-continued

Effects of 17-β-estradiol on NF-κB, IL-6 and CK expression in Ad5-wt-ER infected HAECT-1 cells

| Example # | ER/NF-KB-luc IC₅₀ (nM) | % E2 | ER/IL-6 IC₅₀ (nM) | % E2 | ER/CK EC₅₀ (nM) | % E2 |
|---|---|---|---|---|---|---|
| 130 | 62 | 97 | | | 205 | 54 |
| 131 | 195 | 82 | 380 | 72 | 815 | 65 |
| 134 | 897 | 76 | | | 1927 | 36 |
| 139 | 183 | 67 | 329 | 40 | 722 | 36 |
| 142 | 114 | 69 | 65 | 60 | 390 | 47 |
| 143 | 310 | 65 | | | | |
| 145 | 125 | 66 | 97 | 60 | 439 | 48 |
| 147 | 166 | 65 | | | 431 | 29 |
| 149 | 319 | 67 | 115 | 49 | 527 | 30 |
| 151 | 1061 | 81 | | | | |
| 158 | 515 | 106 | | | 1124 | 59 |
| 162 | 113 | 84 | 107 | 34 | | |
| 167 | 311 | 83 | | | 588 | 29 |
| 168 | 347 | 95 | | | 1374 | 86 |
| 169 | 65 | 69 | 65 | 65 | 364 | 38 |
| 170 | 276 | 77 | | | 827 | 28 |
| 171 | 582 | 95 | | | 2382 | 42 |
| 172 | 349 | 95 | | | 1325 | 92 |
| 176 | 587 | 111 | | | 1041 | 70 |
| 180 | 28 | 88 | | | 156 | 50 |
| 182 | 443 | 121 | | | 2935 | 71 |
| 183 | 431 | 135 | | | 2935 | 48 |
| 188 | 751 | 90 | | | 2453 | 31 |
| 192 | 371 | 87 | | | 608 | 51 |
| 198 | 303 | 100 | | | 1000 | 30 |
| 199 | 487 | 100 | | | 1260 | 42 |
| 200 | 435 | 86 | | | 1478 | 58 |
| 202 | 539 | 160 | | | 1839 | 68 |
| 203 | 196 | 117 | | | 1068 | 48 |
| 206 | 473 | 84 | | | 902 | 27 |
| 219 | 369 | 104 | | | | |
| 220 | 112 | 84 | | | 2341 | 48 |
| 226 | 32 | 87 | | | 309 | 20 |
| 227 | 56 | 70 | | | 279 | 21 |
| 228 | 75 | 83 | | | | |
| 230 | 367 | 82 | | | | |
| 231 | 382 | 78 | | | 3254 | 32 |
| 232 | 143 | 75 | | | | |
| 233 | 87 | 81 | | | | |
| 234 | 34 | 72 | | | | |
| 235 | 16 | 74 | | | 223 | 35 |
| 236 | 47 | 83 | | | 112 | 36 |
| 237 | 480 | 79 | | | | |
| 238 | 11 | 74 | | | | |
| 240 | 158 | 54 | | | 974 | 32 |
| 241 | 32 | 60 | | | | |
| 243 | 142 | 83 | | | | |
| 244 | 33 | 48 | | | 208 | 33 |
| 245 | 16 | 70 | | | | |
| 246 | 11 | 82 | | | 136 | 28 |
| 247 | 12 | 70 | | | 17 | 42 |
| 248 | 481 | 73 | | | | |
| 249 | 59 | 59 | | | | |
| 250 | 47 | 80 | | | | |
| 251 | 24 | 57 | | | | |
| 252 | 56 | 59 | | | | |
| 253 | 21 | 62 | | | | |
| 254 | 27 | 56 | | | | |
| 255 | 4 | 89 | | | | |
| 256 | 13 | 94 | | | 292 | 32 |
| 257 | 43 | 76 | | | 490 | 27 |
| 258 | 644 | 77 | | | | |
| 259 | 18 | 73 | | | 143 | 38 |
| 260 | 28 | 53 | | | | |
| 261 | 98 | 42 | | | | |
| 262 | 8 | 75 | | | | |
| 263 | 30 | 84 | | | 165 | 17 |
| 264 | 15 | 74 | | | 15 | 21 |
| 265 | 6 | 82 | | | 138 | 28 |
| 266 | 68 | 77 | | | 213 | 35 |
| 267 | 53 | 64 | | | 250 | 35 |

Efficacy values are relative to the maximal inhibition (NF-κB or IL-6 test procedure) or stimulation (CK test procedure) observed with E2

E2 inhibits NF-κB and IL-6 expression in Ad5-wt-ER infected HAECT-1 cells with an IC$_{50}$ value around 1 nM and induces expression of creatine kinase in the same cells with similar potency (5.8 nM) (Table 1). In contrast, compounds of the present invention potently and efficaciously inhibit NF-κB and IL-6 expression in Ad5-wt-ER infected HAECT-1 cells but do not induce CK expression (Table 1) in an ER-dependent manner. The ability of compounds of the present invention to inhibit NF-κB and IL-6 expression without inducing CK activity (Table 1) is demonstrates anti-inflammatory activity in the absence of classic estrogenic activity.

Based on the results obtained in the standard pharmacological test procedures, the compounds of this invention are selective antiinflammatory compounds described herein useful for the treatment and prevention of chronic inflammatory diseases without stimulating uterine and breast cell proliferation as found with classic estrogens.

Accordingly, the compounds of this invention are useful in treating or inhibiting osteoporosis and in the inhibition of bone demineralization, which may result from an imbalance in an individual's formation of new bone tissues and the resorption of older tissues, leading to a net loss of bone. Such bone depletion results in a range of individuals, particularly in post-menopausal women, women who have undergone bilateral oophorectomy, those receiving or who have received extended corticosteroid therapies, those experiencing gonadal dysgenesis, and those suffering from Cushing's syndrome. Special needs for bone, including teeth and oral bone, replacement can also be addressed using these compounds in individuals with bone fractures, defective bone structures, and those receiving bone-related surgeries and/or the implantation of prosthesis. In addition to those problems described above, these compounds can be used in treatment or inhibition for osteoarthritis, hypocalcemia, hypercalcemia, Paget's disease, osteomalacia, osteohalisteresis, multiple myeloma and other forms of cancer having deleterious effects on bone tissues.

The compounds of this invention are also active in the brain and are therefore useful for inhibiting or treating Alzheimer's disease, cognitive decline, decreased libido, senile dementia, neurodegenerative disorders, stroke, depression, anxiety, insomnia, schizophrenia, and infertility. The compounds of this invention are also useful in treating or inhibiting benign or malignant abnormal tissue growth including, glomerulosclerosis, prostatic hypertrophy, uterine leiomyomas, breast cancer, scleroderma, fibromatosis, endometriosis, endometrial cancer, polycystic ovary syndrome, endometrial polyps, benign breast disease, adenomyosis, ovarian cancer, melanoma, prostate cancer, cancers of the colon, CNS cancers, such as glioma or astioblastomia.

The compounds of this invention are cardioprotective and are antioxidants, and are useful in lowering cholesterol, triglycerides, Lp(a), and LDL levels; inhibiting or treating hypercholesteremia, hyperlipidemia, cardiovascular disease, atherosclerosis, acute coronary syndrome, peripheral vascular disease, restenosis, and vasospasm, and inhibiting vascular wall damage from cellular events leading toward immune mediated vascular damage.

The compounds of this invention are also useful in treating disorders associated with inflammation or autoimmune diseases, including inflammatory bowel disease (Crohn's disease, ulcerative colitis, indeterminate colitis), arthritis (rheumatoid arthritis, spondyloarthropathies, osteoarthritis, psoriatic arthritis, or juvenile arthritis), pleurisy, ischemia/reperfusion injury (e.g. stroke, transplant rejection, myocardial infarction, etc.), asthma, chronic obstructive pulmonary disease, giant cell arteritis, prostatitis, uveitis, psoriasis, multiple sclerosis, systemic lupus erythematosus and sepsis.

The compounds of this invention are also useful in treating or inhibiting ocular disorders including cataracts, uveitis, and macular degeneration and in treating skin conditions such as aging, alopecia, and acne.

The compounds of this invention are also useful in treating or inhibiting metabolic disorders such as type-II diabetes, of lipid metabolism, appetite (e.g. anorexia nervosa and bulimia).

Compounds in this invention are also useful in treating or inhibiting bleeding disorders such as hereditary hemorrhagic telangiectasia, dysfunctional uterine bleeding, and combating hemorrhagic shock. The compounds of this invention are useful in disease states where amenorrhea is advantageous, such as leukemia, endometrial ablations, chronic renal or hepatic disease or coagulation diseases or disorders.

The following describes the preparation of representative compounds of this invention.

GENERAL METHODS

Intermediates 1–15

Method A: Substituted
(2-Fluoro-phenyl)-(4-methoxyphenyl)-methanone

Step A
Substituted-N-Methoxy-N-methyl-2-fluorobenzamide

A mixture of the substituted benzoic acid (1 equivalent) and oxalyl chloride (1 equivalent) in dry $CH_2Cl_2$ was treated with a catalytic amount of DMF. The reaction mixture was stirred until gas evolution ceased. To the cooled solution was added N,O-dimethylhydroxylamine hydrochloride (1.2 equivalents) in one portion. Pyridine (0.24 mL/mmol) was added dropwise and the mixture was stirred at ambient temperature overnight. The reaction mixture was concentrated in vacuo and the residue partitioned with EtOAc and 1 N HCl. The organic phase was washed with saturated aqueous $NaHCO_3$ and brine. The organic phase was dried ($Na_2SO_4$) and concentrated in vacuo to provide reasonably pure intermediate substituted-N-methoxy-N-methyl-2-fluorobenzamide.

Step B Substituted-(2-Fluoro-phenyl)-(4-methoxyphenyl)-methanone

A solution of substituted-N-Methoxy-N-methyl-2-fluorobenzamide (1 equivalent) in THF (0.5 molar) was treated with 1.2 equivalents of substituted-4-methoxyphenyl magnesium bromide (0.5M). The mixture was heated at 50° C. overnight. The reaction mixture was partitioned with EtOAc and 1N HCl. The organic phase was washed with brine and dried ($Na_2SO_4$). The residue obtained on concentration in vacuo was purified by flash chromatography (hexane-ethyl acetate) to give the title compound.

Intermediate 1

(2-Fluoro-3-trifluoromethylphenyl)-(4-methoxyphenyl)-methanone

Step 1: 2-fluoro-N-methoxy-N-methyl-3-(trifluoromethyl)benzamide

Prepared according to Method A step A from 2-fluoro-3-trifluoromethylbenzoic acid (5.0 g, 24 mmol), N,O-dimethylhydroxylamine hydrochloride (3.4 g, 35 mmol), oxalyl chloride (2.18 mL, 25 mmol) and 6 mL of pyridine to give the title compound (6.0 g) as an oil. Used as is in the next prep $^1$H NMR (DMSO-$d_6$): δ 3.28 (s, 3H), 3.475 (s, 3H), 7.499 (t, 1H), 7.86 (m, 2H).

MS (EI) m/z: 251 M$^+$

Step 2: (2-Fluoro-3-trifluoromethylphenyl)-(4-methoxyphenyl)-methanone

Prepared according to Method A step B from 2-fluoro-N-methoxy-N-methyl-3-(trifluoromethyl)benzamide (2.5 g, 10 mmol) and 4-methoxyphenylmagnesium bromide (20 mL, 0.5 M in THF) to give 2.1 g of the title compound as a white solid.

$^1$H NMR (DMSO-$d_6$): δ 3.86 (s, 3H), 7.10 (d, 2H), 7.56 (t, 1H), 7.76 (d, 2H), 7.87 (t, 1H), 8.008 (t, 1H).

MS (-APCI) m/z: 298 M$^-$

Intermediate 2

(3-chloro-2-fluorophenyl)-(4-methoxyphenyl)-methanone

Step 1:
3-chloro-2-fluoro-N-methoxy-N-methylbenzamide

Prepared according to Method A step A from 3-chloro-2-fluorobenzoic acid (3.0 g, 17.2 mmol), N,O-dimethylhydroxylamine hydrochloride (2.34 g, 24 mmol), oxalyl chloride (1.5 mL, 17.2 mmol) and 5 mL of pyridine to give the title compound (3.3 g) as an oil. Used as is in the next prep $^1$H NMR (DMSO-$d_6$): δ 3.3 (s, 3H), 3.45 (s, 3H), 7.3 (m, 1H), 7.45 (m, 1H), 7.68 (m, 1H).

Step 2: (3-chloro-2-fluorophenyl)-(4-methoxyphenyl)-methanone

Prepared according to Method A step B from 3-chloro-2-fluoro-N-methoxy-N-methylbenzamide (2.5 g, 11.5 mmol) and 4-methoxyphenylmagnesium bromide (25 mL, 0.5 M in THF) to give 0.3 g of the title compound as a white solid.

$^1$H NMR (DMSO-$d_6$): δ 3.85 (s, 3H), 7.09 (d, 2H), 7.38 (t, 1H), 7.49 (m, 1H), 7.75 (d, 2H), 7.81 (d, 1H).

MS (APCI) m/z: 264 M$^+$

Intermediate 3

(2,3-difluorophenyl)-(4-methoxyphenyl)-methanone

Step 1:
2,3-difluoro-N-methoxy-N-methylbenzamide

Prepared according to Method A step A from 2,3-difluorobenzoic acid (4.0 g, 25 mmol), N,O-dimethylhydroxylamine hydrochloride (3.4 g, 35 mmol), oxalyl chloride (2.2 mL, 25 mmol) and 6 mL of pyridine to give the title compound (4.7 g) as an oil. Used as is in the next preparation.

$^1$H NMR (DMSO-$d_6$, 300 MHz): δ 3.25 (s, 3H), 3.45 (s, 3H), 7.25 (m, 2H), 7.55 (m, 2H).

Step 2:
(2,3-difluorophenyl)-(4-methoxyphenyl)-methanone

Prepared according to Method A step B from 2,3-difluoro-N-methoxy-N-methylbenzamide (3.0 g, 15 mmol) and 4-methoxyphenylmagnesium bromide (35 mL, 0.5 M in THF) to give 1.44 g of the title compound as a white solid.

$^1$H NMR (DMSO-$d_6$, 300 MHz): δ 3.85 (s, 3H), 7.07 (d, 2H), 7.35 (m, 2H), 7.65 (m, 1H), 7.75 (d, 2H).

Intermediate 4

(2-Fluoro-3-methylphenyl)-(4-methoxyphenyl)-methanone

Step 1:
2-fluoro-N-methoxy-N,3-dimethylbenzamide

Prepared according to Method A step A from 2-fluoro-3-methylbenzoic acid (5.0 g, 32.5 mmol), N,O-dimethylhydroxylamine hydrochloride (8.4 g, 87 mmol), oxalyl chloride (2.83 mL, 32.5 mmol) and 8 mL of pyridine to give the title compound (4.8 g) as an oil. Used as is in the next prep $^1$H NMR (DMSO-$d_6$): δ 3.25 (s, 3H), 3.47 (s, 3H), 7.15 (t, 1H), 7.24 (m, 1H), 7.35 (m, 1H).

Step 2: (2-Fluoro-3-methylphenyl)-(4-methoxyphenyl)-methanone

Prepared according to Method A step 2-fluoro-N-methoxy-N,3-dimethylbenzamide (4.8 g, 24 mmol) and 4-methoxyphenylmagnesium bromide (50 mL, 0.5 M in THF) to give 3.7 g of the title compound as a white solid.

$^1$H NMR (DMSO-$d_6$): δ 2.28 (s, 3H), 3.84 (s, 3H), 7.07 (d, 2H), 7.22 (t, 1H), 7.29 (m, 1H), 7.49 (m,1H), 7.72 (d, 2H).

MS (APCI) m/z: 245 (M+H)$^+$

Intermediate 5

(2,3-Difluorophenyl)-(4-methoxy-3-methyl-phenyl)-methanone

Prepared according to Method A step B from 2,3-difluoro-N-methoxy-N-methyl-benzamide (2.5 g, 12.4 mmol) and 4-methoxy-3-methyl-phenylmagnesium bromide (26 mL, 0.5 M in THF) to give 0.97 g of the title compound as a white solid.

$^1$H NMR (DMSO-$d_6$): δ 2.185 (s, 3H), 3.887 (s, 3H), 7.08 (d, 1H), 7.34 (m, 2H), 7.64 (m, 3H).

MS (ESI) m/z: 263 (M+H)$^+$

Intermediate 6

(2,3-difluorophenyl)(4-methoxy-2-methylphenyl)methanone

Prepared according to Method A step B from 2,3-difluoro-N-methoxy-N-methyl-benzamide (3.77 g, 18.7 mmol) and 4-methoxy-2-methyl-phenylmagnesium bromide (49 mL, 0.5 M in THF) to give 1.45 g of the title compound as a white solid.

$^1$H NMR (DMSO-$d_6$): δ 2.47 (s, 3H), 3.82 (s, 3H), 6.82 (d, 1H), 6.95 (s, 1H) 7.28–7.38 (m, 3H), 7.62–7.67 (m, 1H).

MS (APCI) m/z 263 ([M+H]$^+$);

Anal. calcd for $C_{15}H_{12}F_2O_2$: C, 68.70; H, 4.61; Found: C, 68.83; H, 4.65.

Intermediate 7

3-chloro-2-fluorophenyl)(4-methoxy-2-methylphenyl)methanone

Prepared according to Method A step B from 2-fluoro-3-chloromethyl-N-methoxy-N-methylbenzamide (2.78 g, 12.8 mmol) and 4-methoxy-2-methyl-phenylmagnesium bromide (33 mL, 0.5 M in THF) to give 1.07 g of the title compound as a white solid.

$^1$H NMR (DMSO-$d_6$): δ 2.47 (s, 3H), 3.81 (s, 3H), 6.83 (d, 1H), 6.95 (s, 1H), 7.32–7.36 (m, 3H), 7.44 (t, 1H), 7.80 (t, 1H).

MS (APCI) m/z 279 ([M+H]$^+$);

Anal. calcd for $C_{15}H_{12}ClFO_2$.0.25; $H_2O$, C, 63.61; H, 4.45.

Found: C, 63.73; H, 4.08.

Intermediate 8

(2-fluoro-3-methylphenyl)(4-methoxy-2-methylphenyl)methanone

Prepared according to Method A step B from 2-fluoro-3-methyl-N-methoxy-N-methyl-benzamide (3.10 g, 15.7 mmol) and 4-methoxy-2-methyl-phenylmagnesium bromide (40 mL, 0.5 M in THF) to give 1.17 g of the title compound as a white solid.

$^1$H NMR (DMSO-$d_6$): δ 2.25 (s, 3H), 3.81 (s, 3H), 6.83 (d, 1H), 6.93 (s, 1H), 7.20–7.32 (m, 3H), 7.48 (t, 1 H).

MS (APCI) m/z 259 ([M+H]$^+$);

Anal. calcd for $C_{16}H_{15}FO_2$.0.25; $H_2O$, C, 73.13; H, 5.95;. Found: C, 72.88; H, 5.92.

Intermediate 9

[2-fluoro-3-(trifluoromethyl)phenyl](4-methoxy-2-methylphenyl)methanone

Prepared according to Method A step B from 2-fluoro-3-trifluoromethyl-N-methoxy-N-methylbenzamide (4.05 g, 16.1 mmol) and 2-methyl-4-methoxyphenylmagnesium bromide (42 mL, 0.5 M in THF) to give 1.76 g of the title compound as a white solid.

$^1$H NMR (DMSO-$d_6$): δ 2.50 (s, 3H), 3.82 (s, 3H), 6.86 (d, 1H), 6.98 (s, 1H), 7.37 (d, 1H), 7.55 (t, 1H), 7.84 (t, 1H), 7.99 (t, 1H).

MS (APCI) m/z 313 ([M+H]$^+$);

Intermediate 10

(2,4-dimethoxyphenyl)(2-fluoro-3-methylphenyl)methanone

Prepared according to Method A step B from 2-fluoro-3-methyl-N-methoxy-N-methyl-benzamide (2.84 g, 14.4 mmol) and 2,4-dimethoxyphenylmagnesium bromide (26 mL, 0.5 M in THF) to give 1.13 g of the title compound as a white solid.

$^1$H NMR (DMSO-d$_6$): δ 2.27 (s, 3H), 3.53 (s, 3H), 3.63 (s, 3H), 5.85–5.89 (m, 1H), 5.98–6.00 (m, 1H), 6.11–6.16 (m, 1H), 6.52 (t, 1H), 6.65–6.73 (m, 2H).

MS (APCI) m/z 275 ([M+H]$^+$);

Anal. calcd for C$_{16}$H$_{15}$FO$_3$: C, 70.06; H, 5.51; Found: C, 68.61; H, 5.93.

Intermediate 11

(2,4-dimethoxyphenyl)[2-fluoro-3-(trifluoromethyl)phenyl]methanone

Prepared according to Method A step B from 2-fluoro-3-trifluoromethyl-N-methoxy-N-methylbenzamide (4.42 g, 17.6 mmol) and 2,4-dimethoxyphenylmagnesium bromide (32 mL, 0.5 M in THF) to give 1.67 g of the title compound as a white solid.

mp 79–82 °C.;

$^1$H NMR (DMSO-d$_6$): δ 3.56 (s, 3H), 3.86 (s, 3H), 6.64–6.69 (m, 2H), 7.48 (t, 1H), 7.65 (t, 1H), 7.82 (t, 1H), 7.94 (t, 1H).

MS (ESI) m/z 329.1 (M+H)$^+$;

MS (ESI) m/z 679.16 (2M+H)$^+$;

Anal. calcd for C$_{16}$H$_{12}$F$_4$O$_3$: C, 58.54; H, 3.68; Found: C, 58.45; H, 4.05.

Intermediate 12

(3-chloro-2-fluorophenyl)(2,4-dimethoxyphenyl)methanone

Prepared according to Method A step B from 2-fluoro-3-chloro-N-methoxy-N-methyl-benzamide (2.44 g, 11.2 mmol) and 2,4-dimethoxyphenylmagnesium bromide (20 mL, 0.5 M in THF) to give 0.95 g of the title compound as a white solid.

$^1$H NMR (DMSO-d$_6$): δ 3.59 (s, 3H), 3.85 (s, 3H), 6.65 (s, 2H), 7.30 (t, 1H), 7.42 (t, 1H), 7.59 (d, 1H), 7.73 (t, 1H)

MS (APCI) m/z 295 ([M+H]$^+$);

Anal. calcd for C$_{15}$H$_{12}$ClFO$_3$: C, 61.13; H, 4.10; Found: C, 61.25; H, 4.25.

Intermediate 13

(2,3-difluorophenyl)(2,4-dimethoxyphenyl)methanone

Prepared according to Method A step B from 2,3-difluoro-N-methoxy-N-methyl-benzamide (3.22 g, 16.0 mmol) and 2,4-dimethoxyphenylmagnesium bromide (29 mL, 0.5 M in THF) to give 1.21 g of the title compound as a white solid.

$^1$H NMR (DMSO-d$_6$): δ 3.60 (s, 3H), 3.86 (s, 3H), 6.65–6.68 (m, 2H), 7.27–7.29 (m, 2H), 7.55–7.64 (m, 2H).

MS (APCI) m/z 279 ([M+H]$^+$);

Anal. calcd for C$_{15}$H$_{12}$F$_2$O$_3$: C, 64.75; H, 4.35; Found: C, 64.51; H, 4.20.

Intermediate 14

(3-bromo-2-fluorophenyl)(4-methoxyphenyl)methanone

Prepared according to Method A step B from 2-fluoro-3-bromo-N-methoxy-N,3-dimethyl-benzamide (8.00 g, 30.5 mmol) and 4-methoxyphenylmagnesium bromide (65 mL, 0.5 M in THF) to give 3.12 g of the title compound as a white solid.

mp 88–90° C.;

$^1$H NMR (DMSO-d$_6$): δ 3.85 (s, 3H), 7.09 (d, 1H), 7.31 (t, 1H), 7.50–7.53 (m, 1H), 7.74 (d, 2H), 7.91–7.94 (m, 1H).

MS (ESI) m/z 309 ([M+H]$^+$);

Intermediate 15

(3-bromo-2-fluorophenyl)(4-methoxy-2-methylphenyl)methanone

Step 1: 3-bromo-2-fluoro-N-methoxy-N-methylbenzamide

Prepared according to Method A step A from 2-fluoro-3-bromomethylbenzoic acid (16.0 g, 73.0 mmol), N,O-dimethylhydroxylamine hydrochloride (3.4 g, 35 mmol), oxalyl chloride (6.69 mL, 76.7 mmol) and 25 mL of pyridine to give the title compound (8.0 g) as an oil. Used as is in the next step.

$^1$H NMR (DMSO-d$_6$, 500 MHz): δ 3.26 (s, 3H), 3.465 (s, 3H), 7.235 (t, 1H), 7.48 (t, 1H), 7.80 (t, 1H).

Step 2: (3-bromo-2-fluorophenyl)(4-methoxy-2-methylphenyl)methanone

Prepared according to Method A step B from 3-bromo-2-fluoro-N-methoxy-N-methylbenzamide (8 g, 31 mmol) and 2-methyl-4-methoxyphenyl magnesium bromide ((70 ml, 0.5 M in THF) to give 3.58 g of the title compound.

$^1$H NMR (DMSO-d$_6$): δ 2.49 (s, 3H, obscured by DMSO), 3.82 (s, 3H), 6.83 (dd, H, J=2.59 Hz and 8.70 Hz), 6.95 (s, 1H), 7.28 (t, 1H), 7.32 (d, 1H), 7.46–7.50 (m, 1H), 7.89–7.92 (m, 1H).

MS (ESI) m/z 323 ([M+H]$^+$);

EXAMPLES 1–29

Method B: 4-(1-substituted-6-hydroxy-1H-indazol-3-yl)benzene-1,3-diols

A solution of the substituted hydrazine salt (1 to 2 equivalents), sodium acetate (1 to 4 equivalents) and 2,2',4,4'-tetrahydroxybenzophenone (1 equivalent) in methanol (0.2 molar solution) was stirred at ambient temperature overnight. The reaction mixtures were concentrated in vacuo and the residues partitioned with EtOAc and H$_2$O. The organic phase was dried (Na$_2$SO$_4$) and concentrated in vacuo to give the intermediate hydrazone. The residues were heated at 190° C. overnight. Product residues were then purified by HPLC chromatography through silica gel columns 150×12 mm (Biotage) at 10 mL/min with methyl-t-butyl ether/hexane (1:3, v/v) to give 4-(1-substituted-6-hydroxy-1H-indazol-3-yl)benzene-1,3-diols.

EXAMPLE 1

4-(6-hydroxy-1-propyl-1H-indazol-3-yl)benzene-1,3-diol

Prepared according to Method B from 2,2',4,4'-tetrahydroxybenzophenone (0.123 g, 0.5 mmol), sodium acetate (0.164 g, 2 mmol) and propylhydrazine oxalate (0.164 g, 1.0 mmol) to give 0.075 g of product as a pink solid.

$^1$H NMR (DMSO-d$_6$): δ 0.846 (t, 3H, J=7.32 Hz), 1.83 (q, 2H, J=7.07 Hz), 4.24 (t, 2H, J=6.83 Hz), 6.36 (s, 1H), 6.41

(dd, 1H), 6.74 (dd, 1H), 6.85 (s, 1H), 7.74 (d, 1H, 7.91 (d, 1H), 9.587 (broad s, 1H), 9.857 (broad s, 1H), 10.882 (s, 1H).

MS (APCI) m/z 285 ([M+H]$^+$);

EXAMPLE 2

4-(1-butyl-6-hydroxy-1H-indazol-3-yl)benzene-1,3-diol

Prepared according to Method B from 2,2',4,4'-tetrahydroxybenzophenone (0.123 g, 0.5 mmol), sodium acetate (0.164 g, 2 mmol) and butylhydrazine oxalate (0.178 g, 1.0 mmol) to give 0.058 g of product as a pink solid $^1$H NMR (DMSO-$d_6$): δ 0.88 (t, 3H), 1.25 (m, 2H), 1.77 M, 2H), 4.28 (t, 2H), 6.36 (s, 1H), 6.41 (dd, 1H), 6.73 (dd, 1H), 6.84 (s, 1H) 7.73 (d, 1H), 7.89 (d, 1H), 9.57 (broad s, 1H), 9.823 (broad s, 1H), 10.856 (s, 1H).

MS (APCI) m/z 299 ([M+H]$^+$);

EXAMPLE 3

4-[6-hydroxy-1-(2-hydroxyethyl)-1H-indazol-3-yl] benzene-1,3-diol

Prepared according to Method B from 2,2',4,4'-tetrahydroxybenzophenone (0.123 g, 0.5 mmol), sodium acetate (0.164 g, 2 mmol) and 2-hydroxyethylhydrazine (0.085 g, 1.0 mmol) to give 0.020 g of product as a white solid $^1$H NMR (DMSO-$d_6$): δ 3.78 (m, 2H), 4.31 (m, 2H), 4.88 (t, 1H), 6.36 (2, 1H), 6.41 (dd, 1H), 6.73 (dd, 1H), 6.85 (s, 1H), 7.73 (d, 1H), 7.91 (d, 1H), 9.587 (broad s, 1H), 9.857 (broad s, 1H), 10.882 (s, 1H).

MS (APCI) m/z 287 ([M+H]$^+$);

EXAMPLE 4

4-(1-cyclohexyl-6-hydroxy-1H-indazol-3-yl)benzene-1,3-diol

Prepared according to Method B from 2,2',4,4'-tetrahydroxybenzophenone (0.123 g, 0.5 mmol), sodium acetate (0.164 g, 2 mmol) and cyclohexylhydrazine hydrochloride (0.150 g, 1.0 mmol) to give 0.040 g of product as a white solid $^1$H NMR (DMSO-$d_6$): δ 1.25 (m, 2H), 1.49 (m, 2H), 1.7 (m, 2H), 1.82 (m, 4H), 1.96 (m, 2H), 4.42 (m, 1H), 6.36 (2, 1H), 6.41 (dd, 1H), 6.75 (dd, 1H), 6.90 (s, 1H), 7.75 (d, 1H), 7.91 (d, 1H), 9.575 (broad s, 1H), 9.85 (broad s, 1H), 11.0175 (s, 1H).

MS (APCI) m/z 325 ([M+H]$^+$);

EXAMPLE 5

4-[6-hydroxy-1-(2,2,2-trifluoroethyl)-1H-indazol-3-yl]benzene-1,3-diol

Prepared according to Method B from 2,2',4,4'-tetrahydroxybenzophenone (0.123 g, 0.5 mmol), sodium acetate (0.164 g, 2 mmol) and 2,2,2-trifluoroethylhydrazine (0.088 mL, 1.0 mmol) to give 0.028 g of product as a yellow solid $^1$H NMR (DMSO-$d_6$): δ 5.36 (q, 2H), 6.39 (2, 1H), 6.41 (dd, 1H), 6.79 (dd, 1H), 6.98 (s, 1H), 7.65 (d, 1H), 7.86 (d, 1H), 9.629 (s, 1H), 9.97 (s, 1H), 10.4073 (s, 1H).

MS (APCI) m/z 323 [M–H]–.

EXAMPLE 6

4-[1-(3-chlorophenyl)-6-hydroxy-1H-indazol-3-yl] benzene-1,3-diol

Prepared according to Method B from 2,2',4,4'-tetrahydroxybenzophenone (2.46 g, 10 mmol), sodium acetate (0.82 g, 10 mmol) and 3-chlorophenylhydrazine hydrochloride (1.97 g, 11 mmol) to give 3.1 g of product as a tan solid Crystallized from EtOAc/hexane to give 1.4 g of an off-white solid (mp 228–230° C.).

$^1$H NMR (DMSO-$d_6$): δ 6.3995–6.4434 (m, 2H), 6.81 (dd, 1H), 7.15 (s, 1H), 7.43 (dd, 1H), 7.61 (m, 2H), 7.73 (dd, 1H), 7.80 (s, 1H), 7.86 (d, 1H), 9.648 (s, 1H), 10.00 (s, 1H), 10.1418 (s, 1H).

MS (APCI) m/z 353 ([M+H]$^+$);

Anal. calcd for $C_{19}H_{13}ClN_2O_3.H_2O$, C, 61.55; H, 4.08; N, 7.55; Found: C, 61.74; H, 3.57; N, 7.79.

EXAMPLE 7

4-[1-(4-bromophenyl)-6-hydroxy-1H-indazol-3-yl] benzene-1,3-di I

Prepared according to Method B from 2,2',4,4'-tetrahydroxybenzophenone (2.46 g, 10 mmol), sodium acetate (0.82 g, 10 mmol) and 4-bromophenylhydrazine hydrochloride (2.25 g, 10 mmol) to give 2.1 g of product as a tan solid. Crystallized from EtOAc/hexane to give 1.3 g of an off-white solid (mp 246° C.).

$^1$H NMR (DMSO-$d_6$): δ 6.42 (m, 2H), 6.82 (dd, 1H), 7.086 (s, 1H), 7.61 (d, 1H), 7.70 (m, 2H), 7.77 (m, 2H), 7.87 d, 1H), 9.64 (s, 1H), 10.0054 (s, 1H), 10.2061 (s, 1H.

MS (APCI) m/z 397 ([M+H]$^+$);

Anal. calcd for $C_{19}H_{13}BrN_2O_3.0.39$; $C_4H_8O_2$: C, 57.22; H, 3.76; N, 6.49; Found: C, 56.71; H, 3.50; N, 6.11.

EXAMPLE 8

4-[1-(2,5-dichlorophenyl)-6-hydroxy-1H-indazol-3-yl]benzene-1,3-diol

Prepared according to Method B from 2,2',4,4'-tetrahydroxybenzophenone (0.4 g, 1.6 mmol), sodium acetate (0.27 g, 3 mmol) and 2,5-dichlorophenylhydrazine hydrochloride (0.45 g, 2.5 mmol) to give 0.127 g of product as a beige solid (mp 78–80° C.).

$^1$H NMR (DMSO-$d_6$): δ 6.42 (m, 2H), 6.53 (s, 1H), 6.81 (dd, 1H), 7.66 (m, 2H), 7.80 (d, 1H), 7.85 (s, 1H), 7.92 (d, 1H), 7.87 d, 1H), 9.65 (s, 1H), 9.967 (s, 1H), 10.245 (s, 1H).

MS (ESI) m/z 387 ([M+H]$^+$);

Anal. calcd for $C_{19}H_{12}Cl_2N_2O_3$: C, 58.94; H, 3.12; N, 7.23; Found: C, 58.62; H, 3.92; N, 6.42.

EXAMPLE 9

4-[1-(2,5-difluorophenyl)-6-hydroxy-1H-indazol-3-yl]benzene-1,3-diol

Prepared according to Method B from 2,2',4,4'-tetrahydroxybenzophenone (0.4 g, 1.6 mmol), sodium acetate (0.27 g, 3 mmol) and 2,5-difluorophenylhydrazine hydrochloride (0.45 g, 3 mmol) to give 0.107 g of product as an off-white colored solid.

mp 88–91° C.;

¹H NMR (DMSO-d₆): δ 6.42 (m, 2H), 6.68 (s, 1H), 6.81 (dd, 1H), 7.41 (m, 1H), 7.63 m, 3H), 7.87 (d, 1H), 9.6508 (s, 1H), 9.986 (s, 1H), 10.1486 (s, 1H).
MS (ESI) m/z 355 ([M+H]$^+$);
Anal. calcd for $C_{19}H_{12}F_2N_2O_3$: C, 64.41; H, 3.41; N, 7.91; Found: C, 63.46; H, 3.34; N, 6.99.

EXAMPLE 10

4-[1-(5-bromo-2-methylphenyl)-6-hydroxy-1H-indazol-3-yl]benzene-1,3-diol

Prepared according to Method B from 2,2',4,4'-tetrahydroxybenzophenone (0.5 g, 2 mmol), sodium acetate (0.25 g, 3 mmol) and 5-bromophenylhydrazine hydrochloride (0.440 g, 2.4 mmol) to give 0.082 g of product as an off-white solid
mp 88–91° C.
¹H NMR (DMSO-d₆): δ 2.081 (s, 3H), 6.41 (m, 2H), 6.49 (s, 1H), 6.85 (dd, 1H), 7.46 (d, 1H), 7.65 (dd, 1H), 7.69 (dd, 2H), 7.94 (d, 1H), 9.11 (s, 1H), 9.63 (s, 1H), 10.357 (s, 1H).
MS (ESI) m/z 411 ([M+H]$^+$);
Anal. calcd for $C_{20}H_{15}BrN_2O_3$: C, 58.41; H, 3.68; N, 6.81; Found: C, 58.31; H, 4.11 N, 5.81.

EXAMPLE 11

4-[6-hydroxy-1-(4-methoxyphenyl)-1H-indazol-3-yl]benzene-1,3-diol

Prepared according to Method B from 2,2',4,4'-tetrahydroxybenzophenone (0.123 g, 0.5 mmol), sodium acetate (0.041 g, 0.5 mmol) and 4-methoxyphenylhydrazine hydrochloride (0.087 g, 0.5 mmol) to give 0.013 g of product as a tan solid
¹H NMR (DMSO-d₆): δ 3.835 (s, 3H), 6.4 (m, 2H), 6.93 (s, 1H), 7.14 (d, 2H), 7.61 (d, 2H), 7.93 (m, 2H), 9.61 (broad s, 1H), 9.934 (broad s, 1H), 10.460 (s, 1H).
MS (APCI) m/z 349 ([M+H]$^+$);

EXAMPLE 12

4-[6-hydroxy-1-(2-methoxyphenyl)-1H-indazol-3-yl]benzene-1,3-diol

Prepared according to Method B from 2,2',4,4'-tetrahydroxybenzophenone (0.123 g, 0.5 mmol), sodium acetate (0.041 g, 0.5 mmol) and 2-methoxyphenylhydrazine hydrochloride (0.087 g, 0.5 mmol) to give 0.010 g of product as a tan solid.
¹H NMR (DMSO-d₆): δ 3.871 (s, 3H), 6.42 (m, 2H), 6.77 (dd, 1H), 6.799 (m, 1H), 6.93 (s, 1H), 7.14 (t, 1H), 7.32 (dd, 1H), 7.49 (m, 2H), 7.75 (d, 1H), 7.95 (d, 1H), 9.62 (s, 1H), 9.824 (s, 1H), 10.63 (s, 1H).
MS (APCI) m/z 349 ([M+H]$^+$);

EXAMPLE 13

4-{6-hydroxy-1-[4-(trifluoromethoxy)phenyl]-1H-indazol-3-yl}benzene-1,3-diol

Prepared according to Method B from 2,2',4,4'-tetrahydroxybenzophenone (0.123 g, 0.5 mmol), sodium acetate (0.041 g, 0.5 mmol) and 4-trifluoromethoxyphenylhydrazine hydrochloride (0.114 g, 0.5 mmol) to give 0.045 g of product as a tan solid.

¹H NMR (DMSO-d₆): δ 6.43 (m, 2H), 6.82 (dd, 1H), 7.09 (s, 1H), 7.61 (m, 3H), 7.89 (m, 3H), 9.635 (s, 1H), 9.98 (s, 1H), 10.1896 (s, 1H).
MS (APCI) m/z 403 ([M+H]$^+$);

EXAMPLE 14

4-[1-(3-bromophenyl)-6-hydroxy-1H-indazol-3-yl]benzene-1,3-diol

Prepared according to Method B from 2,2',4,4'-tetrahydroxybenzophenone (0.123 g, 0.5 mmol), sodium acetate (0.041 g, 0.5 mmol) and 3-bromophenylhydrazine hydrochloride (0.112 g, 0.5 mmol) to give 0.016 g of product as a tan solid.
¹H NMR (DMSO-d₆): δ 6.42 (m, 2H), 6.81 (dd, 1H), 7.11 (s, 1H), 7.56 (m, 3H), 7.76 (m, 1H), 7.85 (d, 1H), 7.92 (s, 1H), 9.63 (s, 1H), 10.13 (s, 1H), 10.82 (s, 1H).
MS (APCI) m/z 397 ([M+H]$^+$);

EXAMPLE 15

4-[3-(2,4-dihydroxyphenyl)-6-hydroxy-1H-indazol-1-yl]benzonitrile

Prepared according to Method B from 2,2',4,4'-tetrahydroxybenzophenone (0.123 g, 0.5 mmol), sodium acetate (0.041 g, 0.5 mmol) and 4-cyanophenylhydrazine hydrochloride (0.085 g, 0.5 mmol) to give 0.012 g of product as a yellow solid MS (APCI) m/z 343 (M$^-$.).

EXAMPLE 16

4-[1-(2-chlorophenyl)-6-hydroxy-1H-indazol-3-yl]benzene-1,3-diol

A mixture of 2,2',4,4'-tetrahydroxybenzophenone (0.246 g, 1.0 mmol), ammonium chloride (0.16 g, 3 mmol) and 2-chlorophenyl hydrazine hydrochloride (0.535 g, 3 mmol) in 10 mL H₂O was heated at reflux for 4 hours. The reaction mixture was cooled and the solids formed were filtered washed with H₂O and dried to give 0.296 mg of the intermediate hydrazone. The hydrazone was heated to 200° C. under argon for 2 hours. The residue was purified by flash chromatography (hexane-EtOAc, 2:1) to give 0.055 g of product as a tan solid
¹H NMR (DMSO-d₆): δ 6.42 (m, 2H), 6.48 (s, 1H), 6.80 (dd, 1H), 7.58 (m, 2H), 7.66–7.79 (m, 3H), 7.96 (d, 1H), 9.64 (s, 1H), 9.925 (s, 1H), 10.406 (s, 1H).
MS (APCI) m/z 353 ([M+H]$^+$);

EXAMPLE 17

4-(1-ethyl-6-hydroxy-1H-indazol-3-yl)benzene-1,3-diol

A mixture of 2,2',4,4'-tetrahydroxybenzophenone (0.123 g, 0.5 mmol), sodium acetate (0.164 g, 2.0 mmol) and ethylhydrazine oxalate (0.30 g, 2.0 mmol) in 2 mL H₂O was heated at 90° C. overnight. The cooled reaction mixture was partitioned with EtOAc and 1 N HCl. The organic layer was dried (Na₂SO₄) and concentrated in vacuo to give the crude product. The residue was purified by HPLC chromatography using a silica gel column 150×12 mm (Biotage) at 10 mL/min with methyl-t-butyl ether/hexane (1:3, v/v) to give 0.025 g of product as an off-white solid.

$^1$H NMR (DMSO-d$_6$): δ 1.369 (t, 3H), 4.31 (q, 2H), 6.37 (s, 1H), 6.40 (dd, 1H), 6.74 (dd, 1H), 6.84 (s, 1H), 7.73 (d, 1H), 7.91 (d, 1H), 9.56 (s, 1H, 9.85 (s, 1H), 10.855 (s, 1H).
MS (APCI) m/z 271 ([M+H]$^+$);

EXAMPLE 18

4-(1-benzyl-6-hydroxy-1H-indazol-3-yl)benzene-1,3-diol

A mixture of 2,2',4,4'-tetrahydroxybenzophenone (0.123 g, 0.5 mmol), sodium acetate (0.164 g, 2.0 mmol) and benzylhydrazine dihydrochloride (0.39 g, 2.0 mmol) in 2 mL H$_2$O was heated at 90° C. overnight. The cooled reaction mixture was partitioned with EtOAc and 1 N HCl. The organic layer was dried (Na$_2$SO$_4$) and concentrated in vacuo to give the crude product. The residue was purified by HPLC chromatography using a silica gel column 150×12 mm (Biotage) at 10 mL/min with methyl-t-butyl ether/hexane (1:3, v/v) to give 0.062 g of product as an amber solid.

$^1$H NMR (DMSO-d$_6$): δ 5.54 (s, 2H), 6.36 (s, 1H), 6.41 (dd, 1H), 6.74 (dd, 1H), 6.88 (s, 1H), 7.21–7.33 (m, 5H), 7.73 (d, 1H), 7.91 (d, 1H), 9.58 (s, 1H), 9.856 (s, 1H), 10.760 (s, 1H).
MS (APCI) m/z 333 ([M+H]$^+$);

EXAMPLE 19

4-[6-hydroxy-1-(3-hydroxybenzyl)-1H-indazol-3-yl]benzene-1,3-diol

A mixture of 2,2',4,4'-tetrahydroxybenzophenone (0.123 g, 0.5 mmol), sodium acetate (0.164 g, 2.0 mmol) and 3-hydroxybenzylylhydrazine dihydrochloride (0.422 g, 1.0 mmol) in 2 mL H$_2$O was heated at 90° C. overnight. The cooled reaction mixture was partitioned with EtOAc and 1 N HCl. The organic layer was dried (Na$_2$SO$_4$) and concentrated in vacuo to give the crude product. The residue was purified by HPLC chromatography using a silica gel column 150×12 mm (Biotage) at 10 mL/min with methyl-t-butyl ether/hexane (1:3, v/v) to give 0.042 g of product as a yellow solid.

$^1$H NMR (DMSO-d$_6$): δ 5.46 (s, 2H), 6.37 (s, 1H), 6.41 (dd, 1H), 6.55 (s, 1H), 6.66 (m, 1H), 6.74 (dd, 1H), 6.84 (s, 1H), 7.09 (t, 1H), 7.74 (d, 1H), 7.92 (d, 1H), 9.38 (s, 1H), 9.588 (s, 1H), 9.862 (s, 1H), 10.794 (s, 1H).
MS (APCI) m/z 349 ([M+H]$^+$);

EXAMPLE 20

4-[6-hydroxy-1-(4-methylphenyl)-1H-indazol-3-yl]benzene-1,3-diol

Prepared according to Method B from 2,2',4,4'-tetrahydroxybenzophenone (0.400 g, 1.60 mmol), sodium acetate (0.267 g, 3.3 mmol) and 4-methylphenylhydrazine hydrochloride (0.390 g, 2.5 mmol) to give 0.018 g of product as a pink solid,
mp 160–162° C.
$^1$H NMR (DMSO-d$_6$): δ 2.39 (s, 3H), 6.40–6.43 (m, 2H), 6.80 (dd, 1H, J=1.95 and 8.79 Hz), 7.02 (s, H), 7.39 (d, 2H), 7.59 (d, 2H), 7.69 (d, 1H), 7.91 (d, H), 9.63 (s, H), 9.95 (s,H), 10.43 (s,H).
MS (APCI) m/z 333 ([M+H]$^+$);
Anal. calcd for C$_{20}$H$_{16}$N$_2$O$_3$.0.50 H$_2$O: C, 70.37; H, 5.02; N, 8.21; Found: C, 70.03; H, 5.28; N, 7.69.

EXAMPLE 21

4-[1-(3-fluorophenyl)-6-hydroxy-1H-indazol-3-yl]benzene-1,3-diol

Prepared according to Method B from 2,2',4,4'-tetrahydroxybenzophenone (0.400 g, 1.60 mmol), sodium acetate (0.267 g, 3.3 mmol) and 3-fluorophenylhydrazine hydrochloride (0.400 g, 2.5 mmol) to give 0.017 g of product as a pink solid.
$^1$H NMR (DMSO-d$_6$): δ 6.40–6.44 (m, 2H), 6.82 (dd, 1H, J=1.95 and 8.79 Hz), 7.14 (s, 1H), 7.19–7.24 (m, 1H), 7.60–7.63 (m, 4H), 7.86 (d, 1H), 9.65 (s, 1H), 10.00 (s, 1H), 10.17 (s, 1H).
mp>200° C.
MS (ACPI) m/z 337 ([M+H]$^+$)
Anal. calcd for C$_{19}$H$_{13}$FN$_2$O$_3$.0.50H$_2$O: C, 66.08; H, 4.09; N, 8.11; Found: C, 66.39; H, 3.72 ; N, 8.06.

EXAMPLE 22

4-[1-(2-fluorophenyl)-6-hydroxy-1H-indazol-3-yl]benzene-1,3-diol

Prepared according to Method B from 2,2',4,4'-tetrahydroxybenzophenone (0.400 g, 1.60 mmol), sodium acetate (0.267 g, 3.3 mmol) and 2-fluorophenylhydrazine hydrochloride (0.400 g, 2.5 mmol) to give 0.050 g of product as a pink solid.
mp>205° C.;
$^1$H NMR (DMSO-d$_6$): δ 6.41–6.43 (m, 2H), 6.63–6.64 (m, 1H), 6.81 (dd, 1H, J=1.95 and 8.79 Hz), 7.41–7.44 (m, 1H), 7.54–7.57 (m, 2H), 7.66–7.68 (m, 1H), 7.9 (d, 1H), 9.65 (broad s, 1H), 9.96 (broad s, 1H), 10.30 (broad s, 1H).
MS (APCI) m/z 337 ([M+H]$^+$);
Anal. calcd for C$_{19}$H$_{13}$FN$_2$O$_3$.0.10 C$_6$H$_{14}$.0.10H$_2$O: C, 67.89; H, 4.24; N, 8.08; Found: C, 67.71; H, 3.83; N, 7.87.

EXAMPLE 23

4-[6-hydroxy-1-(3-methylphenyl)-1H-indazol-3-yl]benzene-1,3-diol

Prepared according to Method B from 2,2',4,4'-tetrahydroxybenzophenone (0.400 g, 1.60 mmol), sodium acetate (0.267 g, 3.3 mmol) and 3-methylphenylhydrazine hydrochloride (0.390 g, 2.5 mmol) to give 0.178 g of product as a tan solid.
mp>200° C.;
$^1$H NMR (DMSO-d$_6$): δ 2.42 (s, 3H), 6.41–6.43 (m, 2H), 6.80 (dd, 1H, J=1.95 and 8.79 Hz), 7.07 (s, 1H), 7.47–7.67 (m, 3H), 7.68 (d, 1H), 9.64 (broad s, 1H), 9.96) broad s,1H), 10.40 (broad s, 1H).
Anal. calcd for C$_{20}$H$_{16}$N$_2$O$_3$.0.70 H$_2$O: C, 69.64; H, 5.08; N, 8.12; Found: C, 69.90; H, 4.40; N, 8.02.

EXAMPLE 24

4-[1-(3-chloro-4-fluorophenyl)-6-hydroxy-1H-indazol-3-yl]benzene-1,3-diol

Prepared according to Method B from 2,2',4,4'-tetrahydroxybenzophenone (0.400 g, 1.60 mmol), sodium acetate (0.267 g, 3.3 mmol) and 3-chloro-4-fluorophenylhydrazine hydrochloride (0.392 g, 2.5 mmol) to give 0.027 g of product as an off-white solid.
mp decomp at 185° C.;

¹H NMR (DMSO-d₆): δ 6.39–6.43 (m, 1H), 6.81 (dd, 1H), 7.05 (s, 1H), 7.59–7.64 (m, 2H), 7.74–7.78 (m, 1H), 7.84–7.86 (d, 1H), 7.91–7.97 (m, 1H), 9.64 (broad s, 1H), 10.10 (broad s, 1H), 10.11 (broad s, 1H).

MS (APCI) m/z 371 ([M+H]⁺);

Anal. calcd for $C_{19}H_{12}ClFN_2O_3 \cdot 0.25\ H_2O$: C, 60.81; H, 3.36; N, 7.46; Found: C, 59.72; H, 2.59; N, 7.25.

EXAMPLE 25

4-[6-hydroxy-1-(3-nitrophenyl)-1H-indazol-3-yl]benzene-1,3-diol

Prepared according to Method B from 2,2',4,4'-tetrahydroxybenzophenone (0.400 g, 1.60 mmol), sodium acetate (0.267 g, 3.3 mmol) and 3-nitrophenylhydrazine hydrochloride (0.463 g, 2.5 mmol) to give 0.149 g of product as a yellow ochre solid.

mp>205° C.;

¹H NMR (DMSO-d₆): δ 6.41 (dd, 1H, J=2.44 and 8.30 Hz), 6.44 (s, 1H), 6.84 (dd, 1H, 1.95 and 9.03 Hz), 7.20 (s, 1H), 7.56 (d, 1H), 7.83–7.89 (m, 2H), 8.18 (d, 1H), 8.24 (d, 1H), 8.50 (s, 1H), 9.65 (broad s, 1H), 10.02 (broad s, 1H), 10.98 (broad s, 1H).

MS (APCI) m/z 364 ([M+H]⁺);

Anal. calcd for $C_{19}H_{13}N_3O_5 \cdot 1.25\ H_2O$: C, 59.14; H, 4.05; N, 10.89; Found: C, 58.94; H, 3:66; N, 10.79.

EXAMPLE 26

4-{6-hydroxy-1-[3-(trifluoromethyl)phenyl]-1H-indazol-3-yl}benzene-1,3-diol

Prepared according to Method B from 2,2',4,4'-tetrahydroxybenzophenone (0.400 g, 1.60 mmol), sodium acetate (0.267 g, 3.3 mmol) and 3-trifluoromethylphenylhydrazine hydrochloride (0.430 g, 2.5 mmol) to give 0.209 g of product as a tan solid.

mp 201–203° C.;

¹H NMR (DMSO-d₆): δ 6.40–6.45 (m, 2H), 6.82 (dd, 1H, J=1.71 and 8.79), 7.13 (s, 1H), 7.58 (d, 1H), 7.73 (m, 1H), 7.81–7.86 (m, 2H), 8.03 (s, 1H), 8.07–8.09 (m, 1H), 9.65 (broad s, 1H), 10.04–10.07 (broad s, 2H).

MS (APCI) m/z 387 ([M+H]⁺);

Anal. calcd for $C_{20}H_{13}F_3N_2O_3 \cdot 1.25\ H_2O$: C, 58.76; H, 3.82; N, 6.85; Found: C, 58.71; H, 3.03; N, 6.89.

EXAMPLE 27

4-[6-hydroxy-1-(4-isopropylphenyl)-1H-indazol-3-yl]benzene-1,3-diol

Prepared according to Method B from 2,2',4,4'-tetrahydroxybenzophenone (0.400 g, 1.60 mmol), sodium acetate (0.267 g, 3.3 mmol) and 4-isopropylphenylhydrazine hydrochloride (0.455 g, 2.5 mmol) to give 0.141 g of product as a tan solid.

mp 130–133° C.;

¹H NMR (DMSO-d₆): δ 1.26 (d, 6H), 2.95–3.02 (m, 1H), 6.41–6.43 (m, 2H), 6.80 (dd, 1H, J=1.95 and 9.03 Hz), 7.03 (s, 1H), 7.45 (d, 2H), 7.61 (d, 2H), 7.67 (d, 1H), 7.92 (d, 1H), 9.64 (broad s, 1H), 9.93 (broad s, 1H), 10.45 (broad s, 1H).

MS (APCI) m/z 361 ([M+H]⁺);

Anal. calcd for $C_{22}H_{20}N_2O_3 \cdot 0.50\ H_2O$: C, 71.53; H, 5.73; N, 7.58; Found: C, 72.83; H, 5.61; N, 7.50.

EXAMPLE 28

4-{6-hydroxy-1-[4-(methylsulfonyl)phenyl]-1H-indazol-3-yl}benzene-1,3-diol

Prepared according to Method B from 2,2',4,4'-tetrahydroxybenzophenone (0.400 g, 1.60 mmol), sodium acetate (0.267 g, 3.3 mmol) and (4-methanesulfonyl)phenylhydrazine hydrochloride (0.454 g, 2.5 mmol) to give 0.378 g of product as a tan solid.

mp 94–96° C.;

¹H NMR (DMSO-d₆): δ 3.28 (s, 3H), 6.41 (dd, 1H, 2.44 and 8.54 Hz), 6.45 (s, 1H), 6.63 (d, 1H), 6.85 (dd, 1H, J=1.95 and 8.78 Hz), 7.24 (s, H), 7.48 (dd, 1H, J=1.95 and 6.83 Hz), 7.58 (d, 1H), 7.84 (d, 1H), 8.03 (dd, 1H, J=2.20 and 4.15 Hz), 8.12 (d, 1H), 9.76 (broad s, 1H), 10.09 (broad s, 2H).

MS (APCI) m/z 397 ([M+H]⁺);

Anal. calcd for $C_{20}H_{16}N_2O_5S \cdot 1.50\ H_2O$: C, 56.73; H, 4.52; N, 6.62; Found: C, 56.75; H, 4.00; N, 6.73.

EXAMPLE 29

4-[6-hydroxy-1-(4-nitrophenyl)-1H-indazol-3-yl]benzene-1,3-diol

Prepared according to Method B from 2,2',4,4'-tetrahydroxybenzophenone (0.400 g, 1.60 mmol), sodium acetate (0.267 g, 3.3 mmol) and 4-nitrophenylhydrazine hydrochloride (0.463 g, 2.5 mmol) to give 0.101 g of product as a pink solid.

mp>200° C.;

¹H NMR (DMSO-d₆): δ 6.41 (d, 1H), 6.46 (s, 1H), 6.87 (dd, 1H, J=1.71 and 8.79 Hz), 7.29 (s, 1H), 7.55 (d, 1H), 7.83 (d, 1H), 8.04 (d, 2H), 8.41 (d, 2H), 9.68 (broad s, 1H), 10.01 (broad s, 1H), 10.14 (broad s, 1H).

MS (APCI) m/z 364 ([M+H]⁺);

Anal. calcd for $C_{19}H_{13}N_3O_5 \cdot H_2O$: C, 59.84H, 3.96 N, 11.02 Found: C, 60.33; H, 3.46; N, 10.86.

EXAMPLES 30–33

Method C:
4-(1,7-disubstituted-1H-indazol-3-yl)phenols

Step A: A solution of (2-fluoro-3-substituted-phenyl)(4-methoxy-2-substituted-phenyl)-methanone (1 equivalent), 1-substituted hydrazine (1 eq.) and DMAP (1 eq.) in pyridine was heated at 100° C. for hrs. The cool reaction mixture was partitioned with EtOAc and 1 N HCl. The organic phase was washed with brine and dried (Na₂SO₄). The resulting residue was purified by flash chromatography.

Step B: A solution of 3-(4-methoxyphenyl)-7-substituted-1-substituted-1H-indazole in CH₂Cl₂ containing excess equivalents of cyclohexene at −78° C. was treated with boron tribromide (4 eq.) and slowly allowed to warm to ambient temperature. The reaction was quenched by dropwise edition of CH₃OH to the cooled reaction. The solvent was removed in vacuo and the residue partitioned with EtOAc and 1 N HCl. The organic phase was washed with brine and dried (Na₂SO₄). Removal of the solvent afforded the crude product which was isolated in pure form either by crystallization or by flash chromatography through water deactivated silica gel.

EXAMPLE 30

4-(7-chloro-1-cyclohexyl-1H-indazol-3-yl)phenol

Step 1: 7-chloro-1-cyclohexyl-3-(4-methoxyphenyl)-1H-indazole

Prepared according to Method C step A (3-chloro-2-fluorophenyl)-(4-methoxyphenyl)-methanone (0.55 g, 1.85 mmol), cyclohexylhydrazine hydrochloride (0.42 g, 2.7 mmol) and DMAP (0.225 g, 1.85 mmol) to give the product (0.58 g) as a yellow oil.

$^1$H NMR (DMSO-d$_6$): δ 1.2–1.3 (m, 1H), 1.465 (m, 2H), 1.71 (d, 1H), 1.875 (2H), 1.97 (m, 2H), 2.07 (m, 2H), 3.817 (s, 3H), 7.08 (d, 2H), 7.175 (t, 1H), 7.48 (dd, 1H), 7.825 (d, 2H), 7.96 (dd, 1H).

MS (APCI) m/z 341 ([M+H]$^+$);

Step 2: 4-(7-chloro-1-cyclohexyl-1H-indazol-3-yl)phenol

Prepared according to Method C step B from 7-chloro-1-cyclohexyl-3-(4-methoxyphenyl)-1H-indazole (0.55 g, 1.61 mmol), boron tribromide (0.61 mL, 6.5 mmol) and 1.0 mL of cyclohexene to give the product (0.26 g) as an off-white solid.

mp 176–177° C.;

$^1$H NMR (DMSO-d$_6$): δ 1.24 (m, 1H), 1.46 (m, 2H), 1.70 (d, 1H), 1.87 (d, 2H 1.96 (m, 2H), 2.03 (d, 2H), 5.23 (m, 1H), 6.90 (dd, 2H), 7.15 (t, 1H), 7.47 (d, 1H), 7.71 (d, 2H), 7.94 (d, 1H), 9.655 (s, 1H).

MS (ESI) m/z 327 ([M+H]$^+$);

Anal. calcd for $C_{19}H_{19}ClN_2O$: C, 69.83H, 5.86 N, 8.57 Found: C, 69.47; H, 5.87; N, 8.36.

EXAMPLE 31

4-[1-(4-bromophenyl)-7-(trifluoromethyl)-1H-indazol-3-yl]phenol

Step 1: 1-(4-bromophenyl)-3-(4-methoxyphenyl)-7-trifluoromethyl-1H-indazole

Prepared according to Method C step A from (2-fluoro-3-trifluoromethyl-phenyl)-(4-methoxyphenyl)-methanone (0.149 g, 0.5 mmol), 4-bromophenylhydrazine hydrochloride (0.134 g, 0.6 mmol) and DMAP (0.061 g, 0.5 mmol) to give the title compound.

$^1$H NMR (DMSO-d$_6$): δ 3.83 (s, 3H), 7.11 (d, 2H), 7.45 (m, 3H), 7.76 (d, 2H 7.9 (d, 2H), 8.42 (d, 1H).

MS (APCI) m/z 447 ([M+H]$^+$);

Step 2: 4-[1-(4-bromophenyl)-7-(trifluoromethyl)-1H-indazol-3-yl]phenol

Prepared according to Method C step B from 1-(4-bromophenyl)-3-(4-methoxyphenyl)-7-trifluoromethyl-1H-indazole (0.5 mmol), boron tribromide (0.188 mL, 2.0 mmol) and 0.2 mL of cyclohexene to give the product (0.025 g) as a tan solid.

mp 176–177° C.;

$^1$H NMR (DMSO-d$_6$): δ 6.93 (dd, 2H), 7.51 (m, 3H), 7.76 (m, 4H), 7.90 (d, 1H), 8.41 (d, 1H), 9.79 (s, 1H).

MS (APCI) m/z 433 ([M+H]$^+$);

EXAMPLE 32

4-[1-cyclohexyl-7-(trifluoromethyl)-1H-indazol-3-yl]phenol

Step 1: 1-cyclohexyl-3-(4-methoxyphenyl)-7-trifluoromethyl-1H-indazole

Prepared according to Method C step A (2-fluoro-3-trifluoromethyl-phenyl)-(4-methoxyphenyl)-methanone (0.149 g, 0.5 mmol), cyclohexylhydrazine hydrochloride (0.90 g, 0.6 mmol) and DMAP (0.061 g, 0.5 mmol) to give the title compound.

$^1$H NMR (DMSO-d$_6$): δ 1.24 (m, 1H), 1.38 (m, 2H), 1.725 (d, 1H), 1.75–2.2 (m, 6H), 3.82 (s, 3H), 4.56 (m, 1H), 7.10 (d, 2H), 7.35 (m, 1H), 7.84 (m, 3H), 8.31 (d, 1H).

MS (APCI) m/z 375 ([M+H]$^+$);

Step 2: 4-[1-cyclohexyl-7-(trifluoromethyl)-1H-indazol-3-yl]phenol

Prepared according to Method C step B from 1-cyclohexyl-3-(4-methoxyphenyl)-7-trifluoromethyl-1H-indazole (0.5 mmol), boron tribromide (0.188 mL, 2.0 mmol) and 0.2 mL of cyclohexene to give the product (0.028 g) as a tan solid.

$^1$H NMR (DMSO-d$_6$): δ 1.2–1.42 (m, 4H), 1.71 (d, 1H), 1.92 (m, 3H), 2.03 (m, 2H), 4.54 (m, 1H), 6.92 (dd, 2H), 7.33 (t, 1H), 7.72 (d, 2H), 7.86 (d, 1H), 8.28 (d, 1H, 9.72 (s, 1H).

MS (APCI) m/z 361 ([M+H]$^+$);

EXAMPLE 33

4-(1-cyclohexyl-7-fluoro-1H-indazol-3-yl)phenol

Step 1: 1-cyclohexyl-7-fluoro-3-(4-methoxyphenyl)-1H-indazole

Prepared according to Method C step A (2,3-difluorophenyl)-(4-methoxyphenyl)-methanone (0.150 g, 0.6 mmol), cyclohexylhydrazine hydrochloride (0.90 g, 0.6 mmol) and DMAP (0.073 g, 0.6 mmol) to give 0.09 g of the title compound.

$^1$H NMR (DMSO-d$_6$): δ 1.3 (m, 1H), 1.45 (m, 2H), 1.725 (d, 1H), 1.8–2.1 (m, 6H), 3.812 (s, 3H), 4.65 (m, 1H), 7.075 (d, 2H), 7.15 (m, 1H), 7.2–7.3 (m, 2H), 7.84 (m, 3H).

MS (ESI) m/z 325 ([M+H]$^+$);

Step 2: 4-[1-cyclohexyl7-(fluoro)-1H-indazol-3-yl]phenol

Prepared according to Method C step B from 1-cyclohexyl-7-fluoro-3-(4-methoxyphenyl)-1H-indazole (0.9 g, 0.5 mmol), boron tribromide (0.094 mL, 1.0 mmol) and 0.5 mL of cyclohexene to give the product (0.040 g) as a tan solid.

$^1$H NMR (DMSO-d$_6$): δ 1.25 (m, 1H), 1.42 (m, 2H), 1.695 (d, 1H), 1.86 (d, 2H), 1.96 (m, 2H), 2.04 (m, 2H), 4.64 (m, 1H), 6.90 (dd, 2H), 7.13 (m, 1H), 7.23 (m, 1H), 7.73 (D, 2H), 7.79 (d, 1H), 9.657 (s, 1H).

MS (APCI) m/z 311 ([M+H]$^+$);

Method D:
4-(1,7-disubstituted-1H-indazol-3-yl)phenols

Step A: A solution of (2-fluoro-3-substituted-phenyl)(4-methoxy-2-substituted-phenyl)-methanone (1 equivalent), hydrazine hydrate (10 eq.) and DMAP (1 eq.) in pyridine was heated at 100° C. for 24–48 hrs. The cooled reaction mixture was partitioned with EtOAc and 1 N HCl. The organic phase was washed with brine and dried (Na$_2$SO$_4$). The resulting residue was purified by flash chromatography to give the intermediate 3-(4-methoxyphenyl)-7-substituted-1-1H-indazole.

Step B: A solution of the intermediate 3-(4-methoxyphenyl)-7-substituted-1-1H-indazole (1 eq.) in DMF was added in one portion sodium hydride (1 eq., 60% in oil). After the gas evolution ceased, the alkyl halide was added and the reaction was stirred at ambient to 50° C. overnight. The cool reaction mixture was partitioned with EtOAc and 1 N HCl. The organic phase was washed with brine and dried (Na$_2$SO$_4$). The resulting residue was purified by flash chromatography or by HPLC chromatography through silica gel columns 150×12 mm (Biotage) at 10 mL/min with methyl-t-butyl ether/hexane (gradient elution 1:9 to 1:1) to give the intermediates 3-(4-methoxyphenyl)-7-substituted-1-substituted-1H-indazole and 3-(4-methoxyphenyl)-7-substituted-2-substituted-2H-indazole.

Step C: A solution of 3-(4-methoxyphenyl)-7-substituted-(1 or 2-substituted)-(1H or 2H)-indazole (1 eq.) in CH$_2$Cl$_2$ containing excess equivalents of cyclohexene at −78° C. was treated with boron tribromide (4 eq.) and slowly allowed to warm to ambient temperature. The reaction was quenched by dropwise edition of CH$_3$OH to the cooled reaction. The solvent was removed in vacuo and the residue partitioned with EtOAc and 1 N HCl. The organic phase was washed with brine and dried (Na$_2$SO$_4$). Removal of the solvent in vacuo afforded the crude product. Pure product was obtained by crystallization or flash chromatography through water deactivated silica gel. Note: HPLC retention times were obtained using the following conditions:

| | |
|---|---|
| Column: | Keystone Aquasil C18 (50 × 2 mm, 5 u), |
| Solvent System: | A: 95% 10 mM NH4OAc/5% acetonitrile, |
| | B: 95% acetonitrile 5% 10 mM NH$_4$OAc, |
| Gradient | 0% B to 100% B over 0–15 minutes, |
| Flow | 0.8 mL/min |
| Detection: | UV. various wavelengths |

INTERMEDIATES 16–27

Intermediate 16

3-(4-methoxyphenyl)-7-methyl-1H-indazole

Prepared according to Method D Step A from (2-Fluoro-3-methylphenyl)-(4-methoxyphenyl)-methanone (3.6 g, 14.7 mmol), hydrazine hydrate (4.3 mL, 140 mmol) and DMAP (1.8 g, 14.7 mmol) to give the product (1.7 g) as a yellow solid.
$^1$H NMR (DMSO-d$_6$): δ 2.52 (s, 3H), 3.81 (s, 3H), 7.06 (m, 3H), 7.13 (d, 1H), 7.81 (d, 1H), 7.89 (d, 2H), 13.132 (s, 1H).
MS (APCI) m/z 239 ([M+H]$^+$);

Intermediate 17

3-(4-methoxyphenyl)-7-trifluoromethyl-1H-indazole

Prepared according to Method D Step A from (2-Fluoro-3-trifluoromethylphenyl)-(4-methoxyphenyl)-methanone (3.6 g, 14.7 mmol), hydrazine hydrate (4.3 mL, 140 mmol) and DMAP (1.8 g, 14.7 mmol) to give the product (1.7 g) as a yellow solid.
$^1$H NMR (DMSO-d$_6$, 300 MHz): δ 2.52 (s, 3H), 3.82 (s, 3H), 7.07 (d, 2H), 7.18 (t, 1H), 7.48 (d, 1H), 7.91 (d, 2H), 8.0 (d, 1H), 13.132 (s, 1H).
MS (APCI) m/z 239 ([M+H]$^+$);

Intermediate 18

7-chloro-3-(4-methoxyphenyl)-1H-indazole

Prepared according to Method D Step A from (3-chloro-2-fluoro-phenyl)-(4-methoxyphenyl)-methanone (0.84 g, 3.2 mmol), hydrazine hydrate (1.0 mL, 32 mmol) and DMAP (0.39 g, 3.2 mmol) to give the product (0.75 g) as a white solid.
$^1$H NMR (DMSO-d$_6$): 3.81 (s, 3H), 7.06 (d, 2H), 7.13 (d, 1H), 7.81 (d, 1H), 7.89 (d, 2H), 13.52 (s, 1H).
MS (APCI) m/z 259 ([M+H]J);

Intermediate 19

7-fluoro-3-(4-methoxyphenyl)-1H-indazole

Prepared according to Method D Step A from (2,3-difluorophenyl)-(4-methoxyphenyl)-methanone (1.1 g, 4.4 mmol), hydrazine hydrate (1.37 mL, 44 mmol) and DMAP (0.54 g, 4.4 mmol) to give the product (0.85 g) as a white solid.
$^1$H NMR (DMSO-d$_6$): 3.82 (s, 3H), 7.06 (d, 3H), 7.1–7.25 (m, 2H), 7.83 (d, 1H), 7.92 (d, 2H), 13.53 (s, 1H).
MS (APCI) m/z 243 ([M+H]$^+$);

Intermediate 20

7-fluoro-3-(4-methoxy-3-methylphenyl)-1H-indazole

Prepared according to Method D Step A from (2,3-difluorophenyl)-(4-methoxy-3-methyl-phenyl)-methanone (0.9 g, 3.45 mmol), hydrazine hydrate (1.06 mL, 34 mmol) and DMAP (0.42 g, 3.45 mmol) to give the product (0.80 g) as a yellow solid.
$^1$H NMR (DMSO-d$_6$): δ 2.247 (s, 3H), 3.845 (s, 3H), 7.07 (d, 1H), 7.13 (m, 1H), 7.22 (m, 1H), 7.75 (m, 2H), 7.83 (d, 1H), 13.62 (broad s, 1H)
MS (ESI) m/z 257 ([M+H]$^+$);

Intermediate 21

3-(2,4-dimethoxyphenyl)-7-(trifluoromethyl)-1H-indazole

Prepared according to Method D Step A from (2,4-dimethoxyphenyl)[2-fluoro-3-(trifluoromethyl)phenyl]methanone (1.50 g, 5.17 mmol), hydrazine hydrate (1.61 mL, 51.7 mmol) and DMAP (0.632 g, 5.17 mmol) to give the product (0.619 g) as a yellow solid.
$^1$H NMR (DMSO-d$_6$): δ 3.78 (s, 3H), 3.83 (s, 3H), 6.66 (dd, 1H, J=2.38 and 8.33 Hz), 6.75 (s, 1H), 7.24 (t, 1H), 7.43 (d, 1H), 7.72 (d, 1H), 7.89 (d, 1H)
MS (APCI) m/z 323 ([M+H]$^+$);
Anal. calcd for $C_{16}H_{13}F_3N_2O_2$: C, 59.63; H, 4.07; N, 8.69. Found: C, 59.91; H, 4.08; N, 7.95.

Intermediate 22

3-(4-methoxy-2-methylphenyl)-7-(trifluoromethyl)-1H-indazole

Prepared according to Method D Step A from [2-fluoro-3-(trifluoromethyl)phenyl](4-methoxy-2-methylphenyl)

methanone (1.34 g, 4.90 mmol), hydrazine hydrate (1.61 mL, 51.7 mmol) and DMAP (0.632 g, 5.17 mmol) to give the product (0.620 g) as a yellow solid.

$^1$H NMR (DMSO-d$_6$): δ 2.31 (s, 3H), 3.81 (s, 3H), 6.92 (d, 1H), 6.98 (s, 1H), 7.29 (t, 1H), 7.41 (d, 1H), 7.70 (d, 1H), 7.90 (d, 1H)

MS (APCI) m/z 307 ([M+H]$^+$);

Anal. calcd for $C_{16}H_{13}F_3N_2O$: C, 62.74; H, 4.28; N, 9.15. Found: C, 62.35; H, 4.01; N, 9.34.

Intermediate 23

3-(2,4-dimethoxyphenyl)-7-fluoro-1H-indazole

Prepared according to Method D Step A from (2,4-dimethoxyphenyl)[2,3-difluorophenyl]-methanone (1.60 g, 5.8 mmol), hydrazine hydrate (1.79 mL, 5702 mmol) and DMAP (0.632 g, 57.5 mmol) to give the product (1.66 g) as a yellow solid.

$^1$H NMR (DMSO-d$_6$): δ 3.77 (s, 3H), 3.83 (s, 3H), 6.65 (dd, 1H, J=2.13 and 8.40 Hz), 6.72 (s, 1H), 7.02–7.05 (m, 1H), 7.13–7.17 (m, 1H), 7.41 (t, 1H), 13.54 (broad s, 1H)

MS (ESI) m/z 273 ([M+H]$^+$);

Intermediate 24

7-fluoro-3-(4-methoxy-2-methylphenyl)-1H-indazole

Prepared according to Method D Step A from [2-fluoro-3-(trifluoromethyl)phenyl](4-methoxy-2-methylphenyl)methanone (1.34 g, 4.90 mmol), hydrazine hydrate (1.61 mL, 51.7 mmol) and DMAP (0.632 g, 5.17 mmol) to give the product (0.620 g) as a yellow solid.

$^1$H NMR (DMSO-d$_6$): δ 2.30 (s, 3H), 3.80 (s, 3H), 6.89 (dd, 1H, J=2.44 and 8.39 Hz), 6.95 (s, 1H), 7.06–7.11 (m, 1H), 7.19–7.22 (m, 1H), 7.38–7.40 (m, 2H), 13.64 (broad s, 1H)

MS (ESI) m/z 257 ([M+H]$^+$);

Intermediate 25

7-chloro-3-(4-methoxy-2-methylphenyl)-1H-indazole

Prepared according to Method D Step A from [2-fluoro-3-chlorophenyl](4-methoxy-2-methylphenyl)methanone (1.26 g, 4.52 mmol), hydrazine hydrate (1.61 mL, 51.7 mmol) and DMAP (0.632 g, 5.17 mmol) to give the product (0.613 g) as a yellow solid.

$^1$H NMR (DMSO-d$_6$): δ 2.31 (s, 3H), 3.81 (s, 3H), 6.89 (dd, 1H, J=2.57 and 8.53 Hz), 6.96 (s, 1H), 7.13 (t, 1H), 7.39 (d, 1H), 7.47 (d, 1H), 7.54 (d, 1H), 13.62 (broad s, 1H)

MS (ESI) m/z 273 ([M+H]$^+$);

Intermediate 26

7-chloro-3-(2,4-dimethoxyphenyl)-1H-indazole

Prepared according to Method D Step A from (2,4-dimethoxyphenyl)[2-fluoro-3-chlorophenyl]methanone (1.20 g, 4.1 mmol), hydrazine hydrate (1.61 mL, 51.7 mmol) and DMAP (0.632 g, 5.17 mmol) to give the product (0.618 g) as a yellow solid.

$^1$H NMR (DMSO-d$_6$): δ 3.77 (s, 3H), 3.83 (s, 3H), 6.65 (dd, 1H, J=2.18 and 8.33 Hz), 6.73 (s, 1H), 7.07 (t, 1H), 7.41 (d, 1H), 7.55 (d, 1H), 13.52 (broad s, 1H)

MS (ESI) m/z 289 ([M+H]$^+$);

Intermediate 27

3-(2,4-dimethoxyphenyl)-7-fluoro-1H-indazole

Prepared according to Method D Step A from (2,4-dimethoxyphenyl)[2-fluoro-3-chlorophenyl]methanone (1.20 g, 4.1 mmol), hydrazine hydrate (1.60 mL, 57.5 mmol) and DMAP (0.702 g, 5.75 mmol) to give the product (1.50 g) as a dark oil.

$^1$H NMR (DMSO-d$_6$): 3.77 (s, 3H), 3.83 (s, 3H), 6.65 (dd, 1H, J=2.13 and 8.40 Hz), 6.72 (s, 1H), 7.02–7.05 (m, 1H), 7.13–7.17 (m, 1H), 7.41 (t, 1H), 13.54 (broad s, 1H)

MS (ESI) m/z 273 ([M+H]$^+$);

EXAMPLES 34–123

EXAMPLE 34

4-(7-methyl-1H-indazol-3-yl) phenol

Prepared according to Method D step C from 3-(4-methoxyphenyl)-7-methyl-1H-indazole (0.10 g, 0.42 mmol), boron tribromide (0.159 mL, 1.68 mmol) and 0.5 mL of cyclohexene to give the product (0.070 g) as an off-white solid.

mp sinters 149, melts 190° C.;

$^1$H NMR (DMSO-d$_6$): δ 2.51 (s, 3H),), 6.88 (d, 2H). 7.05 (t, 1H), 7.13 (d, 1H), 7.78 (m, 1H), 9.57 (broad s, 1H), 13.06 (broad s, 1H).

MS (APCI) m/z 225 ([M+H]$^+$);

Anal. calcd for $C_{14}H_{12}N_2O \cdot H_2O$: C, 69.41; H, 5.82; N, 11.56. Found: C, 69.82; H, 5.08; N, 11.60.

EXAMPLE 35

4-(7-methyl-1-pentyl-1H-indazol-3-yl)phenol

Step 1:
3-(4-methoxyphenyl)-7-methyl-1-pentyl-1H-indazole

Prepared according to Method D step B from 3-(4-methoxyphenyl)-7-methyl-1H-indazole (0.23 g, 1.0 mmol), sodium hydride (60% in oil, 0.048 g, 1.2 mmol) and 1-iodopentane (0.26 mL, 2.0 mmol) to give the title compound (0.105 g) as a white solid.

$^1$H NMR (DMSO-d$_6$): δ 0.85 (t, 3H), 1.3099 (m, 4H), 1.81 (m, 2H), 2.7158 (s, 3H), 3.810 (s, 3H), 4.567 (t, 2H), 7.06 (m, 2H), 7.15 (d, 1H), 7.82 (m, 3H).

MS (APCI) m/z 309 ([M+H]$^+$);

Step 2:
4-(7-methyl-1-pentyl-1H-indazol-3-yl)phenol

Prepared according to Method D step C from 3-(4-methoxyphenyl)-7-methyl-1-pentyl-1H-indazole (0.105 g, 0.34 mmol), boron tribromide (0.094 mL, 1.0 mmol) and 0.3 mL of cyclohexene to give the product (0.043 g) as an off-white solid.

$^1$H NMR (DMSO-d$_6$): δ 0.847 (t, 3H), 1.3038 (m, 4H), 1.798 (m, 2H), 2.704 (s, 3H), 4.548 (t, 2H), 6.88 (d, 2H), 7.03 (t, 1H), 7.13 (d, 1H), 7.70 (d, 2H), 7.78 (d, 1H), 9.58 (broad s, 1H).

MS (APCI) m/z 295 ([M+H]$^+$);

EXAMPLE 36

4-[7-methyl-2-pentyl-2H-indazol-3-yl]phenol

Step 1:
3-(4-methoxyphenyl)-7-methyl-2-pentyl-2H-indazole

Prepared according to Method D step B from 3-(4-methoxyphenyl)-7-methyl-1H-indazole (0.23 g, 1.0 mmol), sodium hydride (60% in oil, 0.048 g, 1.2 mmol) and 1-iodopentane (0.26 mL, 2.0 mmol) to give the title compound (0.014 g). Used as is in the next step.

Step 2:
4-[7-methyl-2-pentyl-2H-indazol-3-yl]phenol

Prepared according to Method D step C from 3-(4-methoxyphenyl)-7-methyl-2-pentyl-2H-indazole (0.014 g, 0.045 mmol), boron tribromide (0.050 mL, 1.0 mmol) and 0.2 mL of cyclohexene to give the product (0.006 g).
$^1$H NMR (300 MHz, DMSO-$d_6$): δ 0.78 (t, 3H), 1.17 (m, 4H), 1.82 (m, 2H), 4.32 (t, 2H), 6.85–7.0 (m, 3H), 7.25 (d, 1H), 7.35 (d, 2H), 9.85 (broad s, 1H).
MS (ESI) m/z 295 ([M+H]$^+$);
RT–7.06 min

EXAMPLE 37

4-(7-methyl-1-propyl-1H-indazol-3-yl)phenol

Step 1:
3-(4-methoxyphenyl)-7-methyl-1-propyl-1H-indazole

Prepared according to Method D step B from 3-(4-methoxyphenyl)-7-methyl-1H-indazole (0.115 g, 0.5 mmol), sodium hydride (60% in oil, 0.024 g, 0.6 mmol) and 1-iodopropane (0.098 mL, 1.0 mmol) to give the title compound (0.070 g) as a white solid.
$^1$H NMR (DMSO-$d_6$): δ 0.902 (t, 3H), 1.83 (m, 2H), 2.7139 (s, 3H), 3.809 (s, 3H), 4.538 (t, 2H), 7.05 (m, 2H), 7.15 (d, 1H), 7.83 (m, 3H).
MS (APCI) m/z 281 ([M+H]$^+$);

Step 2:
4-(7-methyl-1-propyl-1H-indazol-3-yl)phenol

Prepared according to Method D step C from 3-(4-methoxyphenyl)-7-methyl-1-propyl-1H-indazole (0.07 g, 0.25 mmol), boron tribromide (0.094 mL, 1.0 mmol) and 0.3 mL of cyclohexene to give the product (0.033 g) as an off-white solid.
$^1$H NMR (DMSO-$d_6$): δ 0.894 (t, 3H), 1.82 (m, 2H), 2.704 (s, 3H), 4.52 (t, 2H), 6.88 (d, 2H), 7.03 (t, 1H), 7.12 (d, 1H), 7.70 (d, 2H), 7.78 (d, 1H). 9.57 (broad s, 1H).
MS (ESI) m/z 267 ([M+H]$^+$);
Anal. calcd for $C_{17}H_{18}N_2O$. 0.25 $H_2O$: C, 75.39; H, 6.88N, 10.34. Found: C, 75.10; H, 6.77; N, 9.98.

EXAMPLE 38

4-[7-methyl-2-propyl-2H-indazol-3-yl]phenol

Step 1:
3-(4-methoxyphenyl)-7-methyl-2-propyl-2H-indazole

Prepared according to Method D step B from 3-(4-methoxyphenyl)-7-methyl-1H-indazole (0.115 g, 0.5 mmol), sodium hydride (60% in oil, 0.024 g, 0.6 mmol) and 1-iodopropane (0.098 mL, 1.0 mmol) to give the title compound (0.014 g). Used as is in the next step.

Step 2:
4-[7-methyl-2-propyl-2H-indazol-3-yl]phenol

Prepared according to Method D step C from 3-(4-methoxyphenyl)-7-methyl-2-propyl-2H-indazole (0.014 g, 0.05 mmol), boron tribromide (0.050 mL, 1.0 mmol) and 0.2 mL of cyclohexene to give the product (0.007 g).
MS (ESI) m/z 267 ([M+H]$^+$);
RT=6.02 min

EXAMPLE 39

4-(1-isopropyl-7-methyl-1H-indazol-3-yl)phenol

Step 1: 1-isopropyl-3-(4-methoxyphenyl)-7-methyl-1H-indazole

Prepared according to Method D step B from 3-(4-methoxyphenyl)-7-methyl-1H-indazole (0.115 g, 0.5 mmol), sodium hydride (60% in oil, 0.024 g, 0.6 mmol) and 2-iodopropane (0.10 mL, 1.0 mmol) to give the title compound (0.057 g) as a white solid.
$^1$H NMR (DMSO-$d_6$): δ 1.53 (d, 6H), 2.7328 (s, 3H), 3.8117 (s, 3H), 5.25 (m, 1H), 7.05 (m, 2H), 7.15 (d, 1H), 7.83 (m, 3H).
MS (APCI) m/z 281 ([M+H]$^+$);

Step 2:
4-(1-isopropyl-7-methyl-1H-indazol-3-yl)phenol

Prepared according to Method D step C from 1-isopropyl-3-(4-methoxyphenyl)-7-methyl-1H-indazole (0.057 g, 0.20 mmol), boron tribromide (0.094 mL, 1.0 mmol) and 0.3 mL of cyclohexene to give the product (0.027 g) as an off-white solid.
$^1$H NMR (DMSO-$d_6$): δ 1.51 (d, 6H), 2.723 (s, 3H), 5.235 (m, 1H), 6.89 (d, 2H), 7.03 (t, 1H), 7.12 (d, 1H), 7.71 (d, 2H), 7.77 (d, 1H), 9.58 (s, 1H).
MS (APCI) m/z 267 ([M+H]$^+$);

EXAMPLE 40

4-[2-isopropyl-7-methyl-2H-indazol-3-yl]phenol

Step 1: 2-isopropyl-3-(4-methoxyphenyl)-7-methyl-2H-indazole

Prepared according to Method D step B from 3-(4-methoxyphenyl)-7-methyl-1H-indazole (0.115 g, 0.5 mmol), sodium hydride (60% in oil, 0.024 g, 0.6 mmol) and 2-iodopropane (0.10 mL, 1.0 mmol) to give the title compound (0.01 g) as a white solid.

Step 2:
4-[2-isopropyl-7-methyl-1H-indazol-3-yl]phenol

Prepared according to Method D step C from 2-isopropyl-3-(4-methoxyphenyl)-7-methyl-1H-indazole (0.010 g, 0.035 mmol), boron tribromide (0.05 mL, 0.5 mmol) and 0.2 mL of cyclohexene to give the product (0.007 g).
MS (ESI) m/z 267 ([M+H]$^+$);
RT=6.32 min

EXAMPLE 41

4-(7-chloro-1-pentyl-1H-indazol-3-yl)phenol

Step 1:
7-chloro-3-(4-methoxyphenyl)-1-pentyl-1H-indazole

Prepared according to Method D step B from 7-chloro-3-(4-methoxyphenyl)-1H-indazole (0.129 g, 0.5 mmol), sodium hydride (60% in oil, 0.024 g, 0.6 mmol) and 1-iodopentane (0.130 mL, 1.0 mmol) to give the title compound (0.072 g) as a white solid.
$^1$H NMR (DMSO-d$_6$): δ 0.838 (t, 3H), 1.301 (m, 4H), 1.84 (m, 2H), 3.817 (s, 3H), 4.72 (t, 2H), 7.08 (d, 2H), 7.18 (t, 1H), 7.50 (dd, 1H), 7.83 (d, 2H), 7.97 (dd, 1H).
MS (APCI) m/z 329 ([M+H]$^+$);

Step 2: 4-(7-chloro-1-pentyl-1H-indazol-3-yl)phenol

Prepared according to Method D step C from 7-chloro-3-(4-methoxyphenyl)-1-pentyl-1H-indazole (0.070 g, 0.23 mmol), boron tribromide (0.094 mL, 1.0 mmol) and 0.3 mL of cyclohexene to give the product (0.047 g) as an off-white solid.
$^1$H NMR (DMSO-d$_6$): δ 0.837 (t, 3H), 1.297 (m, 4H), 1.88 (m, 2H), 4.7087 (t, 2H), 6.90 (d, 2H), 7.15 (t, 1H), 7.48 (d, 1H), 7.71(d, 2H), 7.95 (d, 1H), 9.68 (s, 1H).
MS (APCI) m/z 315 [M+H]+.

EXAMPLE 42

4-[7-chloro-2-pentyl-2H-indazol-3-yl]phenol

Step 1:
7-chloro-3-(4-methoxyphenyl)-2-pentyl-2H-indazole

Prepared according to Method D step B from 7-chloro-3-(4-methoxyphenyl)-1H-indazole (0.129 g, 0.5 mmol), sodium hydride (60% in oil, 0.024 g, 0.6 mmol) and 1-iodopentane (0.130 mL, 1.0 mmol) to give the title compound (0.015 g).

Step 2: 4-[7-chloro-2-pentyl-2H-indazol-3-yl]phenol

Prepared according to Method D step C from 7-chloro-3-(4-methoxyphenyl)-2-pentyl-2H-indazole (0.015 g, 0.045 mmol), boron tribromide (0.05 mL, 0.5 mmol) and 0.2 mL of cyclohexene to give the product (0.007 g).
MS (ESI) m/z315 [M+H]+.
RT=7.3 min

EXAMPLE 43

4-(7-chloro-1-propyl-1H-indazol-3-yl)phenol

Step 1:
7-chloro-3-(4-methoxyphenyl)-1-propyl-1H-indazole

Prepared according to Method D step B from 7-chloro-3-(4-methoxyphenyl)-1H-indazole (0.129 g, 0.5 mmol), sodium hydride (60% in oil, 0.024 g, 0.6 mmol) and 1-iodopropane (0.098 mL, 1.0 mmol) to give the title compound (0.081 g) as a white solid.
$^1$H NMR (DMSO-d$_6$): δ 0.8896 (t, 3H), 1.864 (m, 2H), 3.819 (s, 3H), 4.7004 (t, 2H), 7.08 (d, 2H), 7.184 (t, 1H), 7.5 (d, 1H), 7.84 (d, 2H), 7.97 (d, 1H).
MS (ESI) m/z 301 [M+H]+.
Anal. calcd for C$_{17}$H$_{17}$ClN$_2$O: C, 67.88; H, 5.70; N, 9.31. Found: C, 67.78; H, 5.58; N, 9.06.

Step 2:
4-(7-chloro-1-propyl-1H-indazol-3-yl)phenol

Prepared according to Method D step C from 7-chloro-3-(4-methoxyphenyl)-1-propyl-1H-indazole (0.081 g, 0.26 mmol), boron tribromide (0.094 mL, 1.0 mmol) and 0.3 mL of cyclohexene to give the product (0.057 g) as an off-white solid.
$^1$H NMR (DMSO-d$_6$): δ 0.880 (s, 3H), 1.85 (m, 2H), 4.68 (t, 2H), 6.90 (d, 2H), 7.16 (t, 1H), 7.49 (dd, 1H), 7.71 (d, 2H), 7.95 (dd, 1H), 9.67 (s, 1H).
MS (ESI) m/z 287 [M+H]+.
Anal. calcd for C$_{16}$H$_{15}$ClN$_2$O. 0.15 HCl: C, 65.76; H, 5.23; N, 9.59. Found: C, 65.76; H, 5.29 N, 9.45.

EXAMPLE 44

4-[7-chloro-2-propyl-2H-indazol-3-yl]phenol

Step 1:
7-chloro-3-(4-methoxyphenyl)-2-propyl-2H-indazole

Prepared according to Method D step B from 7-chloro-3-(4-methoxyphenyl)-1H-indazole (0.129 g, 0.5 mmol), sodium hydride (60% in oil, 0.024 g, 0.6 mmol) and 1-iodopropane (0.098 mL, 1.0 mmol) to give the title compound (0.013 g).

Step 2:
4-[7-chloro-2-propyl-2H-indazol-3-yl]phenol

Prepared according to Method D step C from 7-chloro-3-(4-methoxyphenyl)-2-propyl-2H-indazole (0.013 g, 0.043 mmol), boron tribromide (0.05 mL, 0.5 mmol) and 0.2 mL of cyclohexene to give the product (0.007 g).
$^1$H NMR (DMSO-d$_6$): δ 0.764 (t, 3H), 1.86 (m, 2H), 4.34 (t, 2H), 6.98 (m, 3H), 7.37 (m, 3H), 7.43 (d, 1H).
MS (ESI) m/z 287 [M+H]+.
Anal. calcd for C$_{16}$H$_{15}$ClN$_2$O: C, 67.02; H, 5.27; N, 9.77. Found: C, 66.47; H, 5.21; N, 9.20.

EXAMPLE 45

4-(7-chloro-1-isopropyl-1H-indazol-3-yl)pheno

Step 1: 7-chloro-1-isopropyl-3-(4-methoxyphenyl)-1H-indazole

Prepared according to Method D step B from 7-chloro-3-(4-methoxyphenyl)-1H-indazole (0.129 g, 0.5 mmol), sodium hydride (60% in oil, 0.024 g, 0.6 mmol) and 2-iodopropane (0.10 mL, 1.0 mmol) to give the title compound (0.043 g) as a white solid.
$^1$H NMR (DMSO-d$_6$): δ 1.54 (d, 6H), 3.819 (s, 3H), 5.68 (m, 1H), 7.08 (d, 2H), 7.179 (t, 1H), 7.49 (dd, 1H), 7.83 (d, 2H), 7.96 (dd, 1H).
MS (APCI) m/z 301 [M+H]+.

Step 2:
4-(7-chloro-1-isopropyl-1H-indazol-3-yl)phenol

Prepared according to Method D step C from 7-chloro-1-isopropyl-3-(4-methoxyphenyl)-1H-indazole (0.093 g, 0.30 mmol), boron tribromide (0.094 mL, 1.0 mmol) and 0.3 mL of cyclohexene to give the product (0.025 g) as an off-white solid.
$^1$H NMR (DMSO-d$_6$): δ 1.54 (d, 6H), 5.66 (m, 1H), 6.90 (d, 2H), 7.15 (t, 1H), 7.47 (d, 1H), 7.715 (d, 2H), 7.94 (dd, 1H), 9.6 (broad s, 1H).
MS (APCI) m/z 287 [M+H]+.

EXAMPLE 46

4-(7-chloro-2-isopropyl-2H-indazol-3-yl)phenol

Step 1: 7-chloro-2-isopropyl-3-(4-methoxyphenyl)-2H-indazole

Prepared according to Method D step B from 7-chloro-3-(4-methoxyphenyl)-1H-indazole (0.129 g, 0.5 mmol), sodium hydride (60% in oil, 0.024 g, 0.6 mmol) and 2-iodopropane (0.10 mL, 1.0 mmol) to give the title compound (0.016 g).

Step 2: 4-(7-chloro-2-isopropyl-1H-indazol-3-yl)phenol

Prepared according to Method D step C from 7-chloro-2-isopropyl-3-(4-methoxyphenyl)-2H-indazole (0.016 g, 0.05 mmol), boron tribromide (0.050 mL, 0.5 mmol) and 0.2 mL of cyclohexene to give the product (0.006 g).
MS (ESI) m/z 287 [M+H]+.
RT=6.5 min

EXAMPLE 47

4-[1-pentyl-7-(trifluoromethyl)-1H-indazol-3-yl]phenol

Step 1: 3-(4-methoxyphenyl)-7-trifluoromethyl-1-pentyl-1H-indazole

Prepared according to Method D step B from 3-(4-methoxyphenyl)-7-trifluoromethyl-1H-indazole (0.146 g, 0.5 mmol), sodium hydride (60% in oil, 0.024 g, 0.6 mmol) and 1-iodopentane (0.130 mL, 1.0 mmol) to give the title compound (0.068 g) as a white solid.
$^1$H NMR (DMSO-$d_6$): δ 0.857 (t, 3H), 1.325 (m, 4H), 1.852 (m, 2H), 3.828 (s, 3H), 4.458 (t, 2H), 7.10 (d, 2H), 7.35 (t, 1H), 7.84 (d, 2H), 7.87 (d, 1H), 8.32 (dd, 1H).
MS (APCI) m/z 363 [M+H]+.

Step 2: 4-[1-pentyl-7-(trifluoromethyl)-1H-indazol-3-yl]phenol

Prepared according to Method D step C from 3-(4-methoxyphenyl)-1-pentyl-7-trifluoromethyl-1H-indazole (0.068 g, 0.19 mmol), boron tribromide (0.094 mL, 1.0 mmol) and 0.3 mL of cyclohexene to give the product (0.032 g) as an off-white solid.
$^1$H NMR (DMSO-$d_6$): δ 0.8553 (t, 3H), 1.3208 (m, 4H), 1.843 (m, 2H), 4.4426 (t, 2H), 6.92 (d, 2H), 7.338 (t, 1H), 7.72 (d, 2H), 7.87 (d, 1H), 8.30 (d, 1H), 9.728 (s, 1H).
MS (APCI) m/z 349 [M+H]+.

EXAMPLE 48

4-[1-propyl-7-(trifluoromethyl)-1H-indazol-3-yl]phenol

Step 1: 3-(4-methoxyphenyl)-7-trifluoromethyl-1-propyl-1H-indazole

Prepared according to Method D step B from 3-(4-methoxyphenyl)-7-trifluoromethyl-1H-indazole (0.146 g, 0.5 mmol), sodium hydride (60% in oil, 0.024 g, 0.6 mmol) and 1-iodopropane (0.098 mL, 1.0 mmol) to give the title compound (0.058 g) as a white solid.
$^1$H NMR (DMSO-$d_6$): δ 0.9138 (t, 3H), 1.868 (m, 2H), 3.828 (s, 3H), 4.43 (t, 2H), 7.10 (d, 2H), 7.36 (t, 1H), 7.85 (d, 2H), 7.89 (d, 1H), 8.32 (d, 1H).
MS (APCI) m/z 335 [M+H]+.

Step 2: 4-[1-propyl-7-(trifluoromethyl)-1H-indazol-3-yl]phenol

Prepared according to Method D step C from 3-(4-methoxyphenyl)-1-propyl-7-trifluoromethyl-1H-indazole (0.058 g, 0.17 mmol), boron tribromide (0.094 mL, 1.0 mmol) and 0.3 mL of cyclohexene to give the product (0.047 g) as an off-white solid.
$^1$H NMR (DMSO-$d_6$): δ 0.9065 (t, 3H), 1.85 (m, 2H), 4.413 (t, 2H), 6.92 (d, 2H), 7.34 (t, 1H), 7.72 (d, 2H), 7.87 (d, 1H), 8.30 (d, 1H), 9.75 (s, 1H).
MS (APCI) m/z 321 [M+H]+.

EXAMPLE 49

4-[1-isopropyl-7-(trifluoromethyl)-1H-indazol-3-yl]phenol

Step 1: 3-(4-methoxyphenyl)-7-trifluoromethyl-1-isopropyl-1H-indazole

Prepared according to Method D step B from 3-(4-methoxyphenyl)-7-trifluoromethyl-1H-indazole (0.146 g, 0.5 mmol), sodium hydride (60% in oil, 0.024 g, 0.6 mmol) and 2-iodopropane (0.10 mL, 1.0 mmol) to give the title compound (0.043 g) as a white solid.
$^1$H NMR (DMSO-$d_6$): δ 1.54 (d, 6H), 3.82 (s, 3H), 5.00 (m, 1H), 7.10 (d, 2H), 7.351 (t, 1H), 7.51 (d, 1H), 7.84 (d, 2H), 7.89 (d, 1H).
MS (APCI) m/z 335 [M+H]+.

Step 2: 4-[1-isopropyl-7-(trifluoromethyl)-1H-indazol-3-yl]phenol

Prepared according to Method D step C from 3-(4-methoxyphenyl)-1-isopropyl-7-trifluoromethyl-1H-indazole (0.043 g, 0.13 mmol), boron tribromide (0.094 mL, 1.0 mmol) and 0.3 mL of cyclohexene to give the product (0.032 g) as an off-white solid, mp 156–157° C.
$^1$H NMR (DMSO-$d_6$): δ 1.53 (d, 6H), 4.97 (m, 1H), 6.925 (d, 2H), 7.33 (t, 1H), 7.725 (d, 2H), 7.86 (d, 1H), 8.29 (d, 1H), 9.71 (s, 1H).
MS (APCI) m/z 321 [M+H]+.
MS (ESI) m/z 319 [M−H]−.
Anal. calcd for $C_{17}H_{15}F_3N_2O$: C, 63.75; H, 4.72 ; N, 8.75. Found: C, 63.15; H, 4.77 ; N, 8.48.

EXAMPLE 50

4-(1-allyl-7-fluoro-1H-indazol-3-yl)phenol

Step 1: 1-allyl-7-fluoro-3-(4-methoxyphenyl)-1H-indazole

Prepared according to Method D step B from 7-fluoro-3-(4-methoxyphenyl)-1H-indazole (0.108 g, 0.44 mmol), sodium hydride (60% in oil, 0.018 g, 0.45 mmol) and allylbromide (0.043 mL, 0.5 mmol) to give the title compound (0.085 g) as a white solid.
$^1$H NMR (DMSO-$d_6$): δ 3.8 (s, 3H), 4.97 (d, 1H, J=17.083 Hz), 5.17 (m, 3H), 6.08 (m, 1H), 7.08 (dd, 2H), 7.16 (m, 1H), 7.24 (m, 1H), 7.88 (m, 3H).
MS (APCI) m/z 283 [M+H]+.

Step 2: 4-(1-allyl-7-fluoro-1H-indazol-3-yl)phenol

Prepared according to Method D step C from 1-allyl-3-(4-methoxyphenyl)-7-trifluoromethyl-1H-indazole (0.070 g, 0.25 mmol), boron tribromide (0.094 mL, 1.0 mmol) and 0.3 mL of cyclohexene to give the product (0.055 g) as a tan solid.

$^1$H NMR (DMSO-d$_6$): δ 4.95 (d, 1H, J=17.79 Hz), 5.13 (m, 3H), 6.08 (m, 1H), 6.90(dd, 2H), 7.15 (m, 1H), 7.28 (m, 1H), 7.75 (d, 2H), 7.81 (d, 1H).
MS (APCI) m/z 269 [M+H]+.

EXAMPLE 51

4-(7-chloro-1-cyclopentyl-1H-indazol-3-yl)phenol

Step 1: 7-chloro-1-cyclopentyl-3-(4-methoxyphenyl)-1H-indazole

Prepared according to Method D step B from 7-chloro-3-(4-methoxyphenyl)-1H-indazole (0.129 g, 0.5 mmol), sodium hydride (60% in oil, 0.024 g, 0.6 mmol) and cyclopentylbromide (0.107 mL, 1.0 mmol) to give the title compound (0.080 g) as a white solid.

$^1$H NMR (DMSO-d$_6$): δ 1.70 (m, 2H), 1.88 (m, 2H), 3.817 (s, 3H), 5.821 (m, 1H), 7.08 (d, 2H), 7.17 (t, 1H), 7.49 (d, 1H), 7.83 (d, 2H), 7.97 (d, 1H).
MS (APCI) m/z 327 [M+H]+.

Step 2: 4-(7-chloro-1-cyclopentyl-1H-indazol-3-yl)phenol

Prepared according to Method D step C from 7-chloro-1-cyclopentyl-3-(4-methoxyphenyl)-methyl-1H-indazole (0.063 g, 0.19 mmol), boron tribromide (0.10 mL, 1.05 mmol) and 0.3 mL of cyclohexene to give the product (0.048 g) as an off-white solid.

$^1$H NMR (DMSO-d$_6$): δ 1.69 (m, 2H), 1.88 (m, 2H), 2.13 (m, 4H), 5.808 (m, 1H), 6.89 (d, 2H), 7.15 (t, 1H), 7.47 (d, 1H), 7.715 (d, 2H), 7.95 (d, 1H), 9.669 (broad s, 1H).
MS (ESI) m/z 313 [M+H]+.
Anal. calcd for $C_{18}H_{17}ClN_2O \cdot 0.50$; $H_2O$: C, 67.18; H, 5.64; N, 8.70. Found: C, 67.13; H, 5.28; N, 8.47.

EXAMPLE 52

4-(7-chloro-2-cyclopentyl-2H-indazol-3-yl)phenol

Step 1: 7-chloro-2-cyclopentyl-3-(4-methoxyphenyl)-2H-indazole

Prepared according to Method D step B from 7-chloro-3-(4-methoxyphenyl)-1H-indazole (0.129 g, 0.5 mmol), sodium hydride (60% in oil, 0.024 g, 0.6 mmol) and cyclopentylbromide (0.107 mL, 1.0 mmol) to give the title compound (0.004 g).
MS (ESI) m/z 327 ([M+H]$^+$)

Step 2: 4-(7-chloro-2-cyclopentyl-2H-indazol-3-yl)phenol

Prepared according to Method D step C from 7-chloro-2-cyclopentyl-3-(4-methoxyphenyl)-methyl-2H-indazole (0.004 g, 0.012 mmol), boron tribromide (0.10 mL, 1.05 mmol) and 0.3 mL of cyclohexene to give the product (0.004 g).
MS (ESI) m/z 313 [M+H]+.
RT=9.64 min

EXAMPLE 53

4-(7-fluoro-1-propyl-1H-indazol-3-yl)phenol

Step 1: 7-fluoro-3-(4-methoxyphenyl)-1-propyl-1H-indazole

Prepared according to Method D step B from 7-fluoro-3-(4-methoxyphenyl)-1H-indazole (0.121 g, 0.5 mmol), sodium hydride (60% in oil, 0.024 g, 0.6 mmol) and 1-iodopropane (0.096 mL, 1.0 mmol) to give the title compound (0.074 g) as a white solid.

$^1$H NMR (DMSO-d$_6$): δ 0.835 (t, 3H), 1.87 (q, 2H), 3.81 (t, 3H), 4.475 (t, 2H), 7.075 (d, 2H), 7.16 (m, 1H), 7.227 (m, 1H), 7.84 (m, 3H).
MS (APCI) m/z 285 [M+H]+.

Step 2: 4-(7-fluoro-1-propyl-1H-indazol-3-yl)phenol

Prepared according to Method D step C from 1-propyl-7-fluoro-3-(4-methoxyphenyl)-methyl-1H-indazole (0.051 g, 0.197 mmol), boron tribromide (0.10 mL, 1.05 mmol) and 0.3 mL of cyclohexene to give the product (0.051 g) as an off-white solid.

$^1$H NMR (DMSO-d$_6$): δ 0.852 (t, 3H), 1.86 (m, 2H), 4.458 (t, 2H), 6.9 (d, 2H), 7.13 (m, 1H), 7.21 (m, 1H), 7.73 (d, 2H), 7.80 (d, 1H), 9.667 (s, 1H).
MS (ESI) m/z 271 [M+H]+.

EXAMPLE 54

4-(7-fluoro-2-propyl-2H-indazol-3-yl)phenol

Step 1: 7-fluoro-3-(4-methoxyphenyl)-2-propyl-2H-indazole

Prepared according to Method D step B from 7-fluoro-3-(4-methoxyphenyl)-1H-indazole (0.121 g, 0.5 mmol), sodium hydride (60% in oil, 0.024 g, 0.6 mmol) and 1-iodopropane (0.096 mL, 1.0 mmol) to give the title compound (0.006 g).

Step 2: 4-(7-fluoro-2-propyl-1H-indazol-3-yl)phenol

Prepared according to Method D step C from 2-propyl-7-fluoro-3-(4-methoxyphenyl)-methyl-2H-indazole (0.006 g, 0.021 mmol), boron tribromide (0.05 mL, 0.5 mmol) and 0.2 mL of cyclohexene to give the product (0.0006 g).
MS (ESI) m/z 271 [M+H]+.

EXAMPLE 55

4-(7-fluoro-1-isopropyl-1H-indazol-3-yl)phenol

Step 1: 7-fluoro-1-isopropyl-3-(4-methoxyphenyl)-1H-indazole

Prepared according to Method D step B from 7-fluoro-3-(4-methoxyphenyl)-1H-indazole (0.121 g, 0.5 mmol), sodium hydride (60% in oil, 0.024 g, 0.6 mmol) and 2-iodopropane (0.10 mL, 1.0 mmol) to give the title compound (0.088 g) as a white solid.

$^1$H NMR (DMSO-d$_6$): δ 1.54 (d, 6H), 3.81 (s, 3H), 5.085 (m, 1H), 7.075 (d, 2H), 7.159 (m, 1H), 7.222 (m, 1H), 7.845 (m, 3H).
MS (APCI) m/z 285 [M+H]+.

Step 2:
4-(7-fluoro-1-isopropyl-1H-indazol-3-yl)phenol

Prepared according to Method D step C from 7-fluoro-1-isopropyl-3-(4-methoxyphenyl)-methyl-1H-indazole (0.065 g, 0.23 mmol), boron tribromide (0.10 mL, 1.05 mmol) and 0.3 mL of cyclohexene to give the product (0.047 g) as an off-white solid.

$^1$H NMR (DMSO-$d_6$): δ 1.53 (d, 6H), 5.069 (m, 1H), 6.90 (d, 2H), 7.14 (m, 1H), 7.24 (m, 1H), 7.73 (d, 2H), 7.78 (d 1H), 9.663 (broad s, 1H).
MS (ESI) m/z 271 [M+H]+.

EXAMPLE 56

4-(7-fluoro-2-isopropyl-2H-indazol-3-yl)phenol

Step 1: 7-fluoro-2-isopropyl-3-(4-methoxyphenyl)-2H-indazole

Prepared according to Method D step B from 7-fluoro-3-(4-methoxyphenyl)-1H-indazole (0.121 g, 0.5 mmol), sodium hydride (60% in oil, 0.024 g, 0.6 mmol) and 2-iodopropane (0.10 mL, 1.0 mmol) to give the title compound (0.007 g).

Step 2:
4-(7-fluoro-2-isopropyl-2H-indazol-3-yl)phenol

Prepared according to Method D step C from 7-fluoro-2-isopropyl-3-(4-methoxyphenyl)-methyl-2H-indazole (0.007 g, 0.025 mmol), boron tribromide (0.05 mL, 0.5 mmol) and 0.2 mL of cyclohexene to give the product (0.006 g).
MS (ESI) m/z 271 [M+H]+.

EXAMPLE 57

4-(1-allyl-7-methyl-1H-indazol-3-yl)phenol

Step 1:
1-allyl-3-(4-methoxyphenyl)-7-methyl-1H-indazole

Prepared according to Method D step B from 7-methyl-3-(4-methoxyphenyl)-1H-indazole (0.112 g, 0.5 mmol), sodium hydride (60% in oil, 0.024 g, 0.6 mmol) and allylbromide (0.086 mL, 1.0 mmol) to give the title compound (0.027 g) as a white solid. Used as is without further characterization.

Step 2: 4-(1-allyl-7-methyl-1H-indazol-3-yl)phenol

Prepared according to Method D step C from 1-allyl-3-(4-methoxyphenyl)-7-methyl-1H-indazole (0.027 g, 0.23 mmol), boron tribromide (0.10 mL, 1.05 mmol) and 0.3 mL of cyclohexene to give the product (0.020 g) as a tan solid.
$^1$H NMR (DMSO-$d_6$): δ 4.70 (dd, 1H), 5.10 (dd, 1H), 5.22 (m, 2H), 6.086 (m, 1H), 6.89 (d, 2H), 7.058 (t, 1H), 7.14 (d, 1H), 7.72 (d, 2H), 7.80 (d, 1H), 9.608 (s, 1H).
MS (ESI) m/z 265 [M+H]+.

EXAMPLE 58

4-[1-allyl-7-(trifluoromethyl)-1H-indazol-3-yl]phenol

Step 1:
1-allyl-3-(4-methoxyphenyl)-7-methyl-1H-indazole

Prepared according to Method D step B from 3-(4-methoxyphenyl)-7-trifluoromethyl-1H-indazole (0.146 g, 0.5 mmol), sodium hydride (60% in oil, 0.024 g, 0.6 mmol) and allylbromide (0.086 mL, 1.0 mmol) to give the title compound (0.027 g) as a white solid. Used as is without further characterization.

Step 2: 4-[1-allyl-7-(trifluoromethyl)-1H-indazol-3-yl]phenol

Prepared according to Method D step C from 1-allyl-3-(4-methoxyphenyl)-7-trifluoromethyl-1H-indazole (0.027 g, 0.08 mmol), boron tribromide (0.10 mL, 1.05 mmol) and 0.3 mL of cyclohexene to give the product (0.024 g) as a grey solid.
$^1$H NMR (DMSO-$d_6$): δ 4.83 (dd, 1H), 5.12 (m, 3H), 6.04 (m, 1H), 6.93 (d, 2H), 7.36 (t, 1H), 7.73 (d, 2H), 7.885 (d, 1H), 8.32 (d, 1H), 9.74 (s, 1H).
MS (ESI) m/z 319 [M+H]+.

EXAMPLE 59

4-[2-allyl-7-(trifluoromethyl)-2H-indazol-3-yl]phenol

Step 1:
2-allyl-3-(4-methoxyphenyl)-7-methyl-2H-indazole

Prepared according to Method D step B from 3-(4-methoxyphenyl)-7-trifluoromethyl-1H-indazole (0.146 g, 0.5 mmol), sodium hydride (60% in oil, 0.024 g, 0.6 mmol) and allylbromide (0.086 mL, 1.0 mmol) to give the title compound (0.007 g) as a white solid.
MS (ESI) m/z 333 [M+H]$^+$ Step 2: 4-[2-allyl-7-(trifluoromethyl)-2H-indazol-3-yl]phenol Prepared according to Method D step C from 2-allyl-3-(4-methoxyphenyl)-7-trifluoromethyl-2H-indazole (0.007 g, 0.02 mmol), boron tribromide (0.10 mL, 1.05 mmol) and 0.3 mL of cyclohexene to give the product (0.007 g).
MS (ESI) m/z 319 [M+H]+.
RT=9.1 min

EXAMPLE 60

4-(1-cyclopentyl-7-fluoro-1H-indazol-3-yl)phenol

Step 1: 1-cyclopentyl-7-fluoro--3-(4-methoxyphenyl)-1H-indazole

Prepared according to Method D step B from 7-fluoro-3-(4-methoxyphenyl)-1H-indazole (0.94 g, 3.8 mmol), sodium hydride (60% in oil, 0.148 g, 3.7 mmol) and cyclopentyl-bromide (0.43 mL, 4.0 mmol) to give the title compound (0.80 g) as a white solid,
mp 70–71° C.
$^1$H NMR (DMSO-$d_6$): δ 1.69 (m, 2H), 1.882 (m, 2H), 2.132 (m, 4H), 3.814 (s, 3H), 5.252 (m, 1H), 7.07 (dd, 2H), 7.15 (m, 1H), 7.23 (m, 2H), 7.80 (d, 1H), 7.85(d, 2H)
MS (ESI) m/z 311 [M+H]+.

Step 2:
4-(1-cyclopentyl-7-fluoro-1H-indazol-3-yl)phenol

Prepared according to Method D step C from 1-cyclopentyl-7-fluoro-3-(4-methoxyphenyl)-1H-indazole (0.57 g, 1.83 mmol), boron tribromide (0.70 mL, 7.35 mmol) and 3 mL of cyclohexene to give the product (0.25 g) as a white solid.
mp 131° C.;

¹H NMR (DMSO-d₆, 500 MHz): δ 1.697 (m, 2H), 1.880 (m, 2H), 2.124 (m, 4H), 5.255 (m, 1H), 6.90 (d, 2H), 7.12 (m, 1H), 7.21 (m, 2H), 7.73 (d, 2H), 7.78 (d, 1H), 9.643 (s, 1H).

MS (ESI) m/z 297 [M+H]+.

Anal. calcd for $C_{18}H_{17}FN_2O$: C:72.96 H:5.78 N:9.45 Found: C:73.17 H:5.73 N:9.60.

EXAMPLE 61

4-(2-cyclopentyl-7-fluoro-2H-indazol-3-yl)phenol

Step 1: 2-cyclopentyl-7-fluoro-3-(4-methoxyphenyl)-2H-indazole

Prepared according to Method D step B from 7-fluoro-3-(4-methoxyphenyl)-1H-indazole (0.75 g, 3.1 mmol), sodium hydride (60% in oil, 0.124 g, 3.1 mmol) and cyclopentylbromide (0.36 mL, 3.3 mmol) to give the title compound (0.055 g) as a white solid.

Step 2: 4-(2-cyclopentyl-7-fluoro-2H-indazol-3-yl)phenol

Prepared according to Method D step C from 2-cyclopentyl-7-fluoro-3-(4-methoxyphenyl)-2H-indazole (0.055 g, 0.177 mmol), boron tribromide (0.70 mL, 0.74 mmol) and 0.3 mL of cyclohexene to give the product (0.03 g) as an amber solid.

¹H NMR (DMSO-d₆): δ 1.63 (m, 2H), 1.94 (m, 2H), 2.118 (m, 4H), 4.96 (m, 1H), 6.98 (m, 4H), 7.25 (d 1H), 7.36 (d, 2H), 9.925 (s, 1H).

MS (ESI) m/z 297 [M+H]+.

EXAMPLE 62

4-(7-fluoro-1-(3,3,3-trifluoropropyl)-1H-indazol-3-yl)phenol

Step 1: 7-chloro-3-(4-methoxyphenyl)-1-(3,3,3-trifluoropropyl)-1H-indazole

Prepared according to Method D step B from 7-chloro-3-(4-methoxyphenyl)-1H-indazole (0.108 g, 0.4 mmol), sodium hydride (60% in oil, 0.016 g, 0.4 mmol) and 3,3,3-trifluoropropyliodide (0.047 mL, 0.4 mmol) to give the title compound (0.008 g).

¹H NMR (DMSO-d₆): δ 2.95 (m, 2H), 3.82 (s, 3H), 5.03 (m, 1H), 7.09 (d, 2H), 7.22 (t, 1H), 7.55 (d, 1H), 7.84 (d, 2H), 7.99 (d, 1H).

MS (APCI) m/z 355 [M+H]+.

Step 2: 4-(7-fluoro-1-(3,3,3-trifluoropropyl)-1H-indazol-3-yl)phenol

Prepared according to Method D step C from 7-chloro-3-(4-methoxyphenyl)-1-(3,3,3-trifluoropropyl)-1H-indazole (0.008 g, 0.022 mmol), boron tribromide (0.05 mL, 0.5 mmol) and 0.2 mL of cyclohexene to give the product (0.004 g).

MS (ESI) m/z 339 [M–H]–.

EXAMPLE 63

4-(1-cyclopentyl-7-fluoro-1H-indazol-3-yl)-2-methylphenol

Step 1: 1-cyclopentyl-7-fluoro-3-(4-methoxy-3-methylphenyl)-1H-indazole

Prepared according to Method D step B from 7-fluoro-3-(4-methoxy-3-methylphenyl)-1H-indazole (0.76 g, 0.4 mmol), sodium hydride (60% in oil, 0.120 g, 3.0 mmol) cyclopentyl bromide (0.321 mL, 3.0 mmol) to give the title compound (0.75 g).

¹H NMR (DMSO-d₆): δ 1.70 (m, 2H), 1.88 (m, 2H), 2.13 (m, 4H), 3.842 (s, 3H), 5.26 (m, 1H), 7.06 (d, 1H), 7.14 (m, 1H), 7.23 (m, 1H), 7.69 (m, 2H), 7.81 (d, 1H)

MS (ESI) m/z 325 ([M+H]⁺).

Step 2: 4-(1-cyclopentyl-7-fluoro-1H-indazol-3-yl)-2-methylphenol

Prepared according to Method D step C from 1-cyclopentyl-7-fluoro-3-(4-methoxy-3-methylphenyl)-1H-indazole (0.70 g, 2.16 mmol), boron tribromide (0.82 mL, 8.6 mmol) and 1.0 mL of cyclohexene to give the product (0.15 g) as a white solid, mp 107° C.

¹H NMR (DMSO-d₆): δ 1.68 (m, 2H), 1.88 (m, 2H), 2.124 (m, 4H), 5.24 (m, 1H), 6.90 (d, 1H), 7.12 (m, 1H), 7.22 (m, 1H), 7.55 (dd, 1H), 7.60 (s, 1H), 7.79 (d, 1H), 9.540 (s, 1H).

MS (ESI) m/z 311 [M+H]+.

Anal. calcd for $C_{19}H_{19}FN_2O$: C, 73.53; H, 6.17 ; N, 9.03. Found: C, 73.31; H, 6.10 ; N, 8.90.

EXAMPLE 64

4-[l1-allyl-7-(trifluoromethyl)-1H-indazol-3-yl]benzene-1,3-diol

Step 1: 1-allyl-3-(2,4-dimethoxyphenyl)-7-(trifluoromethyl)-1H-indazole

Prepared according to Method D step B from 3-(2,4-methoxyphenyl)-7-trifluoromethyl-1H-indazole 0.52 g, 1.6 mmol), sodium hydride (60% in oil, 0.065 g, 1.6 mmol) and allyl bromide (0.138 mL, 1.6 mmol) to give the title compound (0.26 g) as a white solid.

¹H NMR (DMSO-d₆): δ 3.73 (s, 3H), 3.80 (s, 3H), 4.85 (dd, 1H, J=1.5 and 14.65), 5.1 (m, 3H), 5.97–6.05 (m, 1H), 6.39 (dd, 1H, J=2.32 and 6.14), 6.64 (s, 1H), 7.25 (t, 1H), 7.35 (d, 1H), 7.85–7.87 (m, 2H),).

MS (ESI) m/z 363 [M+H]+.

Step 2: 4-[-allyl-7-(trifluoromethyl)-1H-indazol-3-yl]benzene-1,3-diol

Prepared according to Method D step C from 1-allyl-3-(2,4-dimethoxyphenyl)-7-(trifluoromethyl)-1H-indazole (0.065 g, 0.18 mmol), boron tribromide (0.136 mL, 1.4 mmol) and 1.0 mL of cyclohexene to give the product (0.066 g) as a white solid.

mp 114–115° C.;

¹H NMR (DMSO-d₆): δ 4.87 (dd, 1H, J=1.37 and 17.10 Hz), 5.31–5.08 (m, 3H), 6.01–6.08 (m, H), 6.39 (dd, 1H, J=2.44 and 8.40 Hz), 6.46 (s, 1H), 7.30 (t, 1H), 3.78 (d, 1H), 7.85–7.87 (m, 1H), 8.14–8.19 (m, 1H), 9.59 (broad s, 1H), 9.82 (broad s, 1H)

MS (ESI) m/z 335 [M+H]+.

Anal. calcd for $C_{17}H_{13}F_3N_2O_2$: C, 61.08; H, 3.92 ; N, 8.38. Found: C, 61.02; H, 3.76 ; N, 8.28.

EXAMPLE 65

4-[1-isopropyl-7-(trifluoromethyl)-1H-indazol-3-yl]benzene-1,3-diol

Step 1: 3-(2,4-dimethoxyphenyl)-1-isopropyl-7-(trifluoromethyl)-1H-indazole

Prepared according to Method D step B from 3-(2,4-methoxyphenyl)-7-trifluoromethyl-1H-indazole (1.50 g, 4.65 mmol), sodium hydride (60% in oil, 0.195 g, 4.88 mmol) and 2-iodopropane (0.47 mL, 4.88 mmol) to give the title compound (0.55 g) as a white solid.

mp 128–129° C.;

$^1$H NMR (DMSO-d$_6$): δ 1.52 (d, 6H, J=6.4 Hz), 3.77 (s, 3H), 3.84 (s, 3H), 4.99 (m, 1H), 6.67 (dd, 1H, J=8.4 and 2.2 Hz), 6.75 (d, 1H, J=2.2 Hz), 7.25 (t, 1H, 7.8 Hz) 7.39 (d, 1H, J=8.4 Hz), 7.82 (d, 1H, J=7.3 Hz), 7.88 (d, 1H, J=8.1 Hz)

MS (ESI) m/z 365 [M+H]+.

Anal. calcd for C$_{19}$H$_{19}$F$_3$N$_2$O$_2$: C, 62.63; H, 5.26 ; N, 7.69. Found: C, 62.52; H, 5.28 ; N, 7.59.

Step 2: 4-[1-isopropyl-7-(trifluoromethyl)-1H-indazol-3-yl]benzene-1,3-diol

Prepared according to Method D step C from 3-(2,4-dimethoxyphenyl)-1-isopropyl-7-(trifluoromethyl)-1H-indazole (0.442 g, 1.2 mmol), boron tribromide (0.688 mL, 7.27 mmol) and 1.0 mL of cyclohexene to give the product (0.268 g) as an off-white solid.

mp 61–63° C.;

$^1$H NMR (DMSO-d$_6$): δ 1.52 (d, 6H, J=6.3 Hz), 4.99 (m, 1H), 6.39 (dd, 1H, J=8.3 and 2.3 Hz), 6.46 ( d, 1H, J=2.1 Hz), 7.28 (t, 1H, J=7.8 Hz), 7.40 (d, 1H, J=8.4 Hz), 7.85 (d, 1H, J=7.5 Hz), 8.15 (d, 1H, J=8.1 Hz), 9.58 (s, 1H), 9.88 (s, 1H)

MS (ESI) m/z 337 [M+H]+.

Anal. calcd for C$_{17}$H$_{15}$F$_3$N$_2$O$_2$.0.11 C$_4$H$_8$O$_2$.0.10H$_2$O: C, 60.23; H, 4.66 ; N, 8.05 . Found: C, 60.14; H, 4.51 ; N, 7.65

EXAMPLE 66

4-[1-cyclopentyl-7-(trifluoromethyl)-1H-indazol-3-yl] benzene-1,3-diol

Step 1: 1-cyclopentyl-3-(2,4-dimethoxyphenyl)-7-(trifluoromethyl)-1H-indazole Prepared according to Method D step B from 3-(2,4-methoxyphenyl)-7-trifluoromethyl-1H-indazole (2.00 g, 6.20 mmol), sodium hydride (60% in oil, 0.297 g, 7.44 mmol) and cyclopentyl bromide (1.00 mL, 9.30 mmol) to give the title compound (0.68 g) as a white solid, mp 79–80° C.;

$^1$H NMR (DMSO-d$_6$): δ 1.67 (m, 2H), 1.92 (m, 2H), 2.11 (m, 4H), 3.77 (s, 3H), 3.84 (s, 3H), 5.17 (m, 1H) 6.67 (dd, 1H, J=8.4 and 2.3 Hz), 6.74 (d, 1H, J=2.3 Hz), 7.25 (t, 1H, 7.7 Hz) 7.38 (d, 1H, J=8.4 Hz), 7.82 (d, 1H, J=7.3 Hz), 7.88 (d, 1H, J=8.1 Hz)

MS (EI) m/z 390([M+H]$^+$):;

Anal. calcd for C$_{21}$H$_{21}$F$_3$N$_2$O$_2$: C, 64.61; H, 5.42 ; N, 7.18. Found: C,64.55; H, 5.34 ; N, 7.20.

Step 2: 4-[1-cyclopentyl-7-(trifluoromethyl)-1H-indazol-3-yl]benzene-1,3-diol Prepared according to Method D step C from 1-cyclopentyl-3-(2,4-dimethoxyphenyl)-7-(trifluoromethyl)-1H-indazole (0.465 g, 1.2 mmol), boron tribromide (0.67 mL, 7.1 mmol) and 1.0 mL of cyclohexene to give the product (0.424 g) as an off-white solid.

mp 159–160° C.;

$^1$H NMR (DMSO-d$_6$): δ 1.70 (m, 2H), 1.92 (m, 2H), 2.07 (m, 2H), 2.13 (m, 2H), 5.18 (m 1H), 6.39 (dd, 1H, J=8.4 and 2.4 Hz), 6.46 (d, 1H, J=2.1 Hz), 7.27 (t, 1H, J=7.8 Hz), 7.39 (d, 1H, J=8.4 Hz), 7.84 (d, 1H, J=7.3 Hz), 8.14 (d, 1H, J=8.2 Hz), 9.58 (s, 1H), 9.87 (s, 1H)

MS (ESI) m/z 361 [M−H]−.

Anal. calcd for C$_{19}$H$_{17}$F$_3$N$_2$O$_2$: C, 62.98; H, 4.73 ; N, 7.73. Found: C, 62.64; H, 4.57 ; N, 7.47.

EXAMPLE 67

4-[1-(cyclohexylmethyl)-7-(trifluoromethyl)-1H-indazol-3-yl]benzene-1,3-diol

Step 1: 1-Cyclohexylmethyl-3-(2,4-dimethoxyphenyl)-7-trifluoromethyl-1H-indazole Prepared according to Method D step B from 3-(2,4-methoxyphenyl)-7-trifluoromethyl-1H-indazole (1.82 g, 5.64 mmol), sodium hydride (60% in oil, 0.451 g, 11.28 mmol) and (bromomethyl)cyclohexane (4.00 g, 22.5 mmol) to give the title compound (0.804 g) as a white solid.

$^1$H NMR (DMSO-d$_6$): δ 1.02 (m, 2H), 1.14 (m, 4H), 1.55 (m, 2H), 1.65 (m, 2H), 1.96 (m, 4H), 3.77 (s, 3H), 3.84 (s, 3H), 4.29 (d, 2H, J=7.0 Hz), 6.67 (dd, 1H, J=8.4 and 2.2 Hz), 6.75 (d, 1H, J=2.1 Hz), 7.26 (t, 1H, 7.7 Hz) 7.37 (d, 1H, J=8.4 Hz), 7.83 (d, 1H, J=7.3 Hz), 7.89 (d, 1H, J=7.9 Hz)

MS (ESI) m/z419 [M+H]+.

Anal. calcd for C$_{23}$H$_{25}$F$_3$N$_2$O$_2$: C, 66.02; H, 6.02 ; N, 6.69. Found: C, 66.24; H, 6.22 ; N, 6.34.

Step 2: 4-[1-(cyclohexylmethyl)-7-(trifluoromethyl)-1H-indazol-3-yl]benzene-1,3-diol Prepared according to Method D step C from 1-(cyclohexylmethyl)-3-(2,4-dimethoxy-phenyl)-7-(trifluoromethyl)-1H-indazole (0.841 g, 2.0 mmol), boron tribromide (1.14 mL, 12 mmol) and 0.5 mL of cyclohexene to give the product (0.567 g) as an off-white solid.

mp 117–118° C.;

$^1$H NMR (DMSO-d$_6$): δ 1.02 (m, 2H), 1.13 (m, 3H), 1.52 (m, 2H), 1.64 (m, 3H 1.97 (m, 1H), 4.29 (d, 2H J=7.2 Hz), 6.39 (dd, 1H, J=8.4 and 2.4 Hz), 6.46 (d, 1H, J=2.1 Hz), 7.28 (t, 1H, J=7.8 Hz), 7.38 (d, 1H, J=8.4 Hz), 7.85 (d, 1H, J=7.3 Hz), 8.15 (d, 1H, J=8.2 Hz), 9.59 (s, 1H), 9.87 (s, 1H).

MS (ESI) m/z 389 [M−H]−.

Anal. calcd for C$_{21}$H$_{21}$F$_3$N$_2$O$_2$.0.05 C$_6$H$_{14}$: C, 64.82; H, 5.54; N, 7.10; Found: C, 65.14; H, 5.55; N, 7.18.

EXAMPLE 68

4-[1-isobutyl-7-(trifluoromethyl)-1H-indazol-3-yl]benzene-1,3-diol

Step 1: 1-isobutyl-3-(2,4-dimethoxyphenyl)-7-trifluoromethyl-1H-indazole

Prepared according to Method D step B from 3-(2,4-methoxyphenyl)-7-trifluoromethyl-1H-indazole (2.00 g, 6.20 mmol), sodium hydride (60% in oil, 0.297 g, 7.44 mmol) and 1-Iodo-2-Methylpropane (1.07 mL, 9.30 mmol) to give the title compound (0.708 g) as a white solid.

$^1$H NMR (DMSO-d$_6$): δ 0.88 (d, 6H, J=6.72 Hz), 2.28 (m, 1H), 3.77 (s, 3H), 3.84 (s, 3H), 4.27 (d, 2H, J=7.3 Hz), 6.67 (dd, 1H, J=8.4 and 2.2 Hz), 6.75 (d, 1H, J=2.1 Hz), 7.27 (t, 1H, 7.8 Hz) 7.38 (d, 1H, J=8.4 Hz), 7.84 (d, 1H, J=7.3 Hz), 7.89 (d, 1H, J=8.0 Hz)

MS (ESI) m/z 379 [M+H]+.

Anal. calcd for C$_{20}$H$_{21}$F$_3$N$_2$O$_2$: C, 63.48; H, 5.59; N, 7.40; Found: C, 63.35; H, 5.56; N, 7.20.

Step 2: 4-[1-isobutyl-7-(trifluoromethyl)-1H-indazol-3-yl]benzene-1,3-diol

Prepared according to Method D step C from 3-(2,4-dimethoxyphenyl)-1-isobutyl-7-(trifluoromethyl)-1H-indazole (0.675 g, 1.2 mmol), boron tribromide (1.01 mL, 10.7 mmol) and 1.0 mL of cyclohexene to give the product (0.208 g) as an off-white solid.
mp 91–92° C.;
$^1$H NMR (DMSO-$d_6$): δ 0.88 (d, 6H, J=6.6 Hz), 2.27 (m, 1H), 4.26 (d, 2H, J=7.2 Hz) 6.39 (dd, 1H, J=8.4 and 2.4 Hz), 6.46 (d, 1H, J=2.1 Hz), 7.28 (t, 1H, J=7.8Hz), 7.38 (d, 1H, J=8.4 Hz), 7.85 (d, 1H, J=7.3 Hz), 8.15 (d, 1H, J=8.2 Hz), 9.59 (s, 1H), 9.85 (s, 1H)
MS (ESI) m/z 351 [M+H]+.
Anal. calcd for $C_{18}H_{17}F_3N_2O_2$: C, 61.71; H, 4.89; N, 8.00; Found: C, 61.60; H, 4.98; N, 7.84.

EXAMPLE 69

4-[1-(2-ethylbutyl)-7-(trifluoromethyl)-1H-indazol-3-yl]benzene-1,3-diol

Step 1: 3-(2,4-dimethoxyphenyl)-1-(2-ethylbutyl)-7-(trifluoromethyl)-1H-indazole Prepared according to Method D step B from 3-(2,4-methoxyphenyl)-7-trifluoromethyl-1H-indazole (2.00 g, 6.20 mmol), sodium hydride (60% in oil, 0.496 g, 12.4 mmol) and 1-Bromo-2-Ethylbutane (3.07 g, 18.6 mmol) to give the title compound (0.748 g) as a white solid.
$^1$H NMR (DMSO-$d_6$): δ 0.82 (t, 6H, J=7.5 Hz), 1.30 (m, 4H), 2.05 (m, 1H), 3.77 (s, 3H), 3.84 (s, 3H), 4.35 (d, 2H, J=7.3 Hz), 6.67 (dd, 1H, J=8.4 and 2.4 Hz), 6.75 (d, 1H, J=2.2 Hz), 7.27 (t, 1H, 7.6 Hz) 7.36 (d, 1H, J=8.4 Hz), 7.84 (d, 1H, J=7.3 Hz), 7.89 (d, 1H, J=8.3 Hz).
MS (ESI) m/z 407 [M+H]+.
Anal. calcd for $C_{22}H_{25}F_3N_2O_2$: C, 65.01; H, 6.20; N, 6.89; Found: C, 65.01; H, 6.15; N, 6.75.

Step 2: 4-[1-(2-ethylbutyl)-7-(trifluoromethyl)-1H-indazol-3-yl]benzene-1.3-diol Prepared according to Method D step C from 3-(2,4-dimethoxyphenyl)-1-(2-ethylbutyl)-7-(trifluoromethyl)-1H-indazole (0.720 g, 1.77 mmol), boron tribromide (1.01 mL, 10.7 mmol) and 0.5 mL of cyclohexene to give the product (0.222 g) as an off-white solid.
mp 89–90° C.;
$^1$H NMR (DMSO-$d_6$): δ 0.82 (t, 6H, J=7.5 Hz), 1.29 (m, 4H), 2.04 (m, 1H), 4.35 (d, 2H J=7.5 Hz), 6.39 (dd, 1H, J=8.4 and 2.4 Hz), 6.46 (d, 1H, J=2.3 Hz), 7.28 (t, 1H, J=7.6 Hz), 7.38 (d, 1H, J=8.4 Hz), 7.85 (d, 1H, J=7.5 Hz), 8.16 (d, 1H, J=8.1 Hz), 9.59 (s, 1H), 9.85 (s, 1H).
MS (ESI) m/z 379 [M+H]+.
Anal. calcd for $C_{20}H_{21}F_3N_2O_2$: C, 63.48; H, 5.59; N, 7.40; Found: C, 63.59; H, 5.60; N, 7.31.

EXAMPLE 70

4-[1-cyclobutyl-7-(trifluoromethyl)-1H-indazol-3-yl]benzene-1,3-diol

Step 1: 1-cyclobutyl-3-(2,4-dimethoxyphenyl)-7-(trifluoromethyl)-1H-indazole Prepared according to Method D step B from 3-(2,4-methoxyphenyl)-7-trifluoromethyl-1H-indazole (2.38 g, 7.40 mmol), sodium hydride (60% in oil, 0.592 g, 14.8 mmol) and bromocyclobutane (3.00 g, 22.2 mmol) to give the title compound (0.643 g) as a white solid.
mp 109–110° C.;
$^1$H NMR (DMSO-$d_6$): δ 1.87 (m, 2H), 2.45 (m, 2H), 2.77 (m, 2H), 3.77 (s, 3H), 3.85 (s, 3H), 5.25 (m, 1H), 6.68 (dd, 1H, J=8.4 and 2.3 Hz), 6.76 (d, 1H, J=2.1Hz) 7.27 (t, 1H, 7.8 Hz), 7.43 (d, 1H, J=8.4 Hz), 7.83 (d, 1H, J=7.3 Hz), 7.87 (d, 1H, J=8.1 Hz).
MS (ESI) m/z 377 [M+H]+.
Anal. calcd for $C_{20}H_{19}F_3N_2O_2$.0.10 $C_6H_{14}$: C, 64.27; H, 5.34; N, 7.28; Found: C, 64.38; H, 5.12; N, 7.38.

Step 2: 4-[1-cyclobutyl-7-(trifluoromethyl)-1H-indazol-3-yl]benzene-1,3-diol Prepared according to Method D step C from 1-cyclobutyl-3-(2,4-dimethoxyphenyl)-7-(trifluoromethyl)-1H-indazole (0.575 g, 1.5 mmol), boron tribromide (0.866 mL, 9.1 mmol) and 0.5 mL of cyclohexene to give the product (0.214 g) as an off-white solid.
mp 124–125° C.;
$^1$H NMR (DMSO-$d_6$): δ 1.85 (m, 2H), 2.44 (m, 2H), 2.75 (m, 2H), 5.24 (m, 1H), 6.39 (dd, 1H, J=8.4 and 2.3 Hz), 6.47 (d, 1H, J=2.3 Hz), 7.28 (t, 1H, J=7.8 Hz), 7.39 (d, 1H, J=8.4 Hz), 7.83 (d, 1H, J=7.5 Hz), 8.10 (d, 1H, J=8.1 Hz), 9.58 (s, 1H), 9.81 (s, 1H).
MS (ESI) m/z 347 [M–H]–.
Anal. calcd for $C_{18}H_{15}F_3N_2O_2$: C, 62.07; H, 4.34; N, 8.04; Found: C, 61.61; H, 4.25; N, 7.93.

EXAMPLE 71

4-[1-(1-ethylpropyl)-7-(trifluoromethyl)-1H-indazol-3-yl]benzene-1,3-diol

Step 1: 3-(2,4-dimethoxyphenyl)-1-(1-ethylpropyl)-7-(trifluoromethyl)-1H-indazole Prepared according to Method D step B from 3-(2,4-methoxyphenyl)-7-trifluoromethyl-1H-indazole (2.50 g, 7.75 mmol), sodium hydride (60% in oil, 0.62 g, 15.5 mmol) and 3-Bromopentane (3.51 g, 23 mmol) to give the title compound (0.866 g) as a white solid.
mp 115–116° C.;
$^1$H NMR (DMSO-$d_6$): δ 0.68 (t, 6H, J=7.5 Hz), 1.90 (m, 2H), 2.00 (m, 2H), 3.78 (s, 3H), 3.84 (s, 3H), 4.51 (m, 1H), 6.67 (dd, 1H, J=8.4 and 2.1 Hz), 6.75 (d, 1H, J=2.1 Hz), 7.25 (t, 1H, 7.8 Hz), 7.37 (d, 1H, J=8.3 Hz), 7.82 (d, 1H, J=7.3 Hz), 7.89 (d, 1H, J=8.1 Hz).
MS (ESI) m/z 393 [M+H]+.
Anal. calcd for $C_{21}H_{23}F_3N_2O_2$: C, 64.28; H, 5.91; N, 7.14; Found: C, 64.21; H, 5.78; N, 7.10.

Step 2: 4-[1-(1-ethylpropyl)-7-(trifluoromethyl)-1H-indazol-3-yl]benzene-1.3-diol Prepared according to Method D step C from 3-(2,4-dimethoxyphenyl)-1-(1-ethylpropyl)-7-(trifluoromethyl)-1H-indazole (0.557 g, 1.42 mmol), boron tribromide (0.81 mL, 8.51 mmol) and 0.5 mL of cyclohexene to give the product (0.367 g) as an off-white solid.
mp 121–122° C.;
$^1$H NMR (DMSO-$d_6$): δ 0.67 (t, 6H, J=7.5 Hz), 1.91 (m, 2H), 1.98 (m, 2H), 4.51 (m, 1H), 6.39 (dd, 1H, J=8.4 and 2.3 Hz), 6.46 (d, 1H, J=2.3 Hz), 7.28 (t, 1H, J=7.6 Hz), 7.42 (d, 1H, J=8.4 Hz), 7.85 (d, 1H, J=7.3 Hz), 8.18 (d, 1H, J=8.1 Hz), 9.60 (s, 1H), 9.92 (s, 1H).
MS (ESI) m/z 365 [M+H]+.

Anal. calcd for $C_{19}H_{19}F_3N_2O_2$: C, 62.63; H, 5.26; N, 7.69; Found: C, 62.75; H, 5.12; N, 7.57.

EXAMPLE 72

4-[2-allyl-7-(trifluoromethyl)-2H-indazol-3-yl]-3-methylphenol

Step 1: 2-allyl-3-(4-methoxy-2-methylphenyl)-7-(trifluoromethyl)-2H-indazole

Prepared according to Method D step B from 3-(4-methoxy-2-methylphenyl)-7-(trifluoromethyl)-1H-indazole (0.150 g, 0.49 mmol), sodium hydride (60% in oil, 0.025 g, 1.04 mmol) and allyl bromide (0.07 mL, 0.74 mmol) to give the title compound (0.055 g) as a white solid.

$^1$H NMR (DMSO-$d_6$): δ 1.99 (s, 3H), 3.83 (s, 3H), 4.77–4.98 (m, 3H), 5.13 (dd, 1H, J=1.19 and 10.32 Hz), 5.88–6.01 (m, 1H), 6.95 (dd, 1H, J=2.58 and 8.53 Hz), 7.04 (s, 1H), 7.14 (t, 1H), 7.28 (d, 1H), 7.58 (d, 1H), 7.69 (d, 1H).
MS (ESI) m/z 347 [M+H]+.

Step 2: 4-[2-allyl-7-(trifluoromethyl)-2H-indazol-3-yl]-3-methylphenol

Prepared according to Method D step C from 2-allyl-3-(4-methoxy-2-methylphenyl)-7-(trifluoromethyl)-2H-indazole (0.043 g, 0.124 mmol), boron tribromide (0.05 mL, 0.52 mmol) and 1.0 mL of cyclohexene to give the product (0.033 g) as a white solid.

$^1$H NMR (DMSO-$d_6$): δ 1.93 (s, 3H), 4.77–4.82 (m, H), 4.88–4.96 (m, 2H), 5.12 (dd, 1H, J=1.37 and 10.38 Hz), 5.74–5.98 (m, 1H), 6.82 (s, 1H), 6.76 (dd, 1H, J=2.44 and 8.39), 7.12–7.15 (m, 1H), 7.58 (d, 1H), 7.67 (d, 1H), 9.81 (broad s, 1H).
MS (ESI) m/z 333 [M+H]+.

EXAMPLE 73

4-[1-pentyl-7-(trifluoromethyl)-1H-indazol-3-yl]benzen-1,3-diol

Step 1: 3-(2,4-dimethoxyphenyl)-1-pentyl-7-(trifluoromethyl)-1H-indazole

Prepared according to Method D step B from 3-(2,4-dimethoxyphenyl)-7-(trifluoromethyl)-1H-indazole (0.150 g, 0.49 mmol), sodium hydride (60% in oil, 0.025 g, 1.04 mmol) and 1-iodopentane (0.07 mL, 0.7 mmol) to give the title compound (0.069 g) as a white solid.

$^1$H NMR (DMSO-$d_6$): δ 0.83–0.88 (m, 2H), 1.22–1.37 (m, 4H), 1.81–1.86 (m, 2H), 3.74 (s, 3H), 3.83 (s, 3H), 6.66 (dd, 1H, J=2.18 and 8.33 Hz), 6.75 (s, 1H), 7.26 (t, 1H), 7.38 (d, 1H), 7.85 (m, 2H).
MS (ESI) m/z 393 [M+H]+.

Step 2: 4-[1-pentyl-7-(trifluoromethyl)-1H-indazol-3-yl]benzene-1,3-diol

Prepared according to Method D step C from 3-(2,4-dimethoxyphenyl)-1-pentyl-7-(trifluoromethyl)-1H-indazole (0.055 g, 0.14 mmol), boron tribromide (0.136 mL, 1.4 mmol) and 1.0 mL of cyclohexene to give the product (0.048 g) as a white solid.

$^1$H NMR (DMSO-$d_6$): δ 0.82–0.89 (m, 3H), 1.28–1.35 (m, 4H), 1.81–1.85 (m, 2H), 4.44 (t, 2H), 6.38 (dd, 1H, J=2.29 and 8.40 Hz), 6.46 (s, 1H), 7.28 (t, 1H), 7.38 (d, 1H), 7.85 (d, 1H), 8.13 (d, 1H), 9.59 (broad s, 1H), 9.83 (broad s, 1H).
MS (ESI) m/z 363 [M–H]–.

EXAMPLE 74

4-[1-allyl-7-(trifluoromethyl)-1H-indazol-3-yl]-3-methylphenol

Step 1: 1-allyl-3-(4-methoxy-2-methylphenyl)-7-(trifluoromethyl)-1H-indazole

Prepared according to Method D step B from 3-(4-methoxy-2-methylphenyl)-7-(trifluoromethyl)-1H-indazole (0.150 g, 0.49 mmol), sodium hydride (60% in oil, 0.025 g, 1.04 mmol) and allyl bromide (0.07 mL, 0.7 mmol) to give the title compound (0.090 g) as a white solid.

$^1$H NMR (DMSO-$d_6$): δ 2.27 (s, 3H), 3.81 (s, 1H), 4.76 (d, 1H), 5.10–5.14 (m, 3H), 6.01–6.08 (m, 1H), 6.90 (d, 1H), 6.98 (s, 1H), 7.30–7.39 (m, 2H), 7.87–7.90 (m, 2H).
MS (ESI) m/z 347 [M+H]+.

Step 2: 4-[1-allyl-7-(trifluoromethyl)-1H-indazol-3-yl]-3-methylphenol

Prepared according to Method D step C from 1-allyl-3-(4-methoxy-2-methylphenyl)-7-(trifluoromethyl)-1H-indazole (0.075 g, 0.22 mmol), boron tribromide (0.082 mL, 0.87 mmol) and 1.0 mL of cyclohexene to give the product (0.086 g) as a white solid.

$^1$H NMR (DMSO-$d_6$): δ 2.21 (s, 3H), 4.77 (d, 1H), 5.10–5.13 (m, 3H), 6.02–6.10 (m, 1H), 6.76 (dd, H, J=2.44 and 8.27 Hz), 6.78 (s, 1H), 7.25 (d, 1H), 7.32 (t, 1H), 7.86–7.89 (m, 2H), 9.60 (broad s1H).
MS (ESI) m/z 333 [M+H]+.

EXAMPLE 75

4-[2-allyl-7-(trifluoromethyl)-2H-indazol-3-yl]-1,3-benzenediol

Step 1: 2-allyl-3-(2,4-dimethoxyphenyl)-7-(trifluoromethyl)-2H-indazole

Prepared according to Method D step B from 3-(2,4-dimethoxyphenyl)-7-(trifluoro-methyl)-1H-indazole (0.150 g, 0.49 mmol), sodium hydride (60% in oil, 0.025 g, 1.04 mmol) and allyl bromide (0.07 mL, 0.7 mmol) to give the title compound (0.062 g) as a white solid.

$^1$H NMR (DMSO-$d_6$): δ 3.75 (s, 3H), 3.86 (s, 3H), 4.87–4.99 (m, 3H), 5.13 (d, 1H), 5.90–5.99 (m, 1H), 6.72 (d, 1H), 6.79 (s, 1H), 7.12 (t, 1H), 7.31 (d, 1H), 7.61–7.68 (m, 2H).
MS (ESI) m/z 363 [M+H]+.

Step 2: 4-[2-allyl-7-(trifluoromethyl)-2H-indazol-3-yl]-1,3-benzenediol

Prepared according to Method D step C from 2-allyl-3-(2,4-dimethoxyphenyl)-7-(trifluoromethyl)-2H-indazole (0.05 g, 0.14 mmol), boron tribromide (0.104 mL, 1.1 mmol) and 1.0 mL of cyclohexene to give the product (0.019 g) as a white solid.

$^1$H NMR (DMSO-$d_6$): δ 4.80–4.82 (dd, 1H, J=1.68 and 6.87 Hz), 4.83–5.01 (m, 2H), 5.12 (d, 1H), 5.93–6.02 (m, 1H), 6.38–6.45 (m, 1H), 6.50 (s, 1H), 7.00–7.70 (m, 2H), 7.65–7.66 (m, 2H), 9.72 (broad s, 1H), 9.88 (broad s, 1H).
MS (ESI) m/z 335 [M+H]+.
Anal. calcd for $C_{17}H_{13}F_3N_2O_2 \cdot 0.50\ C_6H_{14}$: C,63.65; H, 5.34; N, 7.42; Found: C, 63.67; H, 4.96; N, 7.26.

EXAMPLE 76

3-methyl-4-[1-propyl-7-(trifluoromethyl)-1H-indazol-3-yl]phenol

Step 1: 3-(4-methoxy-2-methylphenyl)-1-propyl-7-(trifluoromethyl)-1H-indazole Prepared according to Method D step B from 3-(4-methoxy-2-methylphenyl)-7-(trifluoromethyl)-1H-indazole (0.150 g, 0.49 mmol), sodium hydride (60% in oil, 0.025 g, 1.04 mmol) and iodopropane (0.07 mL, 0.7 mmol) to give the title compound (0.098 g) as a white solid.
$^1$H NMR (DMSO-$d_6$): δ 0.9 (t, 3H), 1.85–1.94 (m, 2H), 2.28 (s, 3H), 3.81 (s, 3H), 4.44 (t, 2H), 6.91 (dd, 1H, J=2.60–8.40 Hz), 6.98 (s, 1H), 7.30 (t, 1H), 7.38 (d, 1H), 7.88 (d, 1H)
MS (ESI) m/z349 [M+H]+.

Step 2: 3-methyl-4-[1-propyl-7-(trifluoromethyl)-1H-indazol-3-yl]phenol

Prepared according to Method D step C from 3-(4-methoxy-2-methylphenyl)-1-propyl-7-(trifluoromethyl)-1H-indazole (0.087 g, 0.25 mmol), boron tribromide (0.136 mL, 1.4 mmol) and 1.0 mL of cyclohexene to give the product (0.091 g) as a white solid,
$^1$H NMR (DMSO-$d_6$): δ 0.89 (t, 3H), 1.85–1.89 (m, 2H), 2.22 (s, 3H), 4.42 (t, 2H), 6.73 (dd, 1H, J=2.29 and 8.25 Hz), 6.78 (s, 1H), 725 (d, 1H), 7.29 (t, 1H), 7.86 (m, 1H), 9.58 (broad s, 1H).

EXAMPLE 77

4-(7-chloro-1-isopropyl-1H-indazol-3-yl)-3-methylphenol

Step 1: 7-chloro-1-isopropyl-3-(4-methoxy-2-methylphenyl)-1H-indazole

Prepared according to Method D step B from 7-chloro-3-(4-methoxy-2-methylphenyl)-1H-indazole (0.150 g, 0.52 mmol), sodium hydride (60% in oil, 0.025 g, 1.04 mmol) and 2-iodopropane (0.07 mL, 0.7 mmol) to give the title compound (0.100 g) as a white solid.
$^1$H NMR (DMSO-$d_6$): δ 1.5 (d, 6H), 1.3 (s, 3H), 3.80 (s, 3H), 5.66–5.68 (m, 1H), 6.90 (dd, 1H, J=2.59 and 8.39 Hz), 6.96 (s, 1H), 7.12 (t, 1H), 7.39 (d, 1H), 7.47 (d, 1H), 7.54 (d, 1H).
MS (ESI) m/z 315 [M+H]+.

Step 2: 4-(7-chloro-1-isopropyl-1H-indazol-3-yl)-3-methylphenol

Prepared according to Method D step C from 7-chloro-1-isopropyl-3-(4-methoxy-2-methylphenyl)-1H-indazole (0.090 g, 0.3 mmol), boron tribromide (0.104 mL, 1.1 mmol) and 1.0 mL of cyclohexene to give the product (0.048 g) as a white solid.

$^1$H NMR (DMSO-$d_6$): δ 1.52 (d, 6H), 2.23 (s, 3H), 5.63–5.69 (m, 1H), 6.72 (dd, 1H, J=2.44 and 8.24 Hz), 6.76 (s, 1H), 7.10 (t, 1H), 7.26 (d, 1H), 7.46 (d, 1H), 7.53 (d, 1H), 9.54 (broad s, 1H).
MS (ESI) m/z 301 [M+H]+.

EXAMPLE 78

4-(2-allyl-7-chloro-2H-indazol-3-yl)-3-methylphenol

Step 1: 2-allyl-7-chloro-3-(4-methoxy-2-methylphenyl)-2H-indazole

Prepared according to Method D step B from 7-chloro-3-(4-methoxy-2-methylphenyl)-1H-indazole (0.150 g, 0.52 mmol), sodium hydride (60% in oil, 0.025 g, 1.04 mmol) and 2-allyl bromide (0.07 mL, 0.7 mmol) to give the title compound (0.068 g) as a white solid.
$^1$H NMR (DMSO-$d_6$): δ 1.99 (s, 3H), 3.82 (s, 3H), 4.75–4.79 (m, 1H), 4.90–4.93 (m, 2H), 5.13 (m, 2H, J=0.916 and 10.23 Hz), 5.92–5.99 (m, 1H), 6.93–7.02 (m, 3H), 7.25 (t, 2H), 7.38 (d, 2H).
MS (ESI) m/z 313 [M+H]+.

Step 2: 4-(2-allyl-7-chloro-2H-indazol-3-yl)-3-methylphenol

Prepared according to Method D step C from 2-allyl-7-chloro-3-(4-methoxy-2-methylphenyl)-2H-indazole (0.068 g, 0.2 mmol), boron tribromide (0.20 mL, 2.10 mmol) and 1.0 mL of cyclohexene to give the product (0.065 g) as a white solid.
$^1$H NMR (DMSO-$d_6$): δ 1.93 (s, 3H), 4.61–4.79 (m, 1H), 4.87–4.92 (m, 2H), 5.13 (dd, 1H, J=1.22 and 10.23 Hz), 5.90–5.98 (m, 1H), 6.75 (dd, 1H, J=2.44 and 8.24 Hz), 6.81 (s, 1H), 6.96–6.99 (m, H) 7.12 (d, H), 7.24 (d, H), 7.36 (d, H), 9.78 (broad s, H).
MS (ESI) m/z 299 [M+H]+.

EXAMPLE 79

4-(7-chloro-2-propyl-2H-indazol-3-yl)-3-methylphenol

Step 1: 7-chloro-3-(4-methoxy-2-methylphenyl)-2-propyl-2H-indazole

Prepared according to Method D step B from 7-chloro-3-(4-methoxy-2-methylphenyl)-1H-indazole (0.150 g, 0.52 mmol), sodium hydride (60% in oil, 0.025 g, 1.04 mmol) and 1-propyl iodide (0.07 mL, 0.7 mmol) to give the title compound (0.056 g) as a white solid.
$^1$H NMR (DMSO-$d_6$): δ 0.71 (t, 3H), 1.79 (m, 2H), 2.00 (s, 3H), 3.83 (s, 3H), 4.04–4.09 (m, 1H), 4.20–4.25 (m, 1H), 6.94–6.98 (m, 2H), 7.00 (s, 1H), 7.22 (d, 1H), 7.27 (d, 1H), 7.35 (d, 1H).
MS (ESI) m/z 315 [M+H]+.

Step 2: 4-(7-chloro-2-propyl-2H-indazol-3-yl)-3-methylphenol 7-chloro-3-(4-methoxy-2-methylphenyl)-2-propyl-1H-indazole Prepared according to Method D step C from 7-chloro-3-(4-methoxy-2-methylphenyl)-2-propyl-2H-indazole (0.04 g, 0.13 mmol), boron tribromide (0.20 mL, 2.10 mmol) and 1.0 mL of cyclohexene to give the product (0.023 g) as a white solid.

¹H NMR (DMSO-d₆): δ 0.71 (t, 3H), 1.76–1.81 (m, 2H), 1.93 (s, 3H), 4.03–4.08 (m, 1H), 4.19–4.24 (m, 1H), 6.77 (dd, 1H, J=2.29 and 8.24 Hz), 6.82 (s, 1H), 6.96 (t, 1H), 7.12 (d, 1H), 7.22 (d, 1H), 7.34 (d, 1H), 9.78 (broad s, 1H).
MS (ESI) m/z 301 [M+H]+.

EXAMPLE 80

4-(7-chloro-1-isopropyl-1H-indazol-3-yl)benzene-1,3-diol

Step 1: 7-chloro-3-(2,4-dimethoxyphenyl)-1-isopropyl-1H-indazole

Prepared according to Method D step B from 7-chloro-3-(4-methoxy-2-methylphenyl)-1H-indazole (0.150 g, 0.46 mmol), sodium hydride (60% in oil, 0.025 g, 1.04 mmol) and 2-iodopropane (0.07 mL, 0.7 mmol) to give the title compound (0.132 g) as a white solid.
¹H NMR (DMSO-d₆): δ 1.53 (d, 6H), 3.76 (s, 3H), 3.83 (s, 3H), 5.62–5.68 (m, 1H), 6.65 (dd, 1H, J=2.44 and 8.39 Hz), 6.72 (s, 1H), 7.07 (t, 1H), 7.36 (d, 1H), 7.43 (d, 1H), 7.52 (d, 1H).
MS (ESI) m/z 331 [M+H]+.

Step 2: 4-(7-chloro-1-isopropyl-1H-indazol-3-yl)benzene-1,3-diol

Prepared according to Method D step C from 7-chloro-3-(2,4-dimethoxyphenyl)-1-isopropyl-1H-indazole (0.132 g, 0.4 mmol), boron tribromide (0.377 mL, 4.0 mmol) and 1.0 mL of cyclohexene to give the product (0.090 g) as a white solid.
¹H NMR (DMSO-d₆): δ 1.53 (d, 6H), 5.64–5.69 (m, 1H), 6.39 (dd, 1H, J=2.44 and 8.39 Hz), 6.43 (s, 1H), 7.13 (t, 1H), 7.47–7.50 (m, 2H), 7.89 (d, 1H), 9.58 (broad s, 1H), 10.06 (broad s, 1H).
MS (ESI) m/z 303 [M+H]+.

EXAMPLE 81

4-(7-chloro-2-isopropyl-2H-indazol-3-yl)-3-methylphenol

Step 1: 7-chloro-2-isopropyl-3-(4-methoxy-2-methylphenyl)-2H-indazole

Prepared according to Method D step B from 7-chloro-3-(4-methoxy-2-methylphenyl)-1H-indazole (0.150 g, 0.52 mmol), sodium hydride (60% in oil, 0.025 g, 1.04 mmol) and 2-iodopropane (0.07 mL, 0.7 mmol) to give the title compound (0.059 g) as a white solid.
¹H NMR (DMSO-d₆): δ 1.46 (s, 6H), 1.99 (s, 3H), 3.83 (s, 3H), 4.42–4.47 (m, 1H), 6.94–6.98 (m, 2H), 7.04 (s, 1H), 7.20 (dd, 1H, J=0.61 and 8.25 Hz), 7.26 (d, 1H), 7.35 (dd, 1H, J=0.76 and 7.17 Hz).
MS (ESI) m/z 315 [M+H]+.

Step 2: 4-(7-chloro-2-isopropyl-2H-indazol-3-yl)-3-methylphenol

Prepared according to Method D step C from 7-chloro-2-isopropyl-3-(4-methoxy-2-methylphenyl)-2H-indazole (0.05 g, 0.16 mmol), boron tribromide (0.19 mL, 2.0 mmol) and 1.0 mL of cyclohexene to give the product (0.016 g) as a white solid.

¹H NMR (DMSO-d₆): δ 1.45 (d, 6H), 1.93 (s, 3H), 4.43–4.48 (m, 1H), 6.77 (dd, 1H, J=2.29 and 8.24 Hz), 6.83 (s, 1H), 6.96 (t, 1H), 7.12 (d, 1H), 7.20 (d, 1H), 7.34 (d, 1H), 9.78 (broad s, 1H).
MS (ESI) m/z 301 [M+H]+.

EXAMPLE 82

4-(1-allyl-7-chloro-1H-indazol-3-yl)-3-methylphenol

Step 1: 1-allyl-7-chloro-3-(4-methoxy-2-methylphenyl)-1H-indazole

Prepared according to Method D step B from 7-chloro-3-(4-methoxy-2-methylphenyl)-1H-indazole (0.150 g, 0.52 mmol), sodium hydride (60% in oil, 0.025 g, 1.04 mmol) and allyl bromide (0.07 mL, 0.7 mmol) to give the title compound (0.102 g) as a white solid.
¹H NMR (DMSO-d₆): δ 2.27 (s, 3H), 3.80 (s, 3H), 4.80 (dd, 1H, J=1.37 and 17.10 Hz), 5.13 (dd, 1H, J=1.37 and 10.38 Hz), 5.36 (dd, 1H, J=3.36 and 1.67 Hz), 6.07–6.13 (m, 1H), 6.90 (dd, 1H, J=2.59 and 8.39 Hz), 6.96 (s, 1H), 7.14 (t, 1H), 7.36 (d, 1H), 7.48 (d, 1H), 7.53 (d, 1H);
MS (ESI) m/z 313 [M+H]+.

Step 2: 4-(1-allyl-7-chloro-1H-indazole-3-yl)-3-methylphenol

Prepared according to Method D step C from 7-chloro-1-cyclopentyl-3-(4-methoxy-2-methylphenyl)-1H-indazole (0.102 g, 0.33 mmol), boron tribromide (0.19 mL, 2.0 mmol) and 1.0 mL of cyclohexene to give the product (0.099 g) as a white solid.
¹H NMR (DMSO-d₆): δ 2.21 (s, 1H), 4.82 (dd, 1H, J=1.37 and 17.10 Hz), 5.12 (d, 1H), 5.36 (s, 2H), 6.06–6.13 (m, 1H), 6.72 (dd, 1H, J=2.44 and 8.24 Hz), 6.76 (s, 1H), 7.13 (t, 1H), 7.24 (d, 1H), 7.47 (d, 1H), 7.52 (d, 1H), 9.56 ( broad s, 1H)
MS (ESI) m/z 299 [M+H]+.

EXAMPLE 83

4-[1-isopropyl-7-(trifluoromethyl)-1H-indazole-3-yl]-3-methylphenol

Step 1: 1-isopropyl-3-(4-methoxy-2-methylphenyl)-7-(trifluoromethyl)-1H-indazole Prepared according to Method D step B from 3-(4-methoxy-2-methylphenyl)-7-(trifluoro-methyl)-1H-indazole (0.150 g, 0.52 mmol), sodium hydride (60% in oil, 0.025 g, 1.04 mmol) and allyl bromide (0.07 mL, 0.7 mmol) to give the title compound (0.072 g) as a white solid.
¹H NMR (DMSO-d₆): δ 1.52 (d, 6H), 2.30 (s, 3H), 3.81 (s, 3H), 4.99–5.02 (m, 1H), 6.91 (dd, 1H, J=2.60 and 8.40 Hz), 6.98 (d, 1H), 7.32 (t, 1H), 7.41 (d, 1H), 7.86–7.91 (m, 2H)
MS (ESI) m/z 349 [M+H]+.

Step 2: 4-[1-isopropyl-7-(trifluoromethyl)-1H-indazole-3-yl]-3-methylphenol

Prepared according to Method D step C from 1-isopropyl-3-(4-methoxy-2-methylphenyl)-7-(trifluoromethyl)-1H-indazole (0.062 g, 0.2 mmol), boron tribromide (0.067 mL, 0.7 mmol) and 1.0 mL of cyclohexene to give the product (0.093 g) as a white solid.

¹H NMR (DMSO-d₆): δ 1.51 (d, 6H), 2.24 (d, 3H), 4.97–5.02 (m, H), 6.73 (dd, 1H, J=2.44 and 8.24 Hz), 6.79 (s, 1H), 7.27–7.30 (m, 2H), 7.85 (d, 1H), 7.89 (d, 1H), 9.59 (broad s, 1H)
MS (ESI) m/z 335 [M+H]+.
MS (ESI) m/z 333 [M−H]−.

EXAMPLE 84

4-(7-chloro-1-cyclopentyl-1H-indazole-3-yl)-3-methylphenol

Step 1: 7-chloro-1-cyclopentyl-3-(4-methoxy-2-methylphenyl)-1H-indazole

Prepared according to Method D step B from 7-chloro-3-(4-methoxy-2-methylphenyl)-1H-indazole (0.150 g, 0.52 mmol), sodium hydride (60% in oil, 0.025 g, 1.04 mmol) and cyclopentyl bromide (0.075 mL, 0.7 mmol) to give the title compound (0.090 g) as a white solid.
¹H NMR (DMSO-d₆): δ 1.67–1.73 (m, 2H), 1.82–1.87 (m, 2H), 2.09–2.15 (m, 4H), 3.80 (s, 3H), 5.81–5.84 (m, 1H), 6.90 (dd, 1H, J=2.59 and 8.39 Hz), 6.96 (s, 1H), 7.10–7.14 (t, 1H), 7.39 (d, 1H), 7.47 (d, 1H), 7.55 (d, 1H)
MS (ESI) m/z 341 [M+H]+.

Step 2: 4-(7-chloro-1-cyclopentyl-1H-indazole-3-yl)-3-methylphenol

Prepared according to Method D step C from 7-chloro-1-cyclopentyl-3-(4-methoxy-2-methylphenyl)-1H-indazole (0.090 g, 0.26 mmol), boron tribromide (0.100 mL, 1.0 mmol) and 1.0 mL of cyclohexene to give the product (0.035 g) as a white solid.
¹H NMR (DMSO-d₆): δ 1.67–1.72 (m, 1H), 1.82–1.88 (m, 2H), 2.07–2.16 (m, 4H), 2.24 (s, 3H), 5.79–5.85 (m, 1H), 6.72 (dd, 1H, J=2.44 and 8.24 Hz), 6.76 (s, 1H), 7.11 (t, 1H), 7.26 (d, 1H), 7.45 (d, 1H), 7.54 (d, 1H), 9.54 (broad s, 1H)
MS (ESI) m/z 327 [M+H]+.

EXAMPLE 85

4-(1-allyl-7-chloro-1H-indazole-3-yl)benzene-1,3-diol

Step 1: 1-allyl-7-chloro-3-(2,4-dimethoxyphenyl)-1H-indazole

Prepared according to Method D step B from 3-(2,4-dimethoxyphenyl)-7-(trifluoromethyl)-1H-indazole (0.150 g, 0.46 mmol), sodium hydride (60% in oil, 0.025 g, 1.04 mmol) and allyl bromide (0.07 mL, 0.7 mmol) to give the title compound (0.101 g) as a white solid.
¹H NMR (DMSO-d₆): δ 3.76 (s, 3H), 3.83 (s, 3H), 4.88 (dd, 1H, J=1.52 and 17.10 Hz), 5.13 (dd, 1H, J=1.52 and 10.38 Hz), 5.35 (d, 2H), 6.07–6.11 (m, 1H), 6.64 (dd, 1H, J=2.44 and 8.39 Hz), 6.73 (s, 1H), 7.09 (t, 1H), 7.37 (d, 1H), 7.44 (d, 1H), 7.54 (d, 1H)
MS (ESI) m/z 329 [M+H]+.

Step 2: 4-(1-allyl-7-chloro-1H-indazole-3-yl)benzene-1,3-diol

Prepared according to Method D step C from 1-allyl-7-chloro-3-(2,4-dimethoxyphenyl)-1H-indazole (0.101 g, 0.30 mmol), boron tribromide (0.226 mL, 2.4 mmol) and 1.0 mL of cyclohexene to give the product (0.048 g) as a white solid.
¹H NMR (DMSO-d₆): δ 4.80 (dd, 1H, J=1.37 and 17.10 Hz), 5.11 (d, 1H), 5.35 (s, 1H), 6.06–6.13 (m, 1H), 6.40 (dd, 1H, J=2.44 and 8.39 Hz), 6.43 (s, 1H), 7.13 (t, 1H), 7.47–7.50 (m, 1H), 7.89 (d, 1H), 9.58 (broad s, 1H), 9.90 (broad s, 1H)
MS (ESI) m/z 301 [M+H]+.

EXAMPLE 86

4-(7-chloro-1-propyl-1H-indazole-3-yl)-3-methylphenol

Step 1: 7-chloro-3-(4-methoxy-2-methylphenyl)-1-propyl-1H-indazole

Prepared according to Method D step B from 7-chloro-3-(4-methoxy-2-methylphenyl)-1H-indazole (0.150 g, 0.52 mmol), sodium hydride (60% in oil, 0.025 g, 1.04 mmol) and 2-iodopropane (0.07 mL, 0.7 mmol) to give the title compound (0.100 g) as a white solid.
¹H NMR (DMSO-d₆): δ 0.87 (t, 3H), 1.84–1.91 (m, 2H), 2.28 (s, 3H), 3.80 (s, 3H), 4.70 (t, 2H), 6.89 (dd, 1H, J=2.59 and 8.39 Hz), 6.95 (s, 1H), 7.12 (t, 1H), 7.35 (d, 1H), 7.48 (d, 1H), 7.52 (d, 1H)
MS (ESI) m/z 315 [M+H]+.

Step 2: 4-(7-chloro-1-propyl-1H-indazole-3-yl)-3-methylphenol

Prepared according to Method D step C from 7-chloro-3-(4-methoxy-2-methylphenyl)-1-propyl-1H-indazole (0.90 g, 0.3 mmol), boron tribromide (0.113 mL, 1.20 mmol) and 1.0 mL of cyclohexene to give the product (0.073 g) as a white solid.
¹H NMR (DMSO-d₆): δ 0.86 (t, 3H), 1.87 (m, 2H), 2.21 (s, 3H), 4.67–4.70 (m, 2H), 6.71 (dd, 1H, J=2.44 and 8.24 Hz), 6.76 (s, 1H), 7.11 (t, 1H), 7.20 (s, 1H), 7.46 (d, 1H), 7.51 (d, 1H), 9.55 (broad s, 1H)
MS (ESI) m/z 301 [M+H]+.

EXAMPLE 87

4-(7-fluoro-1-isopropyl-1H-indazole-3-yl)benzene-1,3-diol

Step 1: 3-(2,4-dimethoxyphenyl)-7-fluoro-1-isopropyl-1H-indazole

Prepared according to Method D step B from 7-fluoro-3-(4-methoxy-2-methylphenyl)-1H-indazole (0.300 g, 1.1 mmol), sodium hydride (60% in oil, 0.058 g, 1.44 mmol) and 2-iodopropane (0.20 mL, 2.0 mmol) to give the title compound (0.232 g) as a white solid.
¹H NMR (DMSO-d₆): δ 1.53 (d, 6H), 3.77 (s, 3H), 3.82 (s, 3H), 5.03–5.08 (m, 1H), 6.63 (dd, 1H, J=2.29 and 8.39 Hz), 6.72 (s, 1H), 7.02–7.05 (m, 1H), 7.15–7.20 (m, 1H), 7.37–7.39 (m, 2H)
MS (ESI) m/z 315 [M+H]+.

Step 2: 4-(7-fluoro-1-isopropyl-1H-indazole-3-yl)benzene-1,3-diol

Prepared according to Method D step C from 3-(2,4-dimethoxyphenyl)-7-fluoro-1-isopropyl-1H-indazole (0.213 g, 0.68 mmol), boron tribromide (0.513 mL, 5.0 mmol) and 1.0 mL of cyclohexene to give the product (0.160 g) as a white solid.
$^1$H NMR (DMSO-d$_6$): δ 1.53 (s, 6H), 5.05–5.11 (m, 1H), 6.40 (dd, 1H, J=2.44 and 8.39 Hz), 6.42 (s, 1H), 7.09–7.14 (m, 1H), 7.23–7.27 (m, 1H), 7.55 (d, 1H), 7.77 (d, 1H), 9.58 (s, 1H), 10.16 (s, 1H)
MS (ESI) m/z 287 [M+H]+.

EXAMPLE 88

4-(1-cyclopentyl-7-fluoro-1H-indazole-3-yl)benzene-1,3-diol

Step 1: 1-cyclopentyl-3-(2,4-dimethoxyphenyl)-7-fluoro-1H-indazole

Prepared according to Method D step B from 3-(2,4-dimethoxyphenyl)-7-fluoro-1H-indazole (0.150 g, 0.55 mmol), sodium hydride (60% in oil, 0.058 g, 0.66 mmol) and cyclopentyl bromide (0.214 mL, 2.0 mmol) to give the title compound (0.234 g) as a white solid.
$^1$H NMR (DMSO-d$_6$): δ 1.67–1.70 (m, 2H), 1.84–1.87 (m, 2H), 2.08–2.16 (m, 4H), 3.76 (s, 3H), 3.82 (s, 3H), 5.23–5.26 (m, 1H), 6.64 (dd, 1H, J=2.29 and 8.39 Hz), 6.71 (s, 1H), 7.01–7.05 (m, 1H), 7.15–7.19 (m, 1H), 7.37 (d, 2H)
MS (ESI) m/z 341 [M+H]+.

Step 2: 4-(1-cyclopentyl-7-fluoro-1H-indazole-3-yl)benzene-1,3-diol

Prepared according to Method D step C from 1-cyclopentyl-3-(2,4-dimethoxyphenyl)-7-fluoro-1H-indazole (0.225 g, 0.6 mmol), boron tribromide (0.5 mL, 5 mmol) and 1.0 mL of cyclohexene to give the product (0.147 g) as a white solid.
$^1$H NMR (DMSO-d$_6$): δ 1.68–1.75 (m, 2H), 1.81–1.98 (m, 2H), 1.99–2.10 (m, 2H), 2.13–2.19 (m, 2H), 5.25–5.31 (m, H), 6.40 (dd, 1H, J=2.44 and 8.39 Hz), 6.42 (s, 1H), 7.09–7.13 (m, 1H), 7.23–7.27 (m, 1H), 7.55 (d, 1H), 7.77 (d, 1H), 9.59 (broad s, 1H), 10.16 (broad s, 1H)
MS (ESI) m/z 313 [M+H]+.

EXAMPLE 89

4-(7-fluoro-2-isopropyl-2H-indazole-3-yl)benzene-1,3-diol

Step 1: 3-(2,4-dimethoxyphenyl)-7-fluoro-2-isopropyl-2H-indazole

Prepared according to Method D step B from 3-(2,4-dimethoxyphenyl)-7-fluoro-1H-indazole (0.300 g, 1.10 mmol), sodium hydride (60% in oil, 0.058 g, 1.50 mmol) and 2-iodopropane (0.20 mL, 2.00 mmol) to give the title compound (0.080 g) as a white solid.
$^1$H NMR (DMSO-d$_6$): δ 1.36 (d, 3H), 1.53 (d, 3H), 3.75 (s, 3H), 3.86 (s, 3H), 4.46–4.51 (m, H), 6.73 (dd, 1H, J=2.29 and 8.24 Hz), 6.78 (s, 1H), 6.89–6.93 (m, 1H), 6.98–7.01 (m, 1H), 7.10 (d, 1H), 7.28 (d, 1H)
MS (ESI) m/z 315 [M+H]+.

Step 2: 4-(7-fluoro-2-isopropyl-2H-indazole-3-yl)benzene-1,3-diol

Prepared according to Method D step C from 3-(2,4-dimethoxyphenyl)-7-fluoro-2-isopropyl-2H-indazole (0.07 g, 0.22 mmol), boron tribromide (0.12 mL, 1.2 mmol) and 1.0 mL of cyclohexene to give the product (0.023 g) as a white solid.
mp>160° C.;
$^1$H NMR (DMSO-d$_6$): δ 0.64 (d, 3H), 0.76 (d, 3H), 2.19–2.23 (m, 1H), 3.89–3.93 (m, 1H), 4.06–4.12 (m, 1H), 6.53 (dd, 1H, J=2.29–8.24 Hz), 6.60 (s, 1H), 6.88–6.92 (m, 1H), 6.97–7.01 (m, 1H), 7.10–7.13 (m, 2H), 9.95 (broad s, 1H)
MS (ESI) m/z 285 [M−H]−.

EXAMPLE 90

4-(2-cyclopentyl-7-fluoro-2H-indazole-3-yl)benzene-1,3-di I

Step 1: 2-cyclopentyl-3-(2,4-dimethoxyphenyl)-7-fluoro-2H-indazole

Prepared according to Method D step B from 3-(2,4-dimethoxyphenyl)-7-fluoro-1H-indazole (0.300 g, 1.10 mmol), sodium hydride (60% in oil, 0.058 g, 1.50 mmol) and 2-iodopropane (0.20 mL, 2.00 mmol) to give the title compound (0.073 g) as a white solid.
$^1$H NMR (DMSO-d$_6$): δ1.55–1.65 (m, 2H), 1.88–1.98 (m, 4H), 2.09–2.19 (m, 2H), 3.74 (s, 3H), 3.86 (s, 3H), 4.65–4.68 (m, 1H), 6.72 (dd, 1H, J=2.44 and 8.39 Hz), 6.78 s, 1H), 6.88–6.92 (m, 1H), 6.97–7.01 (m, 1H), 7.09 (d, 1H), 7.28 (d, 1H)
MS (ESI) m/z 341 [M+H]+.

Step 2: 4-(2-cyclopentyl-7-fluoro-2H-indazole-3-yl)benzene-1,3-diol

Prepared according to Method D step C from 2-cyclopentyl-3-(2,4-dimethoxyphenyl)-7-fluoro-2H-indazole (0.062 g, 0.18 mmol), boron tribromide (0.12 mL, 1.2 mmol) and 1.0 mL of cyclohexene to give the product (0.025 g) as a white solid.
$^1$H NMR (DMSO-d$_6$): δ 1.55–1.66 (m, 2H), 1.86–1.98 (m, 4H), 2.11–2.24 (m, 2H), 4.70–4.81 (m, 1H), 6.40 (dd, 1H, J=2.29 and 8.24 Hz), 6.50 (s, 1H), 6.86–6.91 (m, 1H), 6.95–7.00 (m, 1H), 7.05 (s, 1H), 7.09–7.14 (m, 1H), 6.70 (s, 1H), 9.97 (s, 1H)
MS (ESI) m/z 311 [M−H]−.

EXAMPLE 91

4-(7-fluoro-1-isopropyl-1H-indazole-3-yl)-3-methylphenol

Step 1: 7-fluoro-1-isopropyl-3-(4-methoxy-2-methylphenyl)-1H-indazole

Prepared according to Method D step B from 7-fluoro-3-(4-methoxy-2-methylphenyl)-1H-indazole (0.150 g, 0.52 mmol), sodium hydride (60% in oil, 0.025 g, 1.04 mmol) and 2-iodopropane (0.075 mL, 0.7 mmol) to give the title compound (0.161) as a white solid.
$^1$H NMR (DMSO-d$_6$): δ 1.53 (d, 6H), 2.31 (s, 3H), 3.80 (s, 3H), 5.05–5.11 (m, 1H), 6.89 (dd, 1H, J=2.75 and 8.39 Hz), 6.95 (s, 1H), 7.07–7.11 (m, 1H), 7.21–7.25 (m, 1H), 7.40 (dd, 1H, J=2.29 and 8.09 Hz)
MS (ESI) m/z 297 [M+H]+.

Step 2: 4-(7-fluoro-1-isopropyl-1H-indazole-3-yl)-3-methylphenol

Prepared according to Method D step C from 7-fluoro-1-isopropyl-3-(4-methoxy-2-methylphenyl)-1H-indazole (0.151 g, 0.500 mmol), boron tribromide (0.118 mL, 1.25 mmol) and 1.0 mL of cyclohexene to give the product (0.144 g) as a white solid.
$^1$H NMR (DMSO-$d_6$): δ 1.52 (d, 6H), 2.25 (s, 3H), 5.04–5.09 (m, 1H), 6.72 (dd, 1H, J=2.59 and 8.24 Hz), 6.76 (s, 1H), 7.06–7.10 (m, 1H), 7.19–7.23 (m, 1H), 7.27 (d, 1H), 7.39 (d, 1H).

EXAMPLE 92

4-(7-fluoro-2-propyl-2H-indazole-3-yl)-3-methylphenol

Step 1: 7-fluoro-3-(4-methoxy-2-methylphenyl)-2-propyl-2H-indazole

Prepared according to Method D step B from 7-fluoro-3-(4-methoxy-2-methylphenyl)-1H-indazole (0.150 g, 0.52 mmol), sodium hydride (60% in oil, 0.025 g, 1.04 mmol) and 1-iodopropane (0.075 mL, 0.7 mmol) to give the title compound (0.071 g) as a white solid.
$^1$H NMR (DMSO-$d_6$): δ 0.70 (t, 3H), 1.75–1.97 (m, 2H), 1.99 (s, 3H), 3.83 (s, 3H), 4.02–4.08 (m, 1H), 4.18–4.24 (m, 1H), 6.92–6.96 (m, 2H), 7.00–7.07 (m, 3H), 7.27 (d, 1H)
MS (ESI) m/z 299 [M+H]+.

Step 2: 4-(7-fluoro-2-propyl-2H-indazole-3-yl)-3-methylphenol

Prepared according to Method D step C from 7-fluoro-3-(4-methoxy-2-methylphenyl)-2-propyl-2H-indazole (0.059 g, 0.20 mmol), boron tribromide (0.05 mL, 0.5 mmol) and 1.0 mL of cyclohexene to give the product (0.052 g) as a white solid.
$^1$H NMR (DMSO-$d_6$): δ 0.71 (t, 3H), 1.77–1.81 (m, 2H), 1.93 (s, 3H), 4.03–4.07 (m, 1H), 4.17–4.23 (m, 1H), 6.76 (dd, 1H, J=2.44 and 8.24 Hz), 6.82 (s, 1H), 6.91–6.95 (m, 1H), 6.99–7.03 (m, 1H), 7.06 (d, 1H), 7.12 (d, 1H)

EXAMPLE 93

4-(7-fluoro-1-propyl-1H-indazole-3-yl)-3-methylphenol

Step 1: 7-fluoro-3-(4-methoxy-2-methylphenyl)-1-propyl-1H-indazole

Prepared according to Method D step B from 7-fluoro-3-(4-methoxy-2-methylphenyl)-1H-indazole (0.300 g, 1.10 mmol), sodium hydride (60% in oil, 0.058 g, 1.50 mmol) and 2-iodopropane (0.20 mL, 2.00 mmol) to give the title compound (0.279 g) as a white solid.
$^1$H NMR (DMSO-$d_6$): δ 0.84 (t, 3H), 1.85–1.90 (m, 2H), 2.30 (s, 3H), 3.80 (s, 3H), 6.89 (dd, 1H, J=2.59 and 8.39 Hz), 6.95 (s, 1H), 7.0–7.11 (m, 1H), 7.21–7.25 (m, 1H), 7.38 (d, 2H)
MS (ESI) m/z 297 [M–H]–. MS (ESI) m/z 299 [M+H]+.

Step 2: 4-(7-fluoro-1-propyl-$^1$H-indazole-3-yl)-3-methylphenol

Prepared according to Method D step C from 7-fluoro-3-(4-methoxy-2-methylphenyl)-1-propyl-1H-indazole (0.268 g, 0.90 mmol), boron tribromide (0.275 mL, 2.90 mmol) and 1.0 mL of cyclohexene to give the product (0.252 g) as a white solid.
$^1$H NMR (DMSO-$d_6$): δ 0.84 (t, 3H), 1.85–1.89 (m, 2H), 2.23 (s, 3H), 4.46 (t, 2H), 6.70–6.72 (m, 1H), 6.76 (s, 1H), 7.07–7.09 (m, 1H), 7.20–7.24 (m, 1H), 7.25 (d, 1H), 7.37 (d, 1H), 9.53 (broad s, 1H).

EXAMPLE 94

4-(7-fluoro-1-isobutyl-1H-indazole-3-yl)benzene-1,3-diol

Step 1: 3-(2,4-dimethoxyphenyl)-7-fluoro-1-isobutyl-1H-indazole

Prepared according to Method D step B from 3-(2,4-dimethoxyphenyl)-7-fluoro-1H-indazole (0.300 g, 1.10 mmol), sodium hydride (60% in oil, 0.058 g, 1.50 mmol) and 1-iodo-2-methylpropane (0.23 mL, 2.00 mmol) to give the title compound (0.187 g) as a white solid.
mp 92–93° C.;
$^1$H NMR (DMSO-$d_6$): δ 0.88 (d, 6H), 2.17–2.22 (m, 1H), 3.77 (s, 3H), 3.82 (s, 3H), 4.29 (d, 2H), 6.63 (dd, 1H, J=2.44 and 8.39 Hz) 6.72 (s, 1H), 7.02–7.06 (m, 1H), 7.16–7.20 (m, 1H), 7.37–7.39 (m, 2H)
MS (ESI) m/z 329 [M+H]+.

Step 2: 4-(7-fluoro-1-isobutyl-1H-indazole-3-yl)benzene-1,3-diol

Prepared according to Method D step C from 3-(2,4-dimethoxyphenyl)-7-fluoro-1-isobutyl-1H-indazole (0.177 g, 0.5 mmol), boron tribromide (0.275 mL, 2.90 mmol) and 1.0 mL of cyclohexene to give the product (0.085 g) as a white solid.
$^1$H NMR (DMSO-$d_6$): δ 0.87 (s, 6H), 2.19–2.21 (m, 1H), 4.31 (d, 2H), 6.39 (dd, 1H, J=2.44 and 8.39 Hz), 6.43 (s, 1H), 7.08–7.12 (m, 1H), 7.22–7.26 (m, 1H), 7.52 (d, 1H), 7.75 (d, 1H), 9.58 (s, 1H), 10.08 (s, 1H)
MS (ESI) m/z 301 [M+H]+.

EXAMPLE 95

4-(7-fluoro-2-isobutyl-2H-indazole-3-yl)benzene-1,3-diol

Step 1: 3-(2,4-dimethoxyphenyl)-7-fluoro-2-isobutyl-2H-indazole

Prepared according to Method D step B from 3-(2,4-dimethoxyphenyl)-7-fluoro-1H-indazole (0.300 g, 1.10 mmol), sodium hydride (60% in oil, 0.058 g, 1.50 mmol) and 1-iodo-2-methylpropane (0.23 mL, 2.00 mmol) to give the title compound (0.046 g) as a white solid.
$^1$H NMR (DMSO-$d_6$): δ 0.65 (d, 3H), 0.76 (d, 3H), 2.18–2.23 (m, 1H), 3.74 (s, 3H), 3.86 (s, 3H), 3.88–3.94 (m, 1H), 4.09–4.13 (m, 1H), 6.72 (dd, 1H, J=2.44 and 8.39 Hz), 6.78 (s, 1H), 6.90–6.94 (m, 1H), 6.98–7.02 (m, 1H), 7.11 (d, 1H), 7.28 (d, 1H)
MS (ESI) m/z 329 [M+H]+.

Step 2: 4-(7-fluoro-2-isobutyl-2H-indazole-3-yl)benzene-1,3-diol

Prepared according to Method D step C from 3-(2,4-dimethoxyphenyl)-7-fluoro-2-isobutyl-2H-indazole (0.036 g, 0.1 mmol), boron tribromide (0.083 mL, 0.9 mmol) and 1.0 mL of cyclohexene to give the product (0.024 g) as a white solid.
¹H NMR (DMSO-d₆): δ 0.64–0.65 (m, 3H), 0.75–0.77 (m, 3H), 2.16–2.35 (m, H), 4.07–4.08 (m, 2H), 4.40 (dd, 1H, J=2.29 and 8.39 Hz), 6.49 (s, 1H), 6.88–6.92 (m, 1H), 6.96–7.01 (m, 1H), 7.04 (d, 1H), 7.10–7.15 (m, 1H), 6.96 (s, 1H), 9.80 (s, 1H)
MS (ESI) m/z 301 [M+H]+.

EXAMPLE 96

4-(7-fluoro-1-isobutyl-1H-indazole-3-yl)-3-methylphenol

Step 1: 7-fluoro-1-isobutyl-3-(4-methoxy-2-methylphenyl)-1H-indazole

Prepared according to Method D step B from 7-fluoro-3-(4-methoxy-2-methylphenyl)-1H-indazole (0.300 g, 1.20 mmol), sodium hydride (60% in oil, 0.058 g, 1.50 mmol) and 1-iodo-2-methylpropane (0.23 mL, 2.00 mmol) to give the title compound (0.374 g) as a white solid.
¹H NMR (DMSO-d₆): δ 0.88 (d, 6H), 2.19–2.24 (m, H), 2.30 (s, 3H), 3.80 (s, 3H), 4.32 (d, 2H), 6.89 (dd, 1H, J=2.59 and 8.39 Hz), 6.95 (s, 1H), 7.07–7.11 (m, 1), 7.21–7.25)m, 1H), 7.38 (d, 2H)
MS (ESI) m/z 313 [M+H]+.

Step 2: 4-(7-fluoro-1-isobutyl-1H-indazole-3-yl)-3-methylphenol

Prepared according to Method D step C from 7-fluoro-1-isobutyl-3-(4-methoxy-2-methyl-phenyl)-1H-indazole (0.364 g, 1.2 mmol), boron tribromide (0.450 mL, 4.6 mmol) and 1.0 mL of cyclohexene to give the product (0.344 g) as a white solid.
mp 126–128° C.;
¹H NMR (DMSO-d₆): δ 0.87 (d, 6H), 1.98–2.07(m, 1H), 2.23 (s, 1H), 4.30 (d, 2H), 6.71 (dd, 1H, J=2.59 and 8.24 Hz), 6.76 (s, 1H), 7.06–7.10 (m, 1H), 7.20–7.24 (m, 1H), 7.25 (d, 1H), 7.37 (d, 1H), 9.54 (s, 1H)
MS (ESI) m/z 299 [M+H]+.

EXAMPLE 97

4-(2-allyl-7-fluoro-2H-indazole-3-yl)benzene-1,3-diol

Step 1: 2-allyl-3-(2,4-dimethoxyphenyl)-7-fluoro-2H-indazole

Prepared according to Method D step B from 3-(2,4-dimethoxyphenyl)-7-fluoro-1H-indazole (0.300 g, 1.10 mmol), sodium hydride (60% in oil, 0.058 g, 1.50 mmol) and allyl bromide (0.173 mL, 2.00 mmol) to give the title compound (0.067 g) as a white solid.
¹H NMR (DMSO-d₆): δ 3.75 (s, 3H), 3.85 (s, 3H), 4.82–4.87 (m, 2H), 4.98 (d, 1H), 5.12 (dd, 1H, J=1.37 and 10.23 Hz), 5.92–6.00 (m, 1H), 6.72 (dd, 1H, J=2.44 and 8.39 Hz) 6.78 (s, 1H), 6.91–6.95 (m, 1H), 7.00–7.04 (m, 1H), 7.14 (d, 1H), 7.27 (d, 1H)
MS (ESI) m/z 313 [M+H]+.

Step 2: 4-(2-allyl-7-fluoro-2H-indazole-3-yl)benzene-1,3-diol

Prepared according to Method D step C from 2-allyl-3-(2,4-dimethoxyphenyl)-7-fluoro-2H-indazole (0.057 g, 0.2 mmol), boron tribromide (0.150 mL, 1.6 mmol) and 1.0 mL of cyclohexene to give the product (0.023 g) as a white solid.
mp 69–70° C.;
¹H NMR (DMSO-d₆): δ 4.81 (dd, 1H, J=1.68 and 6.87 Hz), 4.90–5.01 (m, 2H), 5.03–5.14 (m, 1H), 5.93–6.02 (m, 1H), 6.38–6.45 (m, 2H), 6.91–7.07 (m, 3H), 7.17 (d, 1H), 9.71 (s, 1H), 9.88 (s, 1H)
MS (ESI) m/z 285 [M+H]+.

EXAMPLE 98

4-(1-allyl-7-fluoro-1H-indazole-3-yl)benzene-1,3-diol

Step 1: 1-allyl-3-(2,4-dimethoxyphenyl)-7-fluoro-1H-indazole

Prepared according to Method D step B from 3-(2,4-dimethoxyphenyl)-7-fluoro-1H-indazole (0.300 g, 1.10 mmol), sodium hydride (60% in oil, 0.058 g, 1.50 mmol) and allyl bromide(0.173 mL, 2.00 mmol) to give the title compound (0.198 g) as a white solid.
¹H NMR (DMSO-d₆): δ 3.77 (s, 3H), 3.83 (s, 3H), 5.00 (dd, 1H, J=1.22 and 17.10 Hz), 5.12 (s, 2H), 5.15 (dd, 1H, J=1.37 and 10.23 Hz), 6.04–6.10 (m, 1H), 6.64 (dd, 1H, J=2.44 and 8.55 Hz), 6.72 (s, 1H), 7.04–7.08 (m, 1H), 7.17–7.21 (m, 1H), 7.39 (d, 2H).
MS (ESI) m/z 313 [M+H]+.

Step 2: 4-(1-allyl-7-fluoro-1H-indazole-3-yl)benzene-1,3-diol

Prepared according to Method D step C from 1-allyl-3-(2,4-dimethoxyphenyl)-7-fluoro-1H-indazole (0.187 g, 0.6 mmol), boron tribromide (0.362 mL, 3.80 mmol) and 1.0 mL of cyclohexene to give the product (0.157 g) as a white solid.
¹H NMR (DMSO-d₆): δ 4.99 (dd, 1H, J=1.37 and 17.1), 5.12 (d, 2H), 5.16 (dd, 1H, J=1.37 and 10.23 Hz), 6.04–6.12 (m, 1H), 6.39 (dd, 1H, J=2.44 and 8.39 Hz), 6.43 (s, 1H), 7.09–7.13 (m, 1H), 7.23–7.27 (ml, 1H), 7.51 (d, 1H), 7.75 (d, 1H), 9.59 (broad s, 1H), 10.03 (broad s, 1H);
MS (ESI) m/z 285 [M+H]+.

EXAMPLE 99

4-(7-fluoro-1-propyl-1H-indazole-3-yl)benzene-1,3-diol

Step 1: 3-(2,4-dimethoxyphenyl)-7-fluoro-1-propyl-1H-indazole

Prepared according to Method D step B from 3-(2,4-dimethoxyphenyl)-7-fluoro-1H-indazole (0.300 g, 1.10 mmol), sodium hydride (60% in oil, 0.058 g, 1.50 mmol) and iodopropane (0.195 mL, 2.00 mmol) to give the title compound (0.343 g) as a white solid.
¹H NMR (DMSO-d₆): δ 0.72 (t, 3H), 1.78–1.85 (m, 2H), 3.75 (s, 3H), 3.86 (s, 3H), 4.08–4.12 (m, 1H), 4.16–4.19 (m, 1H), 6.72 (dd, 1H, J=2.44 and 8.39 Hz), 6.78 (s, 1H), 6.90–6.94 (m, 1H), 6.98–7.02 (m, 1H), 7.11 (d, 1H), 7.28 (d, 1H).
MS (ESI) m/z 315 [M+H]+.

Step 2: 4-(7-fluoro-1-propyl-1H-indazole-3-yl)benzene-13-diol

Prepared according to Method D step C from 3-(2,4-dimethoxyphenyl)-7-fluoro-1-propyl-1H-indazole (0.332 g, 1.1 mmol), boron tribromide (0.830 mL, 8.8 mmol) and 1.0 mL of cyclohexene to give the product (0.303 g) as a white solid.

$^1$H NMR (DMSO-d$_6$): δ 0.85 (t, 3H), 1.84–1.89 (m, 2H), 4.47 (t, 2H), 6.39 (dd, 1H, J=2.44 and 8.39 Hz), 6.43 (s, 1H), 7.08–7.12 (m, 1H), 7.23–7.27(m, 1H), 7.52 (d, 1H), 7.75 (d, 1H), 9.59 (broad s, 1H), 10.07 (broad s, 1H).

MS (ESI) m/z 285 [M–H]–.

EXAMPLE 100

7-chloro-3-(4-methoxyphenyl)-1-thien-3-yl-1H-indazole

A mixture of -chloro-3-(4-methoxyphenyl)-1-propyl-1H-indazole (1.0 g, 3.93 mmol), 3-thienylboronic acid (1.0 g, 7.8 mmol), anhydrous copper(II)acetate (0.71 g, 3.9 mmol) and diisopropylethylamine (1.36 mL, 7.8 mmol) in 50 mL CH$_2$Cl$_2$ was stirred at ambient temperature overnight. The reaction mixture was preabsorbed on silica gel and the absorbed solid purified by flash chromatography (hexane, EtOAc: 3:1) to give the product (0.15 g) as a white solid, mp 111° C.

$^1$H NMR (DMSO-d$_6$): δ 3.83 (s, 3H), 7.11 (d, 2H), 7.29 (t, 1H), 7.37 (m, 1H), 7.55 (d, 1H), 7.68 (m, 1H), 7.90 (d, 2H), 8.08 (d, 1H).

MS (ESI) m/z 341 [M+H]+.

Anal. calcd for C$_{18}$H$_{13}$ClN$_2$OS: C, 63.43; H, 3.84; N, 8.22. Found: C, 63.29; H, 3.85; N, 7.88.

EXAMPLE 101

4-(7-chloro-1-thien-3-yl-1H-indazole-3-yl)phenol

Prepared according to Method D step C from -chloro-3-(4-methoxyphenyl)-1-thien-3-yl-1H-indazole (0.19 g, 0.56 mmol), boron tribromide (0.021 mL, 2.25 mmol) and 1.0 mL of cyclohexene to give the product (0.045 g) as a white solid.

$^1$H NMR (DMSO-d$_6$): δ 6.93 (d 2H), 7.27 (t, 1H), 7.365 (dd, 1H), 7.54 (d, 1H), 7.67 (dd, 1H), 7.78 (d, 2H), 7.86 (dd, 1H), 8.06 (d, 1H), 9.75 (s, 1H).

MS (ESI) m/z 325 [M–H]–.

EXAMPLE 102 methyl 3-(4-hydroxyphenyl)-2-isopropyl-2H-indazole-7-carboxylate

Step 1: 2-isopropyl 3-(4-methoxyphenyl)-7-trifluoromethyl-2H-indazole

Prepared according to Method D step B from 3-(4-methoxyphenyl)-7-trifluoromethyl-1H-indazole (1.0 g, 3.4 mmol), sodium hydride (60% in oil, 0.136 g, 3.4 mmol) and 2-iodopropane (0.34 mL, 3.4 mmol) to give the title compound (0.27 g) as a white solid.

$^1$H NMR (DMSO-d$_6$): δ 1.48 (d, 6H), 3.82 (s, 3H), 4.81 (m, 1H), 7.14 (m, 3H), 7.48 (t, 1H), 2H), 7.63 (dd, 2H).

Step 2: methyl 3-(4-hydroxyphenyl)-2-isopropyl-2H-indazole-7-carboxylate

Prepared according to Method D step C from 2-isopropyl-3-(4-methoxyphenyl)-7-trifluoromethyl-2H-indazole (0.27 g, 0.81 mmol), boron tribromide (0.31 mL, 3.2 mmol) and 1.0 mL of cyclohexene. The reaction mixture was quenched with methanol and allowed to stand at ambient temperature overnight. The reaction mixture was preabsorbed on silica gel and purified by flash chromatography (hexane-EtOAc, 2:1) to give the product (0.13 g) as an buff colored solid. mp 195–196° C.;

$^1$H NMR (DMSO-d$_6$): δ 1.52 (d, 6H), 3.89 (s, 3H), 4.84 (m, 1H), 6.99 (d, 2H), 7.10 (t, 1H), 7.36 (d, 2H), 7.71 (d, 1H), 7.93 (d, 1H), 9.93 (s, 1H);

MS (APCI) m/z 311 [M+H]+.

EXAMPLE 103

4-[3-(4-hydroxyphenyl)-1-propyl-1H-indazole-7-yl]phenol

Step 1: 7-(4-methoxyphenyl)-3-(4-methoxyphenyl)-1-propyl-1H-indazole

To a stirred solution of 7-chloro-3-(4-methoxyphenyl)-1-propyl-1H-indazole (0.10 g, 0.33 mmol) in anhydrous dioxane (3 mL) was added tris(dibenzylideneacetone)dipalladium(0) (0.004 g, 0.0043 mmol) and 1,3-bis(2,4,6-trimethylphenyl)imidazol-2-ylidene HCl (0.0035 g, 0.0099 mmol). 4-Methoxyphenylmagnesium bromide (1.2 mL, 0.5M in diethyl ether) was added and the reaction mixture degassed. The reaction was heated to 80° C. for 18 hours. The reaction mixture was partitoned with 1N HCl and ethyl acetate. The organic layer was washed with water and brine. After drying (Na$_2$SO$_4$), the organic phase was concentrated in vacuo to yield crude title compound. The oil was purified by flash chromatography (silica gel, hexane/ethyl acetate, 5:1) to provide the title compound as a white solid (0.028 g).

$^1$H NMR (DMSO-d$_6$): δ 0.487 (t, 3H), 1.43(m, 2H), 3.82 (s, 6H), 3.89 (m, 2H), 7.08 (m, 4H), 7.17 (m, 1H), 7.25 (m, 2H), 7.40 (d, 2H), 7.86 (d, 2H), 7.99 (d, 1H).

MS (ESI) m/z 373 [M+H]+.

Step 2: 4-[3-(4-hydroxyphenyl)-1-propyl-1H-indazole-7-yl]phenol

Prepared according to Method D step C from 7-(4-methoxyphenyl)-3-(4-methoxy-phenyl)-1-propyl-1H-indazole (0.04 g, 0.11 mmol), boron tribromide (0.04 mL, 0.43 mmol) and 0.1 mL of cyclohexene to give the product (0.029 g) as an light yellow solid.

$^1$H NMR (DMSO-d$_6$): δ 0.492 (t, 3H), 1.42 (m, 2H), 3.89 (m, 2H), 6.89 (m, 4H), 7.14 ( )m, 1H), 7.19 (m, 1H), 7.25 (d, 2H), 7.73 (d, 2H), 7.93 (d, 1H), 9.60 (s, 1H) 9.634 (s, 1H).

MS (ESI) m/z 343 [M–H]–.

EXAMPLE 104

4-[7-(4-Fluorophenyl)-1-propyl-1H-indazole-3-yl]phenol

Step 1: 7-(4-Fluorophenyl)-3-(4-methoxyphenyl)-1-propyl-1H-indazole

To a stirred solution of 7-chloro-3-(4-methoxyphenyl)-1-propyl-1H-indazole (0.247 g, 0.82 mmol) in anhydrous dioxane (6 mL) was added tris(dibenzylideneacetone)-dipalladium(0) (0.015 g, 0.016 mmol) and 1,3-bis(2,6-diisopropylphenyl)imidazol-2-ylidene HCl (0.014 g, 0.033 mmol). 4-Fluorophenylmagnesium bromide (0.74 mL, 1.48 mmol, 2M in diethyl ether) was added and the reaction heated to 80° C. for 18 hours. After this time an additional 50% of reagents were added and the reaction heated for an additional 18 hours. The reaction mixture was treated with 1N aqueous hydrochloric acid solution and extracted with ethyl acetate. The organic layer washed with water and saturated aqueous sodium chloride solution. After drying over anhydrous magnesium sulfate, the organic phase was filtered and the filtrate evaporated in vacuo to yield crude title compound. The oil was purified by silica gel column chromatography eluting with hexane/ethyl acetate (5/1) to provide the title compound as a white solid (0.139 g, 0.39 mmol, 47%).

Mp 110–111° C.;
$^1$H NMR (500 MHz, DMSO-d$_6$) δ 0.49 (t, 3H, J=7.3 Hz), 1.42 (q, 2H, J=14.6, 7.4 Hz), 3.82 (s, 3H), 3.86 (t, 3H, J=7.3 Hz), 7.08 (d, 2H, J=8.2 Hz), 7.20–7.27 (m, 2H), 7.55 (d, 2H, J=6.0 Hz), 7.36 (t, 2H, J=8.5 Hz), 7.86 (d, 2H, J=8.4 Hz), 8.02 (d, 1H, J=8.4 Hz).

MS (ESI) m/z 361 [M+H]+.

Anal. calcd for C$_{23}$H$_{21}$FN$_2$O: C, 76.65; H, 5.87; N, 7.77. Found: C, 76.37; H, 5.82; N, 7.90.

Step 2: 4-[7-(4-Fluorophenyl)-1-propyl-1H-indazole-3-yl]phenol

Prepared according to Method D step C from 7-(4-Fluorophenyl)-3-(4-methoxyphenyl)-1-propyl-1H-indazole (0.125 g, 0.35 mmol), BBr$_3$ (0.066 mL, 0.7 mmol) to give the title compound as a white solid (0.087 g, 0.25 mmol, 72%).

mp 201–202° C.;
$^1$H NMR (DMSO-d$_6$): δ 0.49 (t, 3H, J=7.4 Hz), 1.42 (m, 2H, J=14.9, 7.4 Hz), 3.85 (t, 3H, J=7.5 Hz), 6.90 (d, 2H, J=8.6 Hz), 7.18-7.25 (m, 2H), 7.34 (t, 2H, J=8.4 Hz), 7.53–7.56 (m, 2H), 7.86 (d, 2H, J=8.6 Hz), 8.00 (q, 1H, J=8.0, 1.0 Hz).

MS (ESI) m/z 347 [M+H]+.

Anal. calcd for C$_{22}$H$_{19}$FN$_2$O.0.15 H$_2$O: C, 75.69; H, 5.57; N, 8.02. Found: C, 75.49; H, 8.02.

EXAMPLE 105

4-(7-Morpholin-4-yl-1-propyl-1H-indazole-3-yl)phenol

Step 1: 3-(4-Methoxyphenyl)-7-morpholin-4-yl-1-propyl-1H-indazole

To a stirred solution of 7-chloro-3-(4-methoxyphenyl)-1-propyl-1H-indazole (0.218 g, 0.73 mmol) in anhydrous degassed dimethoxyethane (3 mL) was added morpholine (0.076 mL, 0.84 mmol) and sodium t-butoxide (0.098 g, 1.02 mmol). Tris(dibenzylidene-acetone)dipalladium(0) (0.010 g, 0.011 mmol) and 2-dicyclohexyl phosphino-2'-(N,N-dimethylamino)biphenyl (0.09 g, 0.23 mmol) were added and the reaction refluxed for 90 minutes. The reaction was cooled to room temperature and water added. The mixture was extracted with ethyl acetate and the organic layer washed with water and saturated aqueous sodium chloride solution. After drying over anhydrous magnesium sulfate, the organic phase was filtered and the filtrate evaporated in vacuo to yield crude title compound. The oil was purified by silica gel column chromatography eluting with hexane/ethyl acetate (5/1 to 3/1) to provide the title compound as a white solid (0.157 g, 0.45 mmol, 63%). An analytical sample was crystallized from hexane.

mp 86–87° C.;
$^1$H NMR (DMSO-d$_6$): δ 0.86 (t, 3H, J=7.3 Hz), 1.82 (m, 2H, J=14.5, 7.2 Hz), 2.93–3.03 (m, 4H), 3.70–3.74 (m, 2H), 3.81 (s, 3H), 3.91–3.93 (m, 2H), 4.63 (t, 2H, J=7.1 Hz), 7.06 (d, 2H, J=8.1 Hz), 7.18–7.25 (m, 2H), 7.72 (d, 2H, J=8.1 Hz), 7.82 (t, 2H, J=8.1 Hz),

MS (ESI) m/z 352 [M+H]+.

Anal. calcd for C$_{21}$H$_{25}$N$_3$O$_2$: C, 71.77; H, 7.17; N, 11.96. Found: C, 71.43; H, 7.31; N, 11.95.

Step 2: 4-(7-Morpholin-4-yl-1-propyl-1H-indazole-3-yl)phenol

Prepared according to Method D step C from 3-(4-Methoxyphenyl)-7-morpholin-4-yl-1-propyl-1H-indazole (0.140 g, 0.4 mmol), BBr$_3$ (0.076 mL, 0.8 mmol) to give title compound as a white solid which was recrystallized from ethyl acetate and hexane (0.05 g, 0.15 mmol, 37%).

mp 187–188° C.;
$^1$H NMR (DMSO-d$_6$): δ 0.86 (t, 3H, J=7.4 Hz), 1.78–1.85 (m, 2H), 2.92–3.02 (m, 4H), 3.72 (t, 2H, J=10.6 Hz), 3.91 (d, 2H, J=10.7 Hz), 4.61 (t, 2H, J=7.3 Hz), 6.88 (d, 2H), J=8.7 Hz), 7.12 (t, 1H, J=7.7 Hz), 7.17 (t, 1H, J=6.9 Hz), 7.70 (m, 3H), 9.60 (bd, 1H).

MS (ESI) m/z 336 [M−H]−.

Anal. calcd for C$_{20}$H$_{23}$N$_3$O$_2$.0.25 H$_2$O: C, 70.26; H, 6.93; N, 12.29. Found: C, 70.37; H, 6.67; N, 12.25.

EXAMPLE 106

2-Chloro-4-(7-chloro-1-propyl-1H-indazole-3-yl)phenol

Step 1 (3-Chloro-2-fluororhenyl)(3-chloro-4-methoxyphenyl)methanone

Prepared according to Method A step B from 3-chloro-2-fluoro-N-methoxy-N-methyl-benzamide (3.7 g, 17.0 mmol) and bromo(3-chloro-4-methoxyphenyl)magnesium (100 mL, 2M in diethyl ether). The title compound was obtained as a white solid (2.3 g, 7.69 mmol, 45%).

mp 130–131° C.;
$^1$H NMR (DMSO-d$_6$): δ 3.97 (s, 3H), 7.30 (d, 1H, J=8.7 Hz), 7.86 (t, 1H, J=7.9 Hz), 7.53 (m, 1H), 7.72 (q, 1H, J=8.7, 0.9 Hz), 7.84 (m, 2H).

Anal. calcd for C$_{14}$H$_9$Cl$_2$FO$_2$: C, 56.21; H, 3.03; N, 0.00. Found: C, 55.99; H, 2.81; N, 0.01.

Step 2: 7-Chloro-3-(3-chloro-4-methoxyphenyl)-1H-indazole

Prepared according to Method D, Step A from (3-chloro-2-fluorophenyl)(3-chloro-4-methoxyphenyl)methanone (2.04 g, 6.82 mmol), hydrazine hydrate (2.5 mL), dimethylaminopyridine (0.97 g) and pyridine (12.5 mL). The title compound was obtained as a white solid and recrystallized from ethyl acetate/hexane (1.74 g, 5.94 mmol, 87%).

mp 198–199° C.;
$^1$H NMR (DMSO-d$_6$): δ 3.93 (s, 3H), 7.21 (t, 1H, J=7.8 Hz), 7.30 (d, 1H, J=8.6Hz), 7.50 (d, 1H, J=7.3 Hz), 7.92 (dd, 1H, J=8.6, 2.1 Hz), 7.96 (d, 1H, J=1.7Hz), 8.00 (d, 1H, J=8.2).

MS (ESI) m/z 293 [M+H]+.

Anal. calcd for C$_{14}$H$_{10}$Cl$_2$N$_2$O: C, 57.36; H, 3.44; N, 9.56. Found: C, 57.06; H, 3.49; N, 9.96.

Step 3: 7-chloro-3-(3-chloro-4-methoxyphenyl)-1-propyl-1H-indazole

Prepared according to Method D Step B from 7-chloro-3-(3-chloro-4-methoxyphenyl)-1H-indazole (1.0 g, 3.4 mmol), sodium hydride (0.15 g, 60% in oil) in DMF followed by propyl bromide (0.4 mL). The title compound was obtained as an oil (0.94 g, 2.8 mmol, 82%).

¹H NMR (DMSO-d₆): δ 0.89 (t, 3H, J=7.4 Hz), 1.87 (m, 2H), 4.71 (t, 2H, J=7.2 Hz), 7.21 (t, 1H, J=7.8 Hz), 7.29 (d, 1H, J=8.6 Hz), 7.50 (d, 1H, J=7.3 Hz), J=8.6,2.1 Hz), 7.90 (t, 1H, J=1.0 Hz), 7.99 (d, 1H, J=8.2);

MS (ESI) m/z 335 [M+H]+.

Anal. calcd for $C_{17}H_{16}Cl_2N_2O$: C, 60.91; H, 4.81; N, 8.36. Found: C, 60.97; H, 4.78; N, 8.38.

Step 4: 2-Chloro-4-(7-chloro-1-propyl-1H-indazole-3-yl)phenol

Prepared according to Method D step C from 7-Chloro-3-(3-chloro-4-methoxyphenyl)-1-propyl-1H-indazole (0.39 g, 1.18mmol), $BBr_3$ (0.11 mL, 1.17 mmol) to give the title compound as a white solid (0.24 g, 0.75 mmol, 64%).

mp 145–146° C.;

¹H NMR (DMSO-d₆): δ 0.88 (t, 3H, J=7.4 Hz), 1.88 (m, 2H), 4.70 (t, 2H, J=7.3Hz), 7.11 (d, 1H, J=8.4 Hz), 7.19 (dd, 1H, J=8.2,7.5 Hz), 7.51 (dd, 1H, J=7.3 Hz and 0.9 Hz), 7.71 (dd, 1H, J=8.4 Hz and 2.1 Hz), 7.81 (t, 1H, J=1.1 Hz), 7.96 (dd, 1H, J=8.1 Hz and 0.8 Hz), 10.48 (bd, 1H).

MS (ESI) m/z 321 [M+H]+.

Anal. calcd for $C_{16}H_{14}Cl_2N_2O$: C, 59.83; H, 4.39; N, 8.72. Found: C, 59.93; H, 4.21; N, 8.

EXAMPLE 107

4-(7-Chloro-1-propyl-1H-indazole-3-yl)-2-fluorophenyl 3,3-dimethylbutanoate

Step 1: (3-chloro-2-fluorophenyl)(3-fluoro-4-methoxyphenyl)methanone

Prepared according to Method A step B from 3-chloro-2-fluoro-N-methoxy-N-methylbenzamide (4.0 g, 18.4 mmol) and bromo(3-fluoro-4-methoxyphenyl)magnesium (100 mL, 2M in diethyl ether). The title compound was obtained as a white solid (1.65 g, 5.85 mmol, 32%).

mp 103–104° C.;

¹H NMR (DMSO-d₆): δ 3.94 (s, 3H), 7.31 (t, 1H, J=8.4 Hz), 7.39 (t, 1H, J=7.8 Hz), 7.51 (t, 1H, J=6.9 Hz), 7.56 (d, 1H, J=8.6 Hz), 7.65 (d, 1H, J=11.9 Hz), 7.83 (t, 1H, J=7.6 Hz).

MS (EI) m/z 282;

Anal. calcd for $C_{14}H_9ClF_2O_2$: C, 59.49; H, 3.21; N, 0.00. Found: C, 59.12; H, 2.93; N, 0.04.

Step 2: 7-Chloro-3-(3-fluoro-4-methoxyphenyl)-1H-indazole

Prepared according to Method D, Step A from (3-chloro-2-fluorophenyl)(3-fluoro-4-methoxyphenyl)methanone (0.80 g, 2.83 mmol), hydrazine hydrate (1 mL), dimethylaminopyridine (0.390 g) and pyridine (5 mL). The reaction mixture was combined with a previous batch at this stage and the title compound was obtained as a white solid and recrystallized from ethyl acetate/hexane (1.30 g, 4.79 mmol, 83%).

mp 195–196° C.;

¹H NMR (DMSO-d₆): δ 3.91 (s, 3H), 7.20 (t, 1H, J=7.9 Hz), 7.31 (t, 1H, J=8.9 Hz), 7.50 (d, 1H, J=7.3 Hz), 7.75 (m, 2H), 8.00 (d, 1H, J=8.1 Hz), 13.71 (s, 1H).

MS (ESI) m/z 275 [M–H]–.

Anal. calcd for $C_{14}H_{10}ClFN_2O$: C, 60.77; H,3.64N, 10.12. Found: C, 60.42; H, 3.56; N, 10.12.

Step 3: 7-Chloro-3-(3-fluoro-4-methoxyyhenyl)-1-propyl-1H-indazole

Prepared according to Method D Step B from 7-Chloro-3-(3-fluoro-4-methoxyphenyl)-1H-indazole (1.0 g, 3.6 mmol), sodium hydride (0.16 g, 60% in oil) in DMF followed by propyl bromide (0.42 mL). The title compound was obtained as an oil (0.86 g, 2.7 mmol, 75%).

mp 58–59° C.;

¹H NMR (DMSO-d₆): δ 0.89 (t, 3H, J=7.9 Hz), 1.88 (m, 2H), 3.90 (s, 3H), 4.71 (t, 2H, J=7.2 Hz), 7.20 (t, 1H, J=7.8 Hz), 7.31 (t, 1H, J=8.9 Hz), 7.52 (d, 1H, J=7.5 Hz), 7.70 (m, 2H), 8.01 (d, 1H, J=8.1 Hz).

MS (ESI) m/z 319 [M+H]+.

Anal. calcd for $C_{17}H_{16}ClFN_2O$: C, 64.05; H, 5.06; N, 8.79. Found: C, 63.85; H, 4.75; N, 8.84.

Step 4: 4-(7-Chloro-1-propyl-1H-indazole-3-yl)-2-fluorophenol

Prepared according to Method D step C from 7-Chloro-3-(3-fluoro-4-methoxyphenyl)-1-propyl-1H-indazole (0.26 g, 0.82 mmol), $BBr_3$ (0.15 mL, 1.63 mmol) to give the title compound as a white solid (0.12 g, 0.39 mmol, 48%).

mp 134–135° C.;

¹H NMR (DMSO-d₆): δ 0.88 (t, 3H, J=7.4 Hz), 1.86 (m, 2H), 4.70 (t, 2H, J=7.3 Hz), 7.09 (t, 1H, J=8.8 Hz), 7.18 (t, 1H, J=7.9 Hz), 7.50 (d, 1H, J=7.2 Hz), 7.56 (d, 1H, J=8.4 Hz), 7.61 (dd, 1H, J=12.4, 2.0 Hz), 8.01 (d, 1H, J=8.2 Hz), 10.17 (bd, 1H.

MS (ESI) m/z 305 [M+H]+.

Anal. calcd for $C_{16}H_{14}ClFN_2O$: C, 63.06; H, 4.63; N, 9.19. Found: C, 62.76; H, 4.42 N, 9.22.

Step 5: 4-(7-Chloro-1-propyl-1H-indazole-3-yl)-2-fluorophenyl 3,3-dimethylbutanoate To a solution of 4-(7-chloro-1-propyl-1H-indazole-3-yl)-2-fluorophenol (0.10 g, 0.33 mmol) in dichloromethane (20 mL) at –78° C. was added diisopropylethylamine (0.70 mL, 0.41 mmol), 3,3-dimethylbutanoyl chloride (0.05 mL, 0.35 mmol) and catalytic amount of 4-(dimethylamino)pyridine. The reaction was stirred at this temperature for 30 minutes. The mixture was diluted with dichloromethane and the organic layer washed with 1n hydrochloric acid solution, water and saturated aqueous sodium chloride solution. After drying over anhydrous magnesium sulfate, the organic phase was filtered and the filtrate evaporated in vacuo to yield crude title compound. The oil was purified by silica gel column chromatography eluting with hexane/ethyl acetate (5/1) to provide the title compound as a white solid (0.11 g, 0.27 mmol, 83%).

mp 58–59° C.;

¹H NMR (DMSO-d₆): δ 1.10 (s, 9H), 4.74 (t, 2H, J=7.2 Hz), 7.23 (t, 1H, J=7.9Hz), 7.42 (t, 1H, J=8.2 Hz), 7.55 (d, 1H, J=7.5 Hz), 7.80 (d, 1H, J=8.4 Hz), 7.85 (dd, 1H, J=11.4, 1.8 Hz), 8.07 (d, 1H, J=8.1 Hz).

MS (ESI) m/z 403 [M+H]+.

Anal. calcd for $C_{22}H_{24}ClFN_2O_2$: C, 65.59; H, 6.00, N; 6.95. Found: C, 65.36; H, 6.14 N:6.91.

EXAMPLE 108

(7-Chloro-1-cyclopentyl-1H-indazole-3-yl)-2-fluorophenol

Step 1: 7-Chloro-1-cyclopentyl-3-(3-fluoro-4-methoxyphenyl)-1H-indazole

Prepared according to Method D Step B from 7-chloro-3-(3-fluoro-4-methoxyphenyl)-1H-indazole (0.17 g, 0.61 mmol), sodium hydride (0.03 g, 60% in oil) in DMF followed by cyclopropyl bromide (0.07 mL). The title compound was obtained as a white solid (0.13 g, 0.38 mmol, 63%). The material was used directly in Step 2.

Step 2: (7-Chloro-1-cyclopentyl-1H-indazole-3-yl)-2-fluorophenol

Prepared according to Method D step C from 7-Chloro-1-cyclopentyl-3-(3-fluoro-4-methoxyphenyl)-1H-indazole (0.13 g, 0.38 mmol) and BBr$_3$ (0.07 mL, 0.76 mmol) to give the title compound as a white solid (0.072 g, 0.22 mmol, 58%).

mp 150–151° C.;

$^1$H NMR (DMSO-d$_6$): δ 1.70 (m, 2H), 1.90 (m, 2H), 2.13 (m, 4H), 5.82 (dd, 1H, J=13.7, 6.8 Hz), 7.10 (m, 1H), 7.18 (t, 1H, J=7.9 Hz), 7.49 (dd, 1H, J=7.4, 0.7 Hz), 7.56 (dd, 1H, J=8.3, 1.3 Hz), 7.61 (dd, 1H, J=12.3, 1.9 Hz), 7.99 (d, 1H, J=7.8 Hz), 10.11 (s, 1H).

MS (ESI) m/z 329 [M–H]–.

Anal. calcd for C$_{18}$H$_{16}$ClFN$_2$O: C, 65.36; H, 4.88; N, 8.47. Found: C, 65.19; H, 4.66 N; 8.12.

EXAMPLE 109

2-Fluoro-4-(7-phenyl-1-propyl-1H-indazole-3-yl)phenol

Step 1: 3-(3-Fluoro-4-methoxyphenyl)-7-phenyl-1-propyl-1H-indazole

To a stirred solution of 7-chloro-3-(3-fluoro-4-methoxyphenyl)-1-propyl-1H-indazole (0.38 g, 1.18 mmol) in anhydrous dioxane (6 mL) was added tris(dibenzylideneacetone)-dipalladium(0) (0.022 g, 0.024 mmol) and 1,3-bis(2,6-diisopropylphenyl)imidazol-2-ylidene HCl (0.02 g, 0.047 mmol). Phenylmagnesium bromide (0.71 mL, 1.40 mmol, 2M in diethyl ether) was added and the reaction heated to 80° C. for 18 hours. The reaction mixture was treated with 1 N hydrochloric acid solution and extracted with ethyl acetate. The organic layer washed with water and saturated aqueous sodium chloride solution. After drying over anhydrous magnesium sulfate, the organic phase was filtered and the filtrate evaporated in vacuo to yield crude title compound. The oil was purified by silica gel column chromatography eluting with hexane/ethyl acetate (3/1) to provide the title compound as a white solid (0.28 g, 0.78 mmol, 66%). This material was used directly in step 2.

Step 2: 2-Fluoro-4-(7-phenyl-1-propyl-1H-indazol-3-yl)phenol

Prepared according to Method D step C from 3-(3-Fluoro-4-methoxyphenyl)-7-phenyl-1-propyl-1H-indazole (0.28 g, 0.78 mmol), BBr$_3$ (0.073 mL, 0.78 mmol) gave title compound as a white solid (0.156 g, 0.45 mmol, 58%).

mp 177–178° C.;

$^1$H NMR (DMSO-d$_6$): δ 0.45 (t, 3H, J=7.4 Hz), 1.41 (m, 2H), 3.85 (t, 2H, J=7.5Hz), 7.10 (t, 1H, J=8.9 Hz), 7.18 (t, 1H, J=7.9 Hz), 7.48–7.52 (m, 5H), 7.54–7.65 (m, 2H), 8.02 (dd, 1H, J=7.9, 0.9 Hz), 10.05 (bd, 1H).

MS (ESI) m/z 347 [M+H]+.

Anal. calcd for C$_{22}$H$_{19}$FN$_2$O.0.15 CHCl$_3$: C, 73.03; H, 5.30; N, 7.69. Found: C, 73.16; H, 4.99 N, 7.89.

EXAMPLE 110

4-(7-phenyl-2-propyl-2H-indazol-3-yl)phenol

Step 1: 3-(4-methoxyphenyl)-7-phenyl-2-propyl-2H-indazole

To a stirred solution of 7-Chloro-3-(4-methoxyphenyl)-2-propyl-2H-indazole (0.200 g, 0.66 mmol) in anhydrous dioxane (6 mL) was added tris(dibenzylideneacetone)-dipalladium(0) (0.0128 g, 0.013 mmol) and 1,3-bis(2,6-diisopropylphenyl)imidazol-2-ylidene.HCl (0.011 g, 0.07 mmol). Phenylmagnesium bromide (0.4 mL, 1.20 mmol, 3M in diethyl ether) was added and the reaction heated to 80° C. for 3 hours. After this time an additional equivalent of reagents was added and the reaction heated for an additional 18 hours. The reaction mixture was treated with 1N aqueous hydrochloric acid solution and extracted with ethyl acetate. The organic layer washed with water and saturated aqueous sodium chloride solution. After drying over anhydrous magnesium sulfate, the organic phase was filtered and the filtrate evaporated in vacuo to yield crude title compound. The oil was purified by silica gel column chromatography eluting with hexane/ethyl acetate (5/1) to provide the title compound as a white solid (0.178 g, 0.52 mmol, 78%).

mp 128–129° C.;

$^1$H NMR (DMSO-d$_6$): δ $^1$H NMR (DMSO-d$_6$): δ0.77 (t, 3H, J=7.4 Hz), 1.86 (q, 2H, J=7.3 Hz), 3.86 (s, 3H), 4.36 (t, 2H, J=7.6 Hz), 7.13 (t, 1H, J=6.9 Hz), 7.17 (d, 2H, J=6.8 Hz), 7.37 (t, 1H, J=7.3 Hz), 7.50 (m, 6H), 8.09 (d, 2H, J=7.8 Hz).

MS (ESI) m/z 343 [M+H]+.

Anal. calcd for C$_{23}$H$_{22}$N$_2$O: C, 80.67; H, 6.48; N, 8.18. Found: C, 80.99; H, 6.33; N, 8.28.

Step 2: 4-(7-phenyl-2-propyl-2H-indazol-3-yl)phenol

To a solution of 3-(4-methoxyphenyl)-7-phenyl-2-propyl-2H-indazole (0.140 g, 0.43 mmol) in CH$_2$Cl$_2$ (5 mL) was added BBr$_3$ (0.081 mL, 0.865 mmol) at –78° C. The solution was stirred for 15 minutes and allowed to stand overnight in the refrigerator. The reaction was quenched with NH$_4$OH (10 mL) and extracted with CH$_2$Cl$_2$. The organic layer was washed with water and dried (MgSO$_4$). The reaction was purified by flash chromatography (5/1 hexane/ethyl Acetate) to give the title compound as a white solid (0.066 g, 0.15 mmol, 34%).

mp 207–208° C.;

$^1$H NMR (DMSO-d$_6$): δ 0.78 (t, 3H, J=7.3 Hz), 1.86 (q, 2H, J=7.3 Hz), 4.35 (t, 2H, J=7.2 Hz), 6.99 (d, 2H, J=8.7 Hz), 7.12 (t, 1H, 7.6 Hz), 7.45 (m, 7H), 8.09 (d, 2H, J=7.9 Hz), 9.90 (s, 1H).

MS (ESI) m/z 329 [M+H]+.

Anal. calcd for C$_{22}$H$_{20}$N$_2$O.0.10 H$_2$O: C, 80.02; H, 6.17; N, 8.48. Found: C, 79.73; H, 6.08 N, 8.62.

EXAMPLE 111

4-(7-phenyl-1-propyl-1H-indazol-3-yl)phenol

Step 1: 3-(4-methoxyphenyl)-7-phenyl-1-propyl-1H-indazole

To a stirred solution of 7-chloro-3-(4-methoxyphenyl)-1-propyl-1H-indazole (0.600 g, 0.1.98 mmol) in anhydrous dioxane (8 mL) was added tris(dibenzylideneacetone)-dipalladium(0) (0.036 g, 0.04 mmol) and 1,3-bis(2,6-diisopropylphenyl)imidazol-2-ylidene HCl (0.036 g, 0.08 mmol). Phenylmagnesium bromide (1.18 mL, 3.56 mmol, 3M in diethyl ether) was added and the reaction heated to 80° C. for 3 hours. After this time an additional equivalent of reagents was added and the reaction heated for an additional 18 hours. The reaction mixture was treated with 1N aqueous hydrochloric acid solution and extracted with ethyl acetate. The organic layer washed with water and saturated aqueous sodium chloride solution. After drying over anhydrous magnesium sulfate, the organic phase was filtered and the filtrate evaporated in vacuo to yield crude title compound. The oil was purified by silica gel column chromatography eluting with hexane/ethyl acetate (5/1) to provide the title compound as a white solid (0.405 g, 1.18 mmol, 59%).

mp 58–59° C.;

$^1$H NMR (DMSO-$d_6$): δ 0.45 (t, 3H, J=7.3 Hz), 1.40 (q, 2H, J=7.3 Hz), 3.82 (m, 5H) 7.09 (d, 2H, J=8.8 Hz), 7.22 (m, 2H), 7.51 (m, 5H), 7.86 (d, 2H, J=8.7 Hz), 8.01 (d, 1H, J=7.5 Hz).

MS (ESI) m/z 343 [M+H]+.

Anal. calcd for $C_{23}H_{22}N_2O \cdot 0.15\ H_2O$: C, 80.04; H, 6.51; N, 8.12. Found: C, 79.75; H, 6.32 N, 8.16.

Step 2:
4-(7-phenyl-1-propyl-1H-indazol-3-yl)phenol

To a solution of 3-(4-methoxyphenyl)-7-phenyl-1-propyl-1H-indazole (0.375 g, 1.09 mmol) in $CH_2Cl_2$ (15 mL) was added $BBr_3$ (0.207 mL, 2.19 mmol) at −78° C. The solution was stirred for 15 minutes and allowed to stand overnight in the refrigerator. The reaction was quenched with $NH_4OH$ (20 mL) and extracted with $CH_2Cl_2$. The organic layer was washed with water and dried ($MgSO_4$). The reaction was purified by flash chromatography (5/1 hexane/ethyl acetate) to give the title compound as a white solid (0.147 g, 0.45 mmol, 41%).

mp 171–172° C.;

$^1$H NMR (DMSO-$d_6$): 0.45 (t, 3H, J=7.3 Hz), 1.40 (q, 2H, J=7.3 Hz), 3.83 (t, 2H, J=7.5 Hz), 6.91 (d, 2H, J=8.7 Hz), 7.20 (m, 2H), 7.51 (m, 5H), 7.74 (d, 2H, J=8.7 Hz, 7.99 (d, 1H, J=7.5 Hz), 9.63 (s, 1H).

MS (ESI) m/z 329 [M+H]+.

Anal. calcd for $C_{22}H_{20}N_2O \cdot 0.05\ H_2O$: C, 80.24; H, 6.15; N, 8.51. Found: C, 79.89; H, 6.11 N, 8.42.

General Method E
4-(1-cyclopentyl-7-fluoro-1H-indazol-3-yl)phenolic ester

To a stirred solution of 4-(1-cyclopentyl-7-fluoro-1H-indazol-3-yl)phenol (1 equivalent) and diisopropylethyl amine (1 equivalent) in $CH_2Cl_2$ (0.2 molar) was added 1 equivalent of an acid chloride. The reaction mixture was stirred at ambient temperature for 3 hours. The reaction mixture was diluted with additional $CH_2Cl_2$ and washed with 1 N HCl. The organic phase was filtered through a plug of silica gel and concentrated to an oil. The crystalline ester was obtained with the appropriate solvent

EXAMPLE 112

4-(1-cyclopentyl-7-fluoro-1H-indazol-3-yl)phenyl pivalate

Prepared according to Method E from 4-(1-cyclopentyl-7-fluoro-1H-indazol-3-yl)phenol (0.30 g, 1.0 mmol), pivaloyl chloride (0.148 mL, 1.2 mmol) and N,N-diisopropylethyl-amine (0.21 mL, 1.2 mmol) to give 0.31 g of the title compound as a white solid, mp 105° C.

$^1$H NMR (DMSO-$d_6$): δ 1.328 (s, 9H), 1.715 (m, 2H), 1.895 (m, 2H), 2.15 (m, 4H), 5.299 (m, 1H), 7.19 (m, 1H), 7.25 (d, 2H), 7.28 (m, 1H), 7.86 (d, 1H), 7.96 (d, 2H).

MS (ESI) m/z 381 [M+H]+.

EXAMPLE 113

4-(1-cyclopentyl-7-fluoro-1H-indazol-3-yl)phenyl 3,3-dimethylbutanoate

Prepared according to Method E from 4-(1-cyclopentyl-7-fluoro-1H-indazol-3-yl)phenol (0.30 g, 1.0 mmol), 3,3-dimethylbutanoyl chloride (0.167 mL, 1.2 mmol) and N,N-diisopropylethylamine (0.21 mL, 1.2 mmol) to give 0.347 g of the title compound as a white solid, mp 74–75° C.;

$^1$H NMR (DMSO-$d_6$): δ 1.103 (s, 9H), 1.718 (m, 2H), 1.897 (m, 2H), 2.157 (m, 4H), 2.5 (s, 2H), 5.30 (m, 1H), 7.19 (m, 1H), 7.25 (d, 2H), 7.28 (m, 1H), 7.86 (d, 1H), 7.97 (d, 2H.

MS (ESI) m/z 395 [M+H]+.

EXAMPLE 114

4-(1-cyclopentyl-7-fluoro-1H-indazol-3-yl)phenyl acetate

Prepared according to Method E from 4-(1-cyclopentyl-7-fluoro-1H-indazol-3-yl)phenol (0.30 g, 1.0 mmol), acetyl chloride (0.086 mL, 1.2 mmol) and N,N-diisopropylethylamine (0.21 mL, 1.2 mmol) to give 0.31 g to the title compound as a white solid, mp 90–91° C.;

$^1$H NMR (DMSO-$d_6$): δ 1.714 (m, 2H), 1.89 (m, 2H), 2.15 (m, 4H), 2.30 (s, 3H), 5.297 (m, 1H), 7.188 (m, 1H), 7.28 (m, 3H), 7.86 (d, 1H), 7.97 (d, 2H).

MS (ESI) m/z 339 [M+H]+.

EXAMPLE 115

4-(1-cyclopentyl-7-fluoro-1H-indazol-3-yl)phenyl propionate

Prepared according to Method E from 4-(1-cyclopentyl-7-fluoro-1H-indazol-3-yl)phenol (0.30 g, 1.0 mmol), propanoyl chloride (0.105 mL, 1.2 mmol) and N,N-diisopropylethylamine (0.21 mL, 1.2 mmol) to give 0.284 g to the title compound as a white solid, mp 60–61° C.;

$^1$H NMR (DMSO-$d_6$): δ 1.154 (t, 3H), 1.712 (m, 2H), 1.892 (m, 2H), 2.15 (m, 4H), 2.63 (q, 2H), 5.298 (m, 1H), 7.19 (m, 1H), 7.27 (m, 3H), 7.86 (d, 1H), 7.96 (d, 2H).

MS (ESI) m/z 353 [M+H]+.

EXAMPLE 116

4-(1-cyclopentyl-7-fluoro-1H-indazol-3-yl)phenyl N-(tert-butoxycarbonyl)glycylglycinate A solution of 4-(1-cyclopentyl-7-fluoro-1H-indazol-3-yl)phenol (0.30 g, 1.0 mmol), N-(tert-butoxycarbonyl)glycylglycine (0.232 g, 1.0 mmol), N,N-dicylohexylcarbodiimide (0.206 g, 1.0 mmol) and DMAP (0.122 g, 1.0 mmol) in 10 mL of $CH_2Cl_2$ was stirred overnight at ambient temperature. The reaction mixture was diluted with $CH_2Cl_2$ and filtered through a plug of silica gel. The gel was rinsed with additional $CH_2Cl_2$. The combined filtrates were concentrated in vacuo to give 0.35 g to the title compound as a white solid, mp 103–104° C.;

¹H NMR (DMSO-d₆): δ 1.368 (s, 9H), 1.716 (m, 2H), 1.895 (m, 2H), 2.14 (m, 4H), 3.62 (d, 2H), 4.15 (d, 2H), 5.30 (m, 1H), 7.06 (m, 1H), 7.19 (m, 1H), 7.27 (m, 3H) 7.86 (d, 1H), 7.98 (d, 2H), 8.38 (m, 1H).

MS (ESI) m/z 511 [M+H]+.

Anal. calcd for $C_{27}H_{31}FN_4O_5$: C, 63.52; H, 6.12; N, 10.97; Found: C, 63.37; H, 6.29. N, 11.01.

EXAMPLE 117

1-tert-butyl 5-[4-(1-cyclopentyl-7-fluoro-1H-indazol-3-yl)phenyl] N-(tert-butoxycarbonyl)-L-glutamate A solution of 4-(1-cyclopentyl-7-fluoro-1H-indazol-3-yl) phenol (0.30 g, 1.0 mmol), 1-t-butyl-N-(tert-butoxycarbonyl)-L-glutamate (0.303 g, 1.0 mmol), N,N-dicylohexylcarbodiimide (0.206 g, 1.0 mmol) and DMAP (0.122 g, 1.0 mmol) in 10 mL of CH₂Cl₂ was stirred overnight at ambient temperature. The reaction mixture was diluted with CH₂Cl₂ and filtered through a plug of silica gel. The gel was rinsed with additional CH₂Cl₂. The combined filtrates were concentrated in vacuo to give 0.39 g to the title compound as a white solid.

mp 92–93° C.;

¹H NMR (DMSO-d₆): δ 1.40 (d, 18H), 1.717 (m, 2H), 1.90 (m, 2H), 2.05 (m, 1H), 2.15 (m, 4H), 2.69 (m, 2H), 3.93 (m, 1H), 5.30 (m, 1H), 7.19 (m, 1H), 7.28 (m, 3H), 7.87 (d, 1H), 7.97 (d, 2H).

MS (ESI) m/z 582 [M+H]+.

Anal. calcd for $C_{32}H_{40}FN_3O_6$: C, 66.08; H, 6.93; N, 7.22. Found: C, 65.98; H, 7.02 N, 7.34.

EXAMPLE 118

4-(1-cyclopentyl-7-fluoro-1H-indazol-3-yl)phenyl ethylcarbamate

A solution of 4-(1-cyclopentyl-7-fluoro-1H-indazol-3-yl) phenol (0.30 g, 1.0 mmol) and ethyl isocyanate (0.080 mL, 1.0 mmol) in 10 mL of dioxane was heated at 80° C. for 48 hours. The reaction mixture was concentrated in vacuo. The residue was crystallized from EtOAc/hexane to give 0.275 g of the title compound as a white solid.

mp 159–160° C.

¹H NMR (DMSO-d₆): δ 1.09 (dt, 3H), 1.713 (m, 2H), 1.892 (m, 2H), 2.15 (m, 4H), 3.112 (m, 2H), 5.294 (m, 1H), 7.17 (m, 1H), 7.25 (m, 3H), 7.79 (m, 1H), 7.84 (d, 1H 7.91 (m, 2H).

MS (ESI) m/z 368 [M+H]+.

Anal. calcd for $C_{21}H_{22}FN_3O_2$: C, 68.65; H, 6.04; N, 11.44. Found: C, 68.40; H, 5.87; N, 11.37.

EXAMPLE 119

4-(1-cyclopentyl-7-fluoro-1H-indazol-3-yl)phenyl tert-butylcarbamate

A solution of 4-(1-cyclopentyl-7-fluoro-1H-indazol-3-yl) phenol (0.30 g, 1.0 mmol) and t-butyl isocyanate (0.114 mL, 1.0 mmol) in 10 mL of dioxane was heated at 80° C. for 48 hours. The reaction mixture was concentrated in vacuo. The residue was crystallized from EtOAc/hexane to give 0.195 g of the title compound as a white solid.

mp 157° C.;

¹H NMR (DMSO-d₆): δ 1.295 (s, 9H), 1.712 (m, 2H), 1.898 (m, 2H), 2.15 (m, 4H), 4.15 (d, 2H), 5.294 (m, 1H), 7.06 (m, 1H), 7.18 (m, 1H), 7.22 (d, 2H), 7.28 (m, 1H), 7.62 (s, 1H), 7.84 (d, 1H), 7.91 (d, 2H).

MS (ESI) m/z 396 [M+H]+.

Anal. calcd for $C_{23}H_{26}FN_3O_2$: C, 69.85; H, 6.63; N, 10.63. Found: C, 70.21; H, 6.82; N, 10.63.

EXAMPLE 120

4-(1-cyclopentyl-7-fluoro-1H-indazol-3-yl)phenyl ethyl hydrogen phosphate

A solution of 4-(1-cyclopentyl-7-fluoro-1H-indazol-3-yl) phenol (0.30 g, 1.0 mmol), ethyl dichlorophosphate (0.13 mL, 1.1 mmol), and lithiumhexamethyldisilazide (0.183 g, 1.1 mmol) in 10 mL of THF was stirred for 1 hour at ambient temperature. The reaction mixture was quenched with H₂O and concentrated in vacuo. The residues were purified by reversed phase HPLC (Column: HS Hyperprep C18 8 u ID 22 mm; solvent gradient 40% to 100% acetonitrile (0.1% TFA) in H₂O; flowrate 10 mL/min) to give 0.065 g of the title compound as a white solid.

¹H NMR (DMSO-d₆): δ 1.12 (m, 3H), 1.706 (m, 2H), 1.893 (m, 2H), 2.14 (m, 4H), 3.38 (m, 2H), 5.27 (m, 1H), 7.14 (m, 1H), 7.28 (m, 3H), 7.82 (m, 3H).

MS (ESI) m/z 403 [M–H]–.

EXAMPLE 121

4-(1-cyclopentyl-7-fluoro-1H-indazol-3-yl)phenyl phenyl hydrogen phosphate

A solution of 4-(1-cyclopentyl-7-fluoro-1H-indazol-3-yl) phenol (0.30 g, 1.0 mmol), phenyl dichlorophosphate (0.211 mL, 1.1 mmol), and lithiumhexamethyidisilazide (0.183 g, 1.1 mmol) in 10 mL of THF was stirred for 1 hour at ambient temperature. The reaction mixture was quenched with H₂O and concentrated in vacuo. The residues were purified by reversed phase HPLC (Column: HS Hyperprep C18 8 u ID 22 mm; solvent gradient 40% to 100% acetonitrile (0.1% TFA) in H₂O; flowrate 10 mL/min) to give 0.120 g of the title compound as an oil.

¹H NMR (DMSO-d₆): δ δ 1.16 (m, 3H), 1.70 (m, 2H), 1.89 (m, 2H), 2.14 (m, 4H), 5.28 (m, 1H), 7.06 (m, 1H), 7.18 (m, 3H), 7.23–7.34 (m, 5H), 7.84 (m, 3H).

MS (ESI) m/z 453 [M+H]+.

EXAMPLE 122

4-(7-chloro-1-propyl-1H-indazol-3-yl)phenyl 3,3-dimethylbutanoate

To a solution of 4-(7-chloro-1-propyl-1H-indazol-3-yl) phenol (0.100 g, 0.35 mmol) and N,N-diisopropylethyl amine (0.5 g, 0.38 mmol) in CH₂Cl₂ (5 mL) was added dropwise tert-butylacetyl chloride (0.051 g, 0.38 mmol). The solution was allowed to stir overnight at room temperature. Water was added and the solution was extracted with CH₂Cl₂. The organic layer was washed with brine and dried (MgSO₄). The product was purified by flash chromatography (5/1 hexane/ethyl acetate) to yield a white solid (0.098 g, 72%).

mp 71–72° C.;

¹H NMR (DMSO-d₆): δ 0.89 (t, 3H, J=7.3 Hz), 1.09 (s, 9H), 1.88 (q, 2H, J=7.3 Hz), 4.72 (t, 2H, J=7.3 Hz), 7.22 (t,

1H, J=7.5 Hz), 7.26 (d, 2H, J=8.7 Hz), 7.53 (d, 1H, J=7.5 Hz), 7.95 (d, 2H, J=8.8 Hz), 8.02 (d, 1H, J=8.3 Hz)

MS (ESI) m/z 385 [M+H]+.

Anal. calcd for $C_{22}H_{25}ClN_2O_2$: C, 68.65; H, 6.55; N, 7.28. Found: C, 68.78; H, 6.42; N, 7.29.

EXAMPLE 123

4-(7-chloro-1-propyl-1H-indazol-3-yl)phenyl propionate

To a solution of 4-(7-chloro-1-propyl-1H-indazol-3-yl) phenol (0.100 g, 0.35 mmol) and N,N-diisopropylethyl amine (0.5 g, 0.38 mmol) in $CH_2Cl_2$ (5 mL) was added dropwise propionyl chloride (0.035 g, 0.38 mmol). The solution was allowed to stir overnight at room temperature. Water was added and the solution was extracted with $CH_2Cl_2$. The organic layer was washed with brine and dried ($MgSO_4$). The product was purified by flash chromatography (5/1 hexane/ethyl acetate) to yield a white solid (0.106 g, 88%).

mp 66–67° C.;

$^1$H NMR (DMSO-$d_6$): δ 0.89 (t, 3H, J=7.3 Hz), 1.15 (t, 3H, J=7.5 Hz), 1.88 (q, 2H, J=7.3 Hz), 2.64 (q, 2H, J=7.5 Hz), 4.72 (t, 2H, J=7.3 Hz), 7.21 (t, 1H, J=7.5 Hz), 7.28 (d, 2H, J=8.7 Hz), 7.53 (d, 1H, J=7.5 Hz), 7.94 (d, 2H, J=8.8 Hz), 8.03 (d, 1H, J=8.3 Hz).

MS (ESI) m/z 343 [M+H]+.

Anal. calcd for $C_{19}H_{19}ClN_2O_2$: C, 66.57; H, 5.59; N, 8.17. Found: C, 66.57; H, 5.64; N, 8.11.

EXAMPLES 124 to 224

Library synthesis of 4-(substituted-indazol-3-yl)-phenols

To the (substituted-2-fluorobenzyl-)4-methoxyphenyl) methanone (~0.075 mmol) was added a solution of a substituted-hydrazine (0.60 mL, 0.25mmol, 3 eq) in pyridine (6 hydrazines: methyl, butyl, benzyl, 2-hydroxyethyl, and hydrazine). The vials were heated for 6 days at 80° C. The pyridine was evaporated in vacuo and the residue partitioned with 1 mL EtOAc and $H_2O$. The EtOAc layer was concentrated in vacuo to provide the intermediate substituted-3-(4-methoxyphenyl)-indazoles.

The 4-(substituted-indazol-3-yl)-phenols were obtained by treatment of a solution of substituted 3-(4-methoxyphenyl)-indazoles in 0.7 mL of $CH_2Cl_2$/cyclohexene, (6:1, v/v) at −30° C. with boron tribromide (0.8 mL). Allowed to warm to ambient temperature over 5 hours. Quenched with 0.2 mL methanol and diluted with 2 mL $CH_2Cl_2$. The organic phases were washed with saturated aqueous $NaHCO_3$ and concentrated in vacuo. The residues were purified by HPLC and plated as a solution in 0.8 mL of DMSO.

Table 2 is a summary of the examples prepared.

| Example # | Chemical Name |
| --- | --- |
| 124 | 4-(1-methyl-1H-indazol-3-yl)phenol |
| 125 | 4-(6-chloro-5-fluoro-1-methyl-1H-indazol-3-yl)phenol |
| 126 | 4-(7-chloro-1-methyl-1H-indazol-3-yl)phenol |
| 127 | 4-[1-methyl-6-(trifluoromethyl)-1H-indazol-3-yl]benzene-1,3-diol |
| 128 | 4-(6-chloro-1-methyl-1H-indazol-3-yl)phenol |
| 129 | 4-[1-methyl-6-(trifluoromethyl)-1H-indazol-3-yl]phenol |
| 130 | 4-(H-indazol-3-yl)phenol |

-continued

| Example # | Chemical Name |
| --- | --- |
| 131 | 4-(6-chloro-5-fluoro-1H-indazol-3-yl)phenol |
| 132 | 4-(7-chloro-1H-indazol-3-yl)phenol |
| 133 | 4-(5-fluoro-1H-indazol-3-yl)phenol |
| 134 | 4-(6-chloro-1H-indazol-3-yl)phenol |
| 135 | 4-[7-(trifluoromethyl)-1H-indazol-3-yl]phenol |
| 136 | 4-[6-(trifluoromethyl)-1H-indazol-3-yl]phenol |
| 137 | 4-[5-(trifluoromethyl)-1H-indazol-3-yl]phenol |
| 138 | 4-[6-(trifluoromethyl)-1H-indazol-3-yl]benzene-1,2-diol |
| 139 | 4-(1-butyl-1H-indazol-3-yl)phenol |
| 140 | 4-(1-benzyl-1H-indazol-3-yl)phenol |
| 141 | 4-(1-benzyl-6-chloro-5-fluoro-1H-indazol-3-yl)phenol |
| 142 | 4-(1-benzyl-7-chloro-1H-indazol-3-yl)phenol |
| 143 | 4-[1-benzyl-7-(trifluoromethyl)-1H-indazol-3-yl]benzene-1,3-diol |
| 144 | 4-[1-benzyl-6-(trifluoromethyl)-1H-indazol-3-yl]benzene-1,3-diol |
| 145 | 4-(1-benzyl-7-fluoro-1H-indazol-3-yl)phenol |
| 146 | 4-(1-benzyl-6-chloro-1H-indazol-3-yl)phenol |
| 147 | 4-[1-benzyl-7-(trifluoromethyl)-1H-indazol-3-yl]phenol |
| 148 | 4-[1-benzyl-6-(trifluoromethyl)-1H-indazol-3-yl]phenol |
| 149 | 4-(1-benzyl-7-chloro-1H-indazol-3-yl)benzene-1,3-diol |
| 150 | 4-[1-benzyl-5-(trifluoromethyl)-1H-indazol-3-yl]phenol |
| 151 | 4-(1-benzyl-7-fluoro-1H-indazol-3-yl)benzene-1,3-diol |
| 152 | 4-(1-benzyl-6-chloro-1H-indazol-3-yl)benzene-1,3-diol |
| 153 | 4-(1-benzyl-6-chloro-5-fluoro-1H-indazol-3-yl)benzene-1,2-diol |
| 154 | 4-(1-benzyl-7-chloro-1H-indazol-3-yl)benzene-1,2-diol |
| 155 | 4-(1-benzyl-7-fluoro-1H-indazol-3-yl)benzene-1,2-diol |
| 156 | 4-(1-benzyl-6-chloro-1H-indazol-3-yl)benzene-1,2-diol |
| 157 | 4-[1-benzyl-7-(trifluoromethyl)-1H-indazol-3-yl]benzene-1,2-diol |
| 158 | 4-[1-(2-hydroxyethyl)-1H-indazol-3-yl]phenol |
| 159 | 4-[6-chloro-5-fluoro-1-(2-hydroxyethyl)-1H-indazol-3-yl]phenol |
| 160 | 4-[7-chloro-1-(2-hydroxyethyl)-1H-indazol-3-yl]phenol |
| 161 | 4-[6-chloro-1-(2-hydroxyethyl)-1H-indazol-3-yl]phenol |
| 162 | 4-[1-(2-hydroxyethyl)-7-(trifluoromethyl)-1H-indazol-3-yl]phenol |
| 163 | 4-[1-(2-hydroxyethyl)-6-(trifluoromethyl)-1H-indazol-3-yl]phenol |
| 164 | 4-[1-(2-hydroxyethyl)-1H-indazol-3-yl]benzene-1,3-diol |
| 165 | 4-[1-(2-hydroxyethyl)-5-(trifluoromethyl)-1H-indazol-3-yl]phenol |
| 166 | 4-[1-(2-hydroxyethyl)-6-(trifluoromethyl)-1H-indazol-3-yl]-benzene-1,2-diol |
| 167 | 4-[1-methyl-7-(trifluoromethyl)-1H-indazol-3-yl]benzene-1,3-diol |
| 168 | 4-(5-fluoro-1-methyl-1H-indazol-3-yl)phenol |
| 169 | 4-[1-methyl-7-(trifluoromethyl)-1H-indazol-3-yl]phenol |
| 170 | 4-(7-chloro-1-methyl-1H-indazol-3-yl)benzene-1,3-diol |
| 171 | 4-[1-methyl-5-(trifluoromethyl)-1H-indazol-3-yl]phenol |
| 172 | 4-(5-fluoro-1-methyl-1H-indazol-3-yl)benzene-1,3-di |
| 173 | 4-(7-chloro-1-methyl-1H-indazol-3-yl)benzene-1,2-diol |
| 174 | 4-(7-fluoro-1-methyl-1H-indazol-3-yl)benzene-1,2-diol |
| 175 | 4-(5-fluoro-1-methyl-1H-indazol-3-yl)benzene-1,2-diol |
| 176 | 4-[1-methyl-7-(trifluoromethyl)-1H-indazol-3-yl]benzene-1,2-diol |
| 177 | 4-(1,5-dimethyl-1H-indazol-3-yl)benzene-1,2-diol |
| 178 | 4-[1-methyl-5-(trifluoromethyl)-1H-indazol-3-yl]benzene-1,2-diol |
| 179 | 4-(H-indazol-3-yl)benzene-1,3-diol |
| 180 | 4-(1-butyl-7-chloro-1H-indazol-3-yl)phenol |
| 181 | 4-(1-butyl-7-chloro-1H-indazol-3-yl)benzene-1,2-diol |
| 182 | 4-[1-benzyl-5-(trifluoromethyl)-1H-indazol-3-yl]benzene-1,3-diol |
| 183 | 4-(1-benzyl-1H-indazol-3-yl)benzene-1,3-diol |
| 184 | 4-(1-benzyl-5-methyl-1H-indazol-3-yl)phenol |
| 185 | 4-(1-benzyl-1H-indazol-3-yl)benzene-1,2-diol |
| 186 | 4-(1-benzyl-5-fluoro-1H-indazol-3-yl)benzene-1,2-diol |
| 187 | 4-[1-(2-hydroxyethyl)-6-(trifluoromethyl)-1H-indazol-3-yl]-benzene-1,3-diol |
| 188 | 4-[7-fluoro-1-(2-hydroxyethyl)-1H-indazol-3-yl]phenol |
| 189 | 4-[5-fluoro-1-(2-hydroxyethyl)-1H-indazol-3-yl]phenol |
| 190 | 4-[1-(2-hydroxyethyl)-5-methyl-1H-indazol-3-yl]benzene-1,3-diol |
| 191 | 4-[7-fluoro-1-(2-hydroxyethyl)-1H-indazol-3-yl]benzene-1,3-diol |

| Example # | Chemical Name |
|---|---|
| 192 | 4-[5-fluoro-1-(2-hydroxyethyl)-1H-indazol-3-yl]benzene-1,3-diol |
| 193 | 4-[6-chloro-1-(2-hydroxyethyl)-1H-indazol-3-yl]benzene-1,3-diol |
| 194 | 4-[6-chloro-5-fluoro-1-(2-hydroxyethyl)-1H-indazol-3-yl]benzene-1,2-diol |
| 195 | 4-[6-chloro-1-(2-hydroxyethyl)-1H-indazol-3-yl]benzene-1,2-diol |
| 196 | 4-[1-(2-hydroxyethyl)-7-(trifluoromethyl)-1H-indazol-3-yl]-benzene-1,2-diol |
| 197 | 4-[1-(2-hydroxyethyl)-5-(trifluoromethyl)-1H-indazol-3-yl]-benzene-1,2-diol |
| 198 | 4-[1-butyl-6-(trifluoromethyl)-1H-indazol-3-yl]phenol |
| 199 | 4-(1-butyl-6-chloro-1H-indazol-3-yl)phenol |
| 200 | 4-(7-fluoro-1-methyl-1H-indazol-3-yl)phenol |
| 201 | 4-[7-(trifluoromethyl)-1H-indazol-3-yl]benzene-1,2-diol |
| 202 | 4-(1H-indazol-3-yl)benzene-1,2-diol |
| 203 | 4-(7-fluoro-1H-indazol-3-yl)phenol |
| 204 | 4-(7-chloro-1H-indazol-3-yl)benzene-1,2-diol |
| 205 | 4-[1-butyl-6-(trifluoromethyl)-1H-indazol-3-yl]benzene-1,2-diol |
| 206 | 4-[1-butyl-5-(trifluoromethyl)-1H-indazol-3-yl]phenol |
| 207 | 4-[1-methyl-6-(trifluoromethyl)-1H-indazol-3-yl]benzene-1,2-diol |
| 208 | 4-(5-chloro-6-fluoro-1-methyl-1H-indazol-3-yl)phenol |
| 209 | 4-(5-chloro-6-fluoro-1-methyl-1H-indazol-3-yl)benzene-1,2-diol |
| 210 | 4-[5-chloro-6-fluoro-1-(2-hydroxyethyl)-1H-indazol-3-yl]phenol |
| 211 | 4-[5-chloro-6-fluoro-1-(2-hydroxyethyl)-1H-indazol-3-yl]benzene-1,2-diol |
| 212 | 4-[5-chloro-6-fluoro-1-(2-hydroxyethyl)-1H-indazol-3-yl]benzene-1,2-diol |
| 213 | 4-(5-chloro-6-fluoro-1H-indazol-3-yl)benzene-1,2-diol |
| 214 | 4-[5-(trifluoromethyl)-1H-indazol-3-yl]benzene-1,2-diol |
| 215 | 4-(6-chloro-1H-indazol-3-yl)benzene-1,2-diol |
| 216 | 4-(1-butyl-7-fluoro-1H-indazol-3-yl)benzene-1,2-diol |
| 217 | 4-(1-butyl-5-chloro-6-fluoro-1H-indazol-3-yl)phenol |
| 218 | 4-(1-butyl-5-chloro-6-fluoro-1H-indazol-3-yl)benzene-1,2-diol |
| 219 | 4-[1-butyl-7-(trifluoromethyl)-1H-indazol-3-yl]phenol |
| 220 | 4-(1-butyl-7-fluoro-1H-indazol-3-yl)phenol |
| 221 | 4-[1-butyl-5-(trifluoromethyl)-1H-indazol-3-yl]benzene-1,2-diol |
| 222 | 4-(1-butyl-6-chloro-1H-indazol-3-yl)benzene-1,2-diol |
| 223 | 4-(1-benzyl-5-chloro-6-fluoro-1H-indazol-3-yl)phenol |
| 224 | 4-(1-benzyl-5-chloro-6-fluoro-1H-indazol-3-yl)benzene-1,2-diol |

Table 3 is a summary of structure elucidation via exact mass (ESI_FT)

| Example # | Exact m/z [M + H]$^{1+}$ | Exptl. m/z [M + H]$^{1+}$ | Error (mmu) |
|---|---|---|---|
| 124 | 225.10224 | 225.10233 | 0.09 |
| 125 | 277.05385 | 277.05385 | 0 |
| 126 | 259.06327 | 259.06327 | 0 |
| 127 | 309.08454 | 309.08466 | 0.12 |
| 128 | 259.06327 | 259.0633 | 0.03 |
| 129 | 293.08963 | 293.08954 | −0.09 |
| 130 | 211.08659 | 211.08665 | 0.06 |
| 131 | 263.0382 | 263.03826 | 0.06 |
| 132 | 245.04762 | 245.04767 | 0.05 |
| 133 | 229.07717 | 229.0773 | 0.13 |
| 134 | 245.04762 | 245.04767 | 0.05 |
| 135 | 279.07398 | 279.07396 | −0.02 |
| 136 | 279.07398 | 279.07399 | 0.01 |
| 137 | 279.07398 | 279.07393 | −0.05 |
| 138 | 295.06889 | 295.06901 | 0.12 |
| 139 | 267.14919 | 267.14917 | −0.02 |
| 140 | 301.13354 | 301.13353 | −0.01 |
| 141 | 353.08515 | 353.08525 | 0.1 |
| 142 | 335.09457 | 335.09438 | −0.19 |
| 143 | 385.11584 | 385.11551 | −0.33 |
| 144 | 385.11584 | 385.11551 | −0.33 |
| 145 | 319.12412 | 319.12405 | −0.07 |
| 146 | 335.09457 | 335.09443 | −0.14 |
| 147 | 369.12093 | 369.12078 | −0.15 |
| 148 | 369.12093 | 369.12068 | −0.25 |
| 149 | 351.08949 | 351.08953 | 0.04 |
| 150 | 369.12093 | 369.1208 | −0.13 |
| 151 | 335.11904 | 335.11887 | −0.17 |
| 152 | 351.08949 | 351.08962 | 0.13 |
| 153 | 369.08006 | 369.07998 | −0.08 |
| 154 | 351.08949 | 351.08951 | 0.02 |
| 155 | 335.11904 | 335.11894 | −0.1 |
| 156 | 351.08949 | 351.08967 | 0.18 |
| 157 | 385.11584 | 385.11553 | −0.31 |
| 158 | 255.11281 | 255.11256 | −0.25 |
| 159 | 307.06441 | 307.06443 | 0.02 |
| 160 | 289.07384 | 289.07383 | −0.01 |
| 161 | 289.07384 | 289.07383 | −0.01 |
| 162 | 323.10019 | 323.10011 | −0.08 |
| 163 | 323.10019 | 323.10005 | −0.14 |
| 164 | 271.10772 | 271.10774 | 0.02 |
| 165 | 323.10019 | 323.10012 | −0.07 |
| 166 | 339.09511 | 339.09496 | −0.15 |
| 167 | 309.08454 | 309.08475 | 0.21 |
| 168 | 243.09282 | 243.09295 | 0.13 |
| 169 | 293.08963 | 293.08973 | 0.1 |
| 170 | 275.05819 | 275.05851 | 0.32 |
| 171 | 293.08963 | 293.08973 | 0.1 |
| 172 | 259.08774 | 259.08791 | 0.17 |
| 173 | 275.05819 | 275.05852 | 0.33 |
| 174 | 259.08774 | 259.08792 | 0.18 |
| 175 | 259.08774 | 259.08794 | 0.2 |
| 176 | 309.08454 | 309.08462 | 0.08 |
| 177 | 255.11281 | 255.11298 | 0.17 |
| 178 | 309.08454 | 309.08468 | 0.14 |
| 179 | 227.08151 | 227.08172 | 0.21 |
| 180 | 301.11022 | 301.11036 | 0.14 |
| 181 | 317.10514 | 317.10528 | 0.14 |
| 182 | 385.11584 | 385.11582 | −0.02 |
| 183 | 317.12846 | 317.12883 | 0.37 |
| 184 | 315.14919 | 315.14935 | 0.16 |
| 185 | 317.12846 | 317.12864 | 0.18 |
| 186 | 335.11904 | 335.11914 | 0.1 |
| 187 | 339.09511 | 339.09539 | 0.28 |
| 188 | 273.10339 | 273.10348 | 0.09 |
| 189 | 273.10339 | 273.10355 | 0.16 |
| 190 | 285.12337 | 285.1236 | 0.23 |
| 191 | 289.0983 | 289.09838 | 0.08 |
| 192 | 289.0983 | 289.09856 | 0.26 |
| 193 | 305.06875 | 305.06891 | 0.16 |
| 194 | 323.05933 | 323.05956 | 0.23 |
| 195 | 305.06875 | 305.06899 | 0.24 |
| 196 | 339.09511 | 339.0951 | −0.01 |
| 197 | 339.09511 | 339.09531 | 0.2 |
| 198 | 335.13658 | 335.13639 | −0.19 |
| 199 | 301.11022 | 301.1101 | −0.12 |
| 200 | 243.09282 | 243.0928 | −0.02 |
| 201 | 295.06889 | 295.06881 | −0.08 |
| 202 | 227.08151 | 227.08147 | −0.04 |
| 203 | 229.07717 | 229.07713 | −0.04 |
| 204 | 261.04254 | 261.04254 | 0 |
| 205 | 351.13149 | 351.13146 | −0.03 |
| 206 | 335.13658 | 335.13644 | −0.14 |
| 207 | 309.08454 | 309.08445 | −0.09 |
| 208 | 277.05385 | 277.05382 | −0.03 |
| 209 | 293.04876 | 293.0487 | −0.06 |
| 210 | 307.06441 | 307.0644 | −0.01 |
| 211 | 323.05933 | 323.05923 | −0.1 |
| 212 | 245.07209 | 245.07209 | 0 |
| 213 | 279.03311 | 279.03311 | 0 |
| 214 | 295.06889 | 295.06882 | −0.07 |
| 215 | 261.04254 | 261.04252 | −0.02 |
| 216 | 301.13469 | 301.13463 | −0.06 |
| 217 | 319.1008 | 319.10068 | −0.12 |
| 218 | 335.09571 | 335.09564 | −0.07 |

-continued

| Example # | Exact m/z [M + H]$^{1+}$ | Exptl. m/z [M + H]$^{1+}$ | Error (mmu) |
|---|---|---|---|
| 219 | 335.13658 | 335.13655 | −0.03 |
| 220 | 285.13977 | 285.13964 | −0.13 |
| 221 | 351.13149 | 351.13147 | −0.02 |
| 222 | 317.10514 | 317.10509 | −0.15 |
| 223 | 353.08515 | 353.08514 | −0.01 |
| 224 | 369.0801 | 369.0802 | 0.14 |

EXAMPLES 225 to 267

Library synthesis of 4-(7-substituted-indazol-3-yl)-phenols

Under an atmosphere of argon, a series of 2 dram vials were charged with 1-substituted-7-bromo-3-(4-methoxyphenyl)-indazole (0.05 mL of 2M solution in dioxane, 0.10 mmol), substituted boronic acid (0.15 mL of 1.0 M sol'n in dioxane, 0.15 mmol), sodium carbonate (0.1 mL aqueous solution) and tetrakis(triphenylphosphine) palladium (0) (0.025 mL of 0.1 M solution in dioxane). The vials were heated at 85° C. for 6 hours. The reaction mixtures were partitioned with 3 mL EtOAc and 2 mL of 0.5N NaOH. The EtOAc layer was concentrated in vacuo to provide the indazole intermediate 1,7-disubstituted-3-(4-methoxyphenyl)-indazoles.

The 4-(1,7-disubstituted-indazol-3-yl)-phenols were obtained by treatment of a solution of 4-(1,7-disubstituted-indazol-3-yl)-phenols in 0.7 mL of CH$_2$Cl$_2$/cyclohexene, (6:1, v/v) at −30° C. with boron tribromide (0.8 mL). Allowed to warm to ambient temperature over 5 hours. Quenched with 0.2 mL methanol and diluted with 2 mL CH$_2$Cl$_2$. The organic phases were washed with saturated aqueous NaHCO$_3$ and concentrated in vacuo. The residues were purified by HPLC and plated as a solution in 0.8 mL of DMSO.

Table 4 is a summary of the examples prepared.

| Example # | Chemical Name |
|---|---|
| 225 | 4-{1-isopropyl-7-[4-(trifluoromethyl)phenyl]-1H-indazol-3-yl}-phenol |
| 226 | 4-(1-isopropyl-7-thien-3-yl-1H-indazol-3-yl)phenol |
| 227 | 4-(1-isopropyl-7-thien-2-yl-1H-indazol-3-yl)phenol |
| 228 | 4-{1-isopropyl-7-[4-(methylthio)phenyl]-1H-indazol-3-yl}phenol |
| 229 | 4-{7-[(E)-hept-1-enyl]-1-isopropyl-1H-indazol-3-yl}phenol |
| 230 | 4-{7-[4-(hydroxymethyl)phenyl]-1-isopropyl-1H-indazol-3-yl}-phenol |
| 231 | 4-[3-(4-hydroxyphenyl)-1-isopropyl-1H-indazol-7-yl]benzene-1,2-diol |
| 232 | 4-[7-(4-ethylphenyl)-1-isopropyl-1H-indazol-3-yl]phenol |
| 233 | 4-[7-(1,1'-biphenyl-4-yl)-1-isopropyl-1H-indazol-3-yl]phenol |
| 234 | 4-[7-(2-chlorophenyl)-1-isopropyl-1H-indazol-3-yl]phenol |
| 235 | 4-[1-isopropyl-7-(2-methylphenyl)-1H-indazol-3-yl]phenol |
| 236 | 4-(1-isopropyl-7-phenyl-1H-indazol-3-yl)phenol |
| 237 | 4-{1-cyclopentyl-7-[4-(trifluoromethyl)phenyl]-1H-indazol-3-yl}-phenol |
| 238 | 4-(1-cyclopentyl-7-thien-2-yl-1H-indazol-3-yl)phenol |
| 239 | 4-{1-cyclopentyl-7-[4-(methylthio)phenyl]-1H-indazol-3-yl}phenol |
| 240 | 4-[1-cyclopentyl-3-(4-hydroxyphenyl)-1H-indazol-7-yl]benzene-1,2-diol |
| 241 | 4-[1-cyclopentyl-7-(4-ethylphenyl)-1H-indazol-3-yl]phenol |
| 242 | 4-[7-(1,1'-biphenyl-4-yl)-1-cyclopentyl-1H-indazol-3-yl]phenol |
| 243 | 4-[7-(2-chlorophenyl)-1-cyclopentyl-1H-indazol-3-yl]phenol |
| 244 | 4-[1-cyclopentyl-7-(2-furyl)-1H-indazol-3-yl]phenol |
| 245 | 4-[1-cyclopentyl-7-(2-methylphenyl)-1H-indazol-3-yl]phenol |
| 246 | 4-(1-cyclopentyl-7-phenyl-1H-indazol-3-yl)phenol |
| 247 | 4-(1-isopropyl-7-thien-3-yl-1H-indazol-3-yl)-3-methylphenol |
| 248 | 4-{7-[(E)-hept-1-enyl]-1-isopropyl-1H-indazol-3-yl}-3-methyl-phenol |
| 249 | 4-{7-[14-(hydroxymethyl)phenyl]-1-isopropyl-1H-indazol-3-yl}-3-methylphenol |
| 250 | 4-[3-(4-hydroxy-2-methylphenyl)-1-isopropyl-1H-indazol-7-yl]-benzene-1,2-diol |
| 251 | 4-[7-(4-ethylphenyl)-1-isopropyl-1H-indazol-3-yl]-3-methylphenol |
| 252 | 4-[7-(1,1'-biphenyl-4-yl)-1-isopropyl-1H-indazol-3-yl]-3-methyl-phenol |
| 253 | 4-[7-(2-chlorophenyl)-1-isopropyl-1H-indazol-3-yl]-3-methyl-phenol |
| 254 | 4-[7-(2-furyl)-1-isopropyl-1H-indazol-3-yl]-3-methylphenol |
| 255 | 4-[1-isopropyl-7-(2-methylphenyl)-1H-indazol-3-yl]-3-methyl-phenol |
| 256 | 4-[1-isopropyl-7-(2-methylphenyl)-1H-indazol-3-yl]-3-methyl-phenol |
| 257 | 4-{1-cyclopentyl-7-[4-(methylthio)phenyl]-1H-indazol-3-yl}-3-methylphenol |
| 258 | 4-{1-cyclopentyl-7-[(E)-hept-1-enyl]-1H-indazol-3-yl}-3-methyl-phenol |
| 259 | 4-[1-cyclopentyl-3-(4-hydroxy-2-methylphenyl)-1H-indazol-7-yl]benzene-1,2-diol |
| 260 | 4-[1-cyclopentyl-7-(4-ethylphenyl)-1H-indazol-3-yl]-3-methyl-phenol |
| 261 | 4-[7-(1,1'-biphenyl-4-yl)-1-cyclopentyl-1H-indazol-3-yl]-3-methylphenol |
| 262 | 4-[7-(2-chlorophenyl)-1-cyclopentyl-1H-indazol-3-yl]-3-methyl-phenol |
| 263 | 4-[1-cyclopentyl-7-(2-furyl)-1H-indazol-3-yl]-3-methylphenol |
| 264 | 4-[1-cyclopentyl-7-(2-methylphenyl)-1H-indazol-3-yl]-3-methyl-phenol |
| 265 | 4-(1-cyclopentyl-7-phenyl-1H-indazol-3-yl)-3-methylphenol |
| 266 | 4-[7-(1-benzothien-2-yl)-1-cyclopentyl-1H-indazol-3-yl]-3-methylphenol |
| 267 | 4-[7-(2-furyl)-1-isopropyl-1H-indazol-3-yl]phenol |

Table 5 is a summary of structure elucidation via exact mass (ESI_FT)

| Example # | Exact m/z [M + H]$^{1+}$ | Exptl. m/z [M + H]$^{1+}$ | Error (mmu) |
|---|---|---|---|
| 225 | 397.1522 | 397.1521 | −0.1 |
| 226 | 335.1213 | 335.1212 | −0.03 |
| 227 | 335.1213 | 335.1212 | −0.04 |
| 228 | 375.1526 | 375.1525 | −0.04 |
| 229 | 349.2274 | 349.2276 | 0.11 |
| 230 | 359.1754 | 359.1754 | −0.02 |
| 231 | 361.1547 | 361.1547 | 0.06 |
| 232 | 357.1962 | 357.1962 | 0.04 |
| 233 | 405.1961 | 405.1961 | −0.04 |
| 234 | 363.1259 | 363.1259 | 0.06 |
| 235 | 343.1805 | 343.1806 | 0.08 |
| 236 | 329.1648 | 329.1649 | 0.03 |
| 237 | 423.1679 | 423.1678 | −0.12 |
| 238 | 361.1369 | 361.137 | 0.05 |
| 239 | 401.1682 | 401.1681 | −0.09 |
| 240 | 387.1703 | 387.1703 | −0.05 |
| 241 | 383.2118 | 383.2118 | −0.02 |
| 242 | 431.2118 | 431.2117 | −0.07 |
| 243 | 389.1415 | 389.1415 | −0.05 |
| 244 | 345.1598 | 345.1598 | 0.07 |
| 245 | 369.1961 | 369.1961 | −0.06 |
| 246 | 355.1805 | 355.1805 | 0 |
| 247 | 349.1369 | 349.137 | 0.08 |
| 248 | 363.2431 | 363.2432 | 0.08 |
| 249 | 373.1911 | 373.1911 | 0.01 |

-continued

| Example # | Exact m/z [M + H]$^{1+}$ | Exptl. m/z [M + H]$^{1+}$ | Error (mmu) |
|---|---|---|---|
| 250 | 375.1703 | 375.1704 | 0.06 |
| 251 | 371.2118 | 371.2118 | 0.02 |
| 252 | 419.2118 | 419.2117 | −0.06 |
| 253 | 377.1415 | 377.1416 | 0.11 |
| 254 | 333.1598 | 333.1599 | 0.09 |
| 255 | 357.1961 | 357.1962 | 0.06 |
| 256 | 343.1805 | 343.1806 | 0.12 |
| 257 | 415.1839 | 415.1838 | −0.02 |
| 258 | 389.2587 | 389.2587 | −0.04 |
| 259 | 401.186 | 401.186 | 0 |
| 260 | 397.2274 | 397.2274 | −0.05 |
| 261 | 445.2274 | 445.2274 | 0 |
| 262 | 403.1572 | 403.1572 | −0.01 |
| 263 | 359.1754 | 359.1754 | 0.02 |
| 264 | 383.2118 | 383.2117 | −0.11 |
| 265 | 369.1961 | 369.196 | −0.16 |
| 266 | 425.1682 | 425.168 | −0.18 |
| 267 | 319.1441 | 319.1441 | −0.05 |

The invention claimed is:

1. A compound of formulae I or II having the structure

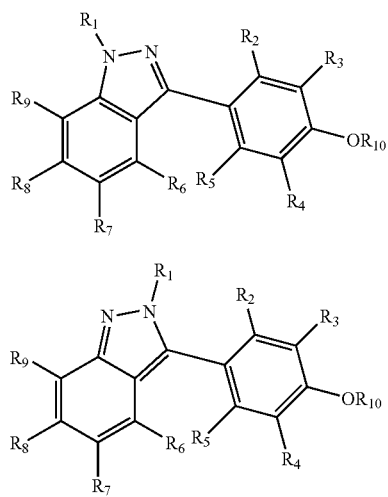

wherein $R_1$ is alkyl of 1–6 carbon atoms, alkenyl of 2–7 carbon atoms, cycloalkyl of 3–8 carbon atoms, cycloalkenyl of 4–8 carbon atoms, aryl of 6–20 carbon atoms, or arylalkyl of 7–26 carbon atoms;

$R_2$, $R_3$, and $R_5$, are each, independently, hydrogen, alkyl of 1–6 carbon atoms, alkenyl of 2–7 carbon atoms, hydroxy, alkoxy of 1–6 carbon atoms, aryloxy of 6–20 carbon atoms, halogen, trifluoromethyl, —CN, —NO$_2$, —CHO, or —CO$_2$R$_{11}$;

$R_4$ is hydrogen;

$R_6$, $R_7$, and $R_8$, are each, independently, hydrogen, alkyl of 1–6 carbon atoms, alkenyl of 2–7 carbon atoms, hydroxy, alkoxy of 1–6 carbon atoms, aryloxy of 6–20 carbon atoms, halogen, trifluoromethyl, —CO$_2$ R$_{11}$, aryl of 6–20 carbon atoms, or arylalkyl of 7–26 carbon atoms;

$R_9$ is alkyl of 1–6 carbon atoms, alkenyl of 2–7 carbon atoms, hydroxy, alkoxy of 1–6 carbon atoms, aryloxy of 6–20 carbon atoms, halogen, trifluoromethyl, —CO$_2$ R$_{11}$, aryl of 6–20 carbon atoms, or arylalkyl of 7–26 carbon atoms;

$R_{10}$ is hydrogen, —CO R$_{11}$, —CONH R$_{11}$, —P(═O)(OH)OR$_{11}$, or —CO(CH$_2$)$_n$CH(NHR$_{12}$)CO$_2$R$_{11}$;

$R_{11}$ is hydrogen, alkyl of 1–6 carbon atoms, aryl of 6–20 carbon atoms, or arylalkyl of 7–26 carbon atoms;

$R_{12}$ is hydrogen or —CO$_2$R$_{11}$;

n=0–3, or a pharmaceutically acceptable salt thereof.

2. The compound according to claim 1, wherein $R_1$ is alkyl of 1–6 carbon atoms, alkenyl of 2–7 carbon atoms, cycloalkyl of 3–8 carbon atoms, or cycloalkenyl of 4–8 carbon atoms;

$R_2$ is hydrogen, alkyl of 1–6 carbon atoms, alkenyl of 2–7 carbon atoms, hydroxy, alkoxy of 1–6 carbon atoms, or halogen;

$R_7$ is hydrogen, alkyl of 1–6 carbon atoms, hydroxy, halogen, trifluoromethyl, —CO$_2$R$_{11}$, aryl of 6–20 carbon atoms, or arylalkyl of 7–26 carbon atoms;

$R_9$ is alkyl of 1–6 carbon atoms, hydroxy, halogen, trifluoromethyl, —CO$_2$R$_{11}$, aryl of 6–20 carbon atoms, or arylalkyl of 7–26 carbon atoms;

or a pharmaceutical acceptable salt thereof.

3. The compound according to claim 2, wherein $R_1$ is alkyl of 1–6 carbon atoms, alkenyl of 2–7 carbon atoms, cycloalkyl of 3–8 carbon atoms, or cycloalkenyl of 4–8 carbon atoms;

$R_2$ is hydrogen, alkyl of 1–6 carbon atoms, halogen, or hydroxy;

$R_9$ is alkyl of 1–6 carbon atoms, halogen, trifluoromethyl, —CO$_2$R$_{11}$, aryl of 6–20 carbon atoms, or arylalkyl of 7–26 carbon atoms;

$R_{10}$ is hydrogen;

or a pharmaceutically acceptable salt thereof.

4. The compound according to claim 3, wherein $R_1$ is alkyl of 1–6 carbon atoms or alkenyl of 2–7 carbon atoms;

$R_9$ is alkyl of 1–6 carbon atoms, halogen, or trifluoromethyl;

or a pharmaceutically acceptable salt thereof.

5. A compound, which is a) 4-(6-chloro-5-fluoro-1-methyl-1H-indazol-3-yl)phenol;

b) 4-(7-chloro-1-methyl-1H-indazol-3-yl)phenol;

d) 4-(6-chloro-5-fluoro-1H-indazol-3-yl)phenol;

e) 4-(6-chloro-1H-indazol-3-yl)phenol;

f) 4-(1-butyl-1H-indazol-3-yl)phenol;

g) 4-(1-benzyl-7-chloro-1H-indazol-3-yl)phenol;

h) 4-[1-benzyl-7-(trifluoromethyl)-1H-indazol-3-yl]benzene-1,3-diol;

i) 4-(1-benzyl-7-fluoro-1H-indazol-3-yl)phenol;

j) 4-[1-benzyl-7-(trifluoromethyl)-1H-indazol-3-yl]phenol;

k) 4-(1-benzyl-7-chloro-1H-indazol-3-yl)benzene-1,3-diol;

l) 1-(4-(1-benzyl-7-fluoro-1H-indazol-3-yl)-1,3-benzenediol;

m) 4-[1-(2-hydroxyethyl)-1H-indazol-3-yl]phenol;

n) 4-[1-(2-hydroxyethyl)-7-(trifluoromethyl)-1H-indazol-3-yl]phenol;

o) 4-[1-methyl-7-(trifluoromethyl)-1H-indazol-3-yl]benzene-1,3-diol;

p) 4-(5-fluoro-1-methyl-1H-indazol-3-yl)phenol;

q) 4-[1-methyl-7-(trifluoromethyl)-1H-indazol-3-yl]phenol;

r) 4-(7-chloro-1-methyl-1H-indazol-3-yl)benzene-1,3-diol;
s) 4-[1-methyl-S-(trifluoromethyl)-1H-indazol-3-yl]phenol;
t) 4-(5-fluoro-1-methyl-1H-indazol-3-yl)benzene-1,3-diol;
u) 4-[1-methyl-7-(trifluoromethyl)-1H-indazol-3-yl]benzene-1,2-diol;
v) 4-(1-butyl-7-chloro-1H-indazol-3-yl)phenol;
w) 4-[1-benzyl-5-(trifluoromethyl)-1H-indazol-3-yl]benzene-1,3-diol;
x) 4-(1-benzyl-1H-indazol-3-yl)benzene-1,3-diol;
y) 4-[7-fluoro-1-(2-hydroxyethyl)-1H-indazol-3-yl]phenol;
z) 4-[5-fluoro-1-(2-hydroxyethyl)-1H-indazol-3-yl]benzene-1,3-diol;
aa) 4-[1-(2-chlorophenyl)-6-hydroxy-1H-indazol-3-yl]benzene-1,3-diol;
bb) 4-[6-hydroxy-1-(4-methoxyphenyl)-1H-indazol-3-yl]benzene-1,3-diol;
cc) 4-[6-hydroxy-1-(2-methoxyphenyl)-1H-indazol-3-yl]benzene-1,3-diol;
dd) 4-{6-hydroxy-1-[4-(trifluoromethoxy)phenyl]-1H-indazol-3-yl}benzene-1,3-diol;
ee) 4-[1-(3-bromophenyl)-6-hydroxy-1H-indazol-3-yl]benzene-1,3-diol;
ff) 4-[1-(4-bromophenyl)-6-hydroxy-1H-indazol-3-yl]benzene-1,3-diol;
gg) 4-[3-(2,4-dihydroxyphenyl)-6-hydroxy-1H-indazol-1-yl]benzonitrile;
hh) 4-[1-(3-chlorophenyl)-6-hydroxy-1H-indazol-3-yl]benzene-1,3-diol;
ii) 4-(1-ethyl-6-hydroxy-1H-indazol-3-yl)benzene-1,3-diol;
jj) 4-(6-hydroxy-1-propyl-1H-indazol-3-yl)benzene-1,3-diol;
kk) 4-(1-butyl-6-hydroxy-1H-indazol-3-yl)benzene-1,3-diol;
ll) 4-(1-cyclohexyl-6-hydroxy-1H-indazol-3-yl)benzene-1,3-diol;
mm) 4-[6-hydroxy-1-(2,2,2-trifluoroethyl)-1H-indazol-3-yl]benzene-1,3-diol;
nn) 4-[1-(3-fluorophenyl)-6-hydroxy-1H-indazol-3-yl]benzene-1,3-diol;
oo) 4-[6-hydroxy-1-(4-methyiphenyl)-1H-indazol-3-yl]benzene-1,3-diol;
pp) 4-[1-(2-fluorophenyl)-6-hydroxy-1H-indazol-3-yl]benzene-1,3-diol;
qq) 4-[6-hydroxy-1-(3-methyiphenyl)-1H-indazol-3-yl]benzene-1,3-diol;
rr) 4-(7-chloro-1-cyclohexyl-1H-indazol-3-yl)phenol;
ss) 4-[1-(4-bromophenyl)-7-(trifluoromethyl)-1H-indazol-3-yl]phenol;
tt) 4-[1-cyclohexyl-7-(trifluoromethyl)-1H-indazol-3-yl]phenol;
uu) 4-(7-methyl-1H-indazol-3-yl)phenol;
vv) 4-[1-(3-chloro-4-fluorophenyl)-6-hydroxy-1H-indazol-3-yl]benzene-1,3-diol;
ww) 4-{6-hydroxy-1-[3-(trifluoromethyl)phenyl]-1H-indazol-3-yl}benzene-1,3-diol;
xx) 4-[6-hydroxy-1-(3-nitrophenyl)-1H-indazol-3-yl]benzene-1,3-diol;
yy) 4-[6-hydroxy-1-(4-isopropylphenyl)-1H-indazol-3-yl]benzene-1,3-diol;
zz) 4-{6-hydroxy-1-[4-(methylsulfonyl)phenyl]-1H-indazol-3-yl}benzene-1,3-diol;
aaa) 4-(7-methyl-1-propyl-1H-indazol-3-yl)phenol;
bbb) 4-(1-isopropyl-7-methyl-1H-indazol-3-yl)phenol;
ccc) 4-(7-chloro-1-pentyl-1H-indazol-3-yl)phenol;
ddd) 4-(7-chloro-1-propyl-1H-indazol-3-yl)phenol;
eee) 4-(7-chloro-1-isopropyl-1H-indazol-3-yl)phenol;
fff) 4-[1-pentyl-7-(trifluoromethyl)-1H-indazol-3-yl]phenol;
ggg) 4-[1-isopropyl-7-(trifluoromethyl)-1H-indazol-3-yl]phenol;
hhh) 4-[1propyl-7-(trifluoromethyl)-1H-indazol-3-yl]phenol;
iii) 4-(7-methyl-2-propyl-2H-indazol-3-yl)phenol;
jjj) 4-[2-isopropyl-7-methyl-2H-indazol-3-yl]phenol;
kkk) 4-(7-chloro-2-pentyl-2H-indazol-3-yl)phenol;
lll) 4-(7-chloro-2-propyl-2H-indazol-3-yl)phenol;
mmm) 4-(7-chloro-2-isopropyl-2H-indazol-3-yl)phenol;
nnn) 4-[1-butyl-6-(trifluoromethyl)-1H-indazol-3-yl]phenol;
ooo) 4-(1-butyl-6-chloro-1H-indazol-3-yl)phenol;
ppp) 4-(7-fluoro-1-methyl-1H-indazol-3-yl)phenol;
qqq) 4-(1H-indazol-3-yl)benzene-1,2-diol;
rrr) 4-(7-fluoro-1H-indazol-3-yl)phenol;
sss) 4-[1-butyl-5-(trifluoromethyl)-1H-indazol-3-yl]phenol;
ttt) 4-(1-cyclohexyl-7-fluoro-1H-indazol-3-yl)phenol;
uuu) 4-(1-allyl-7-fluoro-1H-indazol-3-yl)phenol;
vvv) 4-(1-allyl-7-methyl-1H-indazol-3-yl)phenol;
www) 4-[1-allyl-7-(trifluoromethyl)-1H-indazol-3-yl]phenol;
xxx) 4-(7-chloro-1-cyclopentyl-1H-indazol-3-yl)phenol;
yyy) 4-(7-fluoro-1-propyl-1H-indazol-3-yl)phenol;
zzz) 4-(7-fluoro-1-isopropyl-1H-indazol-3-yl)phenol;
aaaa) 4-(1-cyclopentyl-7-fluoro-1H-indazol-3-yl)phenol;
bbbb) 4-[1-butyl-7-(trifluoromethyl)-1H-indazol-3-yl]phenol;
cccc) 4-(1-butyl-7-fluoro-1H-indazol-3-yl)phenol;
dddd) 4-[2-allyl-7-(trifluoromethyl)-2H-indazol-3-yl]phenol;
eeee) 4-(7-chloro-2-cyclopentyl-2H-indazol-3-yl)phenol;
ffff) 4-(2-cyclopentyl-7-fluoro-2H-indazol-3-yl)phenol;
gggg) 4-(7-fluoro-2-isopropyl-2H-indazol-3-yl)phenol;
hhhh) 4-(7-fluoro-2-propyl-2H-indazol-3-yl)phenol;
iiii) 4-[7-fluoro-1-(3,3,3-trifluoropropyl)-1H-indazol-3-yl]phenol;
jjjj) 4-[1-allyl-7-(trifluoromethyl)-1H-indazol-3-yl]-3-methylphenol;
kkkk) 3-methyl-4-[1-propyl-7-(trifluoromethyl)-1H-indazol-3-yl]phenol;
llll) 4-[1-allyl-7-(trifluoromethyl)-1H-indazol-3-yl]benzene-1,3-diol;
mmmm) 4-[1-pentyl-7-(trifluoromethyl)-1H-indazol-3-yl]benzene-1,3-diol;
nnnn) 4-[2-allyl-7-(trifluoromethyl)-2H-indazol-3-yl]-3-methylphenol;
oooo) 4-[2-allyl-7-(trifluoromethyl)-2H-indazol-3-yl]-1,3-benzenediol;
pppp) 4-(7-chloro-1-isopropyl-1H-indazol-3-yl)-3-methylphenol;
qqqq) 4-(7-chloro-2-isopropyl-2H-indazol-3-yl)-3-methylphenol;
rrrr) 4-(7-chloro-1-propyl-1H-indazol-3-yl)-3-methylphenol;
ssss) 4-(7-chloro-2-propyl-2H-indazol-3-yl)-3-methylphenol;
tttt) 4-(1-allyl-7-chloro-1H-indazol-3-yl)-3-methylphenol;
uuuu) 4-(2-allyl-7-chloro-2H-indazol-3-yl)-3-methylphenol;

vvvv) 4-(1-cyclopentyl-7-fluoro-1H-indazol-3-yl)-2-methylphenol;
wwww) 4-(7-chloro-1-cyclopentyl-1H-indazol-3-yl)-3-methylphenol;
xxxx) 4-(7-chloro-1-isopropyl-1H-indazol-3-yl)benzene-1,3-diol;
yyyy) 4-(1-allyl-7-chloro-1H-indazol-3-yl)benzene-1,3-diol;
zzzz) 4-[1-isopropyl-7-(trifluoromethyl)-1H-indazol-3-yl]-3-methylphenol;
ccccc) 4-{1-isopropyl-7-[4-(methylthio)phenyl]-1H-indazol-3-yl}phenol;
ddddd) 4-{7-[4-(hydroxymethyl)phenyl]-1-isopropyl-1H-indazol-3-yl}phenol;
eeeee) 4-[3-(4-hydroxyphenyl)-1-isopropyl-1H-indazol-7-yl]benzene-1,2-diol;
fffff) 4-[7-(4-ethylphenyl)-1-isopropyl-1H-indazol-3-yl]phenol;
ggggg) 4-[7-(1,1'-biphenyl-4-yl)-1-isopropyl-1H-indazol-3-yl]phenol;
hhhhh) 4-[7-(2-chlorophenyl)-1-isopropyl-1H-indazol-3-yl]phenol;
iiiii) 4-[1-isopropyl-7-(2-methylphenyl)-1H-indazol-3-yl]phenol;
jjjjj) 4-(1-isopropyl-7-phenyl-1H-indazol-3-yl)phenol;
kkkkk) 4-{1-cyclopentyl-7-[4-(trifluoromethyl)phenyl]-1H-indazol-3-yl}phenol;
mmmmm) 4-[1-cyclopentyl-3-(4-hydroxyphenyl)-1H-indazol-7-yl]benzene-1,2-diol;
nnnnn) 4-[1-cyclopentyl-7-(4-ethylphenyl)-1H-indazol-3-yl]phenol;
ooooo) 4-[7-(2-chlorophenyl)-1-cyclopentyl-1H-indazol-3-yl]phenol;
qqqqq) 4-[1-cyclopentyl-7-(2-methylphenyl)-1H-indazol-3-yl]phenol;
rrrrr) 4-(1-cyclopentyl-7-phenyl-1H-indazol-3-yl)phenol;
ttttt) 4-{7-[(1E)-hept-1-enyl]-1-isopropyl-1H-indazol-3-yl}-3-methylphenol;
uuuuu) 4-{7-[4-(hydroxymethyl)phenyl]-1-isopropyl-1H-indazol-3-yl}-3-methylphenol;
vvvvv) 4-[3-(4-hydroxy-2-methylphenyl)-1-isopropyl-1H-indazol-7-yl]benzene-1,2-diol;
wwwww) 4-[7-(4-ethylphenyl)-1-isopropyl-1H-indazol-3-yl]-3-methylphenol;
xxxxx) 4-[7-(1,1'-biphenyl-4-yl)-1-isopropyl-1H-indazol-3-yl]-3-methylphenol;
yyyyy) 4-[7-(2-chlorophenyl)-1-isopropyl-1H-indazol-3-yl]-3-methylphenol;
aaaaaa) 4-[1-isopropyl-7-(2-methylphenyl)-1H-indazol-3-yl]-3-methylphenol;
bbbbbb) 4-(1-isopropyl-7-phenyl-1H-indazol-3-yl)-3-methylphenol;
cccccc) 4-{1-cyclopentyl-7-[4-(methylthio)phenyl]-1H-indazol-3-yl}-3-methylphenol;
dddddd) 4-{1-cyclopentyl-7-[(1E)-hept-1-enyl]-1H-indazol-3-yl}-3-methylphenol;
eeeeee) 4-[1-cyclopentyl-3-(4-hydroxy-2-methylphenyl)-1H-indazol-7-yl]benzene-1,2-diol;
ffffff) 4-[1-cyclopentyl-7-(4-ethylphenyl)-1H-indazol-3-yl]-3-methylphenol;
gggggg) 4-[7-(1,1'-biphenyl-4-yl)-1-cyclopentyl-1H-indazol-3-yl]-3-methylphenol;
hhhhhh) 4-[7-(2-chlorophenyl)-1-cyclopentyl-1H-indazol-3-yl]-3-methylphenol;
jjjjjj) 4-[1-cyclopentyl-7-(2-methylphenyl)-1H-indazol-3-yl]-3-methylphenol;
kkkkkk) 4-(1-cyclopentyl-7-phenyl-1H-indazol-3-yl)-3-methylphenol;
nnnnnn) 4-(7-fluoro-1-propyl-1H-indazol-3-yl)-3-methylphenol;
oooooo) 4-(7-fluoro-2-propyl-2H-indazol-3-yl)-3-methylphenol;
pppppp) 4-(7-fluoro-1-isopropyl-1H-indazol-3-yl)-3-methylphenol;
qqqqqq) 4-(1-cyclopentyl-7-fluoro-1H-indazol-3-yl)benzene-1,3-diol;
rrrrrr) 4-(7-fluoro-1-isobutyl-1H-indazol-3-yl)-3-methylphenol;
ssssss) 4-(7-fluoro-1-isopropyl-1H-indazol-3-yl)benzene-1,3-diol;
tttttt) 4-(7-fluoro-2-isopropyl-2H-indazol-3-yl)benzene-1,3-diol;
uuuuuu) 4-(7-fluoro-1-isobutyl-1H-indazol-3-yl)benzene-1,3-diol;
vvvvvv) 4-[3-(4-hydroxyphenyl)-1-propyl-1H-indazol-7-yl]phenol;
wwwwww) 4-[7-(4-fluorophenyl)-1-propyl-1H-indazol-3-yl]phenol;
yyyyyy) 4-(7-phenyl-2-propyl-2H-indazol-3-yl)phenol;
zzzzzz) 4-(7-phenyl-1-propyl-1H-indazol-3-yl)phenol;
aaaaaaa) 4-(1-cyclopentyl-7-fluoro-1H-indazol-3-yl)phenyl pivalate;
bbbbbbb) 4-(7-chloro-1-propyl-1H-indazol-3-yl)phenyl3,3-dimethylbutanoate;
ccccccc) 4-(7-chloro-1-propyl-1H-indazol-3-yl)phenyl propionate;
ddddddd) 4-(1-cyclopentyl-7-fluoro-1H-indazol-3-yl) phenyl acetate;
eeeeeee) 4-(1-cyclopentyl-7-fluoro-1H-indazol-3-yl)phenyl propionate;
fffffff) 4-(1-cyclopentyl-7-fluoro-1H-indazol-3-yl)phenyl-N-(tert-butoxycarbonyl)glycylglycinate;
ggggggg) 1-tert-butyl-5-[4-(1-cyclopentyl-7-fluoro-1H-indazol-3-yl)phenyl]-N-(tert-butoxycarbonyl)-L-glutamate;
hhhhhhh) 4-(1-cyclopentyl-7-fluoro-1H-indazol-3-yl) phenyl ethylcarbamate;
jjjjjjj) 4-[1-isopropyl-7-(trifluoromethyl)-1H-indazol-3-yl]benzene-1,3-diol;
kkkkkkk) methyl3-(4-hydroxyphenyl)-2-isopropyl-2H-indazole-7-carboxylate;
lllllll ) 4-[1-cyclopentyl-7-(trifluoromethyl)-1H-indazol-3-yl]benzene-1,3-diol;
mmmmmmm) 4-[1-(cyclohexylmethyl)-7-(trifluoromethyl)-1H-indazol-3-yl]benzene-1,3-diol;
nnnnnnn) 4-[1-isobutyl-7-(trifluoromethyl)-1H-indazol-3-yl]benzene-1,3-diol;
ooooooo) 4-[1-cyclobutyl-7-(trifluoromethyl)-1H-indazol-3-yl]benzene-1,3-diol; or
ppppppp) 4-[1-(2-ethylbutyl)-7-(trifluoromethyl)-1H-indazol-3-yl]benzene-1,3-diol,
or a pharmaceutically acceptable salt thereof.

6. A pharmaceutical composition, which comprises a compound according to claim 1 or claim 5.

7. A compound of claim 5 that is 4-[1-allyl-7-(trifluoromethyl)-1H-indazol-3-yl]benzene-1,3-diol; or a pharmaceutically acceptable salt thereof.

8. A compound of claim 5 that is
4-(7-chloro-1-methyl-1H-indazol-3-yl)phenol;
4-(1-benzyl-7-chloro-1H-indazol-3-yl)phenol;
4-[1-benzyl-7-(trifluoromethyl)-1H-indazol-3-yl]benzene-1,3-diol;
4-(1-benzyl-7-fluoro-1H-indazol-3-yl)phenol;

4-[1-benzyl-7-(trifluoromethyl)-1H-indazol-3-yl]phenol;
4-(1-benzyl-7-chloro-1H-indazol-3-yl)benzene-1,3-diol;
4-(1-benzyl-7-fluoro-1H-indazol-3-yl)-1,3-benzenediol;
4-[1-(2-hydroxyethyl)-7-(trifluoromethyl)-1H-indazol-3-yl]phenol;
4-[1-methyl-7-(trifluoromethyl)-1H-indazol-3-yl]benzene-1,3-diol;
4-[1-methyl-7-(trifluoromethyl)-1H-indazol-3-yl]phenol;
4-(7-chloro-1-methyl-1H-indazol-3-yl)benzene-1,3-diol;
4-[1-methyl-7-(trifluoromethyl)-1H-indazol-3-yl]benzene-1,2-diol;
4-(1-butyl-7-chloro-1H-indazol-3-yl)phenol;
4-(7-chloro-1-cyclohexyl-1H-indazol-3-yl)phenol;
4-[1-(4-bromophenyl)-7-(trifluoromethyl)-1H-indazol-3-yl]phenol;
4-[1-cyclohexyl-7-(trifluoromethyl)-1H-indazol-3-yl]phenol;
4-(7-methyl-1-propyl-1H-indazol-3-yl)phenol;
4-(1-isopropyl-7-methyl-1H-indazol-3-yl)phenol;
4-(7-chloro-1-pentyl-1H-indazol-3-yl)phenol;
4-(7-chloro-1-propyl-1H-indazol-3-yl)phenol;
4-(7-chloro-1-isopropyl-1H-indazol-3-yl)phenol;
4-[1-pentyl-7-(trifluoromethyl)-1H-indazol-3-yl]phenol;
4-[1-isopropyl-7-(trifluoromethyl)-1H-indazol-3-yl]phenol;
4-[1propyl-7-(trifluoromethyl)-1H-indazol-3-yl]phenol;
4-(7-methyl-2-propyl-2H-indazol-3-yl)phenol;
4-[2-isopropyl-7-methyl-2H-indazol-3-yl]phenol;
4-(7-chloro-2-pentyl-2H-indazol-3-yl)phenol;
4-(7-chloro-2-propyl-2H-indazol-3-yl)phenol;
4-(7-chloro-2-isopropyl-2H-indazol-3-yl)phenol;
4-(7-fluoro-1-methyl-1H-indazol-3-yl)phenol;
4-(1-cyclohexyl-7-fluoro-1H-indazol-3-yl)phenol;
4-(1-allyl-7-fluoro-1H-indazol-3-yl)phenol;
4-(1-allyl-7-methyl-1H-indazol-3-yl)phenol;
4-[1-allyl-7-(trifluoromethyl)-1H-indazol-3-yl]phenol;
4-(7-chloro-1-cyclopentyl-1H-indazol-3-yl)phenol;
4-(7-fluoro-1-propyl-1H-indazol-3-yl)phenol;
4-(7-fluoro-1-isopropyl-1H-indazol-3-yl)phenol;
4-(1-cyclopentyl-7-fluoro-1H-indazol-3-yl)phenol;
4-[1-butyl-7-(trifluoromethyl)-1H-indazol-3-yl]phenol;
4-(1-butyl-7-fluoro-1H-indazol-3-yl)phenol;
4-[2-allyl-7-(trifluoromethyl)-2H-indazol-3-yl]phenol;
4-(7-chloro-2-cyclopentyl-2H-indazol-3-yl)phenol;
4-(2-cyclopentyl-7-fluoro-2H-indazol-3-yl)phenol;
4-(7-fluoro-2-isopropyl-2H-indazol-3-yl)phenol;
4-(7-fluoro-2-propyl-2H-indazol-3-yl)phenol;
4-[7-fluoro-1-(3,3,3-trifluoropropyl)-1H-indazol-3-yl)phenol;
4-[1-allyl-7-(trifluoromethyl)-1H-indazol-3-yl]-3-methylphenol;
3-methyl-4-[1-propyl-7-(trifluoromethyl)-1H-indazol-3-yl]phenol;
4-[1-allyl-7-(trifluoromethyl)-1H-indazol-3-yl]benzene-1,3-diol;
4-[1-pentyl-7-(trifluoromethyl)-1H-indazol-3-yl]benzene-1,3-diol;
4-[2-allyl-7-(trifluoromethyl)-2H-indazol-3-yl]-3-methylphenol;
4-[2-allyl-7-(trifluoromethyl)-2H-indazol-3-yl]-1,3-benzenediol;
4-(7-chloro-1-isopropyl-1H-indazol-3-yl)-3-methylphenol;
4-(7-chloro-2-isopropyl-2H-indazol-3-yl)-3-methylphenol;
4-(7-chloro-1-propyl-1H-indazol-3-yl)-3-methylphenol;
4-(7-chloro-2-propyl-2H-indazol-3-yl)-3-methylphenol;
4-(1-allyl-7-chloro-1H-indazol-3-yl)-3-methylphenol;
4-(2-allyl-7-chloro-2H-indazol-3-yl)-3-methylphenol;
4-(1-cyclopentyl-7-fluoro-1H-indazol-3-yl)-2-methylphenol;
4-(7-chloro-1-cyclopentyl-1H-indazol-3-yl)-3-methylphenol;
4-(7-chloro-1-isopropyl-1H-indazol-3-yl)benzene-1,3-diol;
4-(1-allyl-7-chloro-1H-indazol-3-yl)benzene-1,3-diol;
4-[1-isopropyl-7-(trifluoromethyl)-1H-indazol-3-yl]-3-methylphenol;
4-{1-isopropyl-7-[4-(methylthio)phenyl]-1H-indazol-3-yl}phenol;
4-{7-[4-(hydroxymethyl)phenyl]-1-isopropyl-1H-indazol-3-yl}phenol;
4-[3-(4-hydroxyphenyl)-1-isopropyl-1H-indazol-7-yl]benzene-1,2-diol;
4-[7-(4-ethylphenyl)-1-isopropyl-1H-indazol-3-yl]phenol;
4-[7-(1,1'-biphenyl-4-yl)-1-isopropyl-1H-indazol-3-yl]phenol;
4-[7-(2-chlorophenyl)-1-isopropyl-1H-indazol-3-yl]phenol;
4-[1-isopropyl-7-(2-methylphenyl)-1H-indazol-3-yl]phenol;
4-(1-isopropyl-7-phenyl-1H-indazol-3-yl)phenol;
4-{1-cyclopentyl-7-[4-(trifluoromethyl)phenyl]-1H-indazol-3-yl}phenol;
4-[1-cyclopentyl-3-(4-hydroxyphenyl)-1H-indazol-7-yl]benzene-1,2-diol;
4-[1-cyclopentyl-7-(4-ethylphenyl)-1H-indazol-3-yl]phenol;
4-[7-(2-chlorophenyl)-1-cyclopentyl-1H-indazol-3-yl]phenol;
4-[1-cyclopentyl-7-(2-methylphenyl)-1H-indazol-3-yl]phenol;
4-(1-cyclopentyl-7-phenyl-1H-indazol-3-yl)phenol;
4-{7-[(1E)-hept-1-enyl]-1-isopropyl-1H-indazol-3-yl}-3-methylphenol;
4-{7-[4-(hydroxymethyl)phenyl]-1-isopropyl-1H-indazol-3-yl}-3-methylphenol;
4-[3-(4-hydroxy-2-methylphenyl)-1-isopropyl-1H-indazol-7-yl]benzene-1,2-diol;
4-[7-(4-ethylphenyl)-1-isopropyl-1H-indazol-3-yl]-3-methylphenol;
4-[7-(1,1'-biphenyl-4-yl)-1-isopropyl-1H-indazol-3-yl]-3-methylphenol;
4-[7-(2-chlorophenyl)-1-isopropyl-1H-indazol-3-yl]-3-methylphenol;
4-[1-isopropyl-7-(2-methylphenyl)-1H-indazol-3-yl]-3-methylphenol;
4-(1-isopropyl-7-phenyl-1H-indazol-3-yl)-3-methylphenol;
4-{1-cyclopentyl-7-[4-(methylthio)phenyl]-1H-indazol-3-yl}-3-methylphenol;
4-{1-cyclopentyl-7-[(1E)-hept-1-enyl]-1H-indazol-3-yl}-3-methylphenol;
4-[1-cyclopentyl-3-(4-hydroxy-2-methylphenyl)-1H-indazol-7-yl]benzene-1,2-diol;
4-[1-cyclopentyl-7-(4-ethylphenyl)-1H-indazol-3-yl]-3-methylphenol;
4-[7-(1,1'-biphenyl-4-yl)-1-cyclopentyl-1H-indazol-3-yl]-3-methylphenol;
4-[7-(2-chlorophenyl)-1-cyclopentyl-1H-indazol-3-yl]-3-methylphenol;
4-[1-cyclopentyl-7-(2-methylphenyl)-1H-indazol-3-yl]-3-methylphenol;

4-(1-cyclopentyl-7-phenyl-1H-indazol-3-yl)-3-methylphenol;
4-(7-fluoro-1-propyl-1H-indazol-3-yl)-3-methylphenol;
4-(7-fluoro-2-propyl-2H-indazol-3-yl)-3-methylphenol;
4-(7-fluoro-1-isopropyl-1H-indazol-3-yl)-3-methylphenol;
4-(1-cyclopentyl-7-fluoro-1H-indazol-3-yl)benzene-1,3-diol;
4-(7-fluoro-1-isobutyl-1H-indazol-3-yl)-3-methylphenol;
4-(7-fluoro-1-isopropyl-1H-indazol-3-yl)benzene-1,3-diol;
4-(7-fluoro-2-isopropyl-2H-indazol-3-yl)benzene-1,3-diol;
4-(7-fluoro-1-isobutyl-1H-indazol-3-yl)benzene-1,3-diol;
4-[3-(4-hydroxyphenyl)-1-propyl-1H-indazol-7-yl]phenol;
4-[7-(4-fluorophenyl)-1-propyl-1H-indazol-3-yl]phenol;
4-(7-phenyl-2-propyl-2H-indazol-3-yl)phenol;
4-(7-phenyl-1-propyl-1H-indazol-3-yl)phenol;
4-(1-cyclopentyl-7-fluoro-1H-indazol-3-yl)phenyl pivalate;
4-(7-chloro-1-propyl-1H-indazol-3-yl)phenyl 3,3-dimethylbutanoate;
4-(7-chloro-1-propyl-1H-indazol-3-yl)phenyl propionate;
4-(1-cyclopentyl-7-fluoro-1H-indazol-3-yl)phenyl acetate;
4-(1-cyclopentyl-7-fluoro-1H-indazol-3-yl)phenyl propionate;
4-(1-cyclopentyl-7-fluoro-1H-indazol-3-yl)phenyl-N-(tert-butoxycarbonyl)glycylglycinate;
1-tert-butyl-5-[4-(1-cyclopentyl-7-fluoro-1H-indazol-3-yl)phenyl]-N-(tert-butoxycarbonyl)-L-glutamate;
4-(1-cyclopentyl-7-fluoro-1H-indazol-3-yl)phenyl ethylcarbamate;
4-[1-isopropyl-7-(trifluoromethyl)-1H-indazol-3-yl]benzene-1,3-diol;
methyl 3-(4-hydroxyphenyl)-2-isopropyl-2H-indazole-7-carboxylate;
4-[1-cyclopentyl-7-(trifluoromethyl)-1H-indazol-3-yl]benzene-1,3-diol;
4-[1-(cyclohexylmethyl)-7-(trifluoromethyl)-1H-indazol-3-yl]benzene-1,3-diol;
4-[1-isobutyl-7-(trifluoromethyl)-1H-indazol-3-yl]benzene-1,3-diol;
4-[1-cyclobutyl-7-(trifluoromethyl)-1H-indazol-3-yl]benzene-1,3-diol; or
4-[1-(2-ethylbutyl)-7-(trifluoromethyl)-1H-indazol-3-yl]benzene-1,3-diol;
or a pharmaceutically acceptable salt thereof.

* * * * *